(12) United States Patent
Wei et al.

(10) Patent No.: US 9,101,475 B2
(45) Date of Patent: Aug. 11, 2015

(54) SEGMENTED DELIVERY SYSTEM

(75) Inventors: Guobao Wei, Eatontown, NJ (US); Todd M. Boyce, Matawan, NJ (US); Robert Cohen, Rockaway, NJ (US); Cristy Richards, Matawan, NJ (US); Lawrence A. Shimp, Morganville, NJ (US)

(73) Assignee: Warsaw Orthopedic, Inc., Warsaw, IN (US)

(*) Notice: Subject to any disclaimer, the term of this patent is extended or adjusted under 35 U.S.C. 154(b) by 432 days.

(21) Appl. No.: 12/705,369

(22) Filed: Feb. 12, 2010

(65) Prior Publication Data

US 2010/0203155 A1  Aug. 12, 2010

Related U.S. Application Data

(60) Provisional application No. 61/152,057, filed on Feb. 12, 2009, provisional application No. 61/154,673, filed on Feb. 23, 2009, provisional application No. 61/154,689, filed on Feb. 23, 2009, provisional application No. 61/154,679, filed on Feb. 23, 2009.

(51) Int. Cl.
*A61F 2/28* (2006.01)
*A61F 2/30* (2006.01)
(Continued)

(52) U.S. Cl.
CPC .............. *A61F 2/30* (2013.01); *A61F 2/4603* (2013.01); *A61B 17/823* (2013.01); *A61F 2002/0086* (2013.01); *A61F 2002/2825* (2013.01); *A61F 2002/2835* (2013.01);
(Continued)

(58) Field of Classification Search
USPC ............ 623/17.12, 23.48–23.52, 16.11; 606/92–94
See application file for complete search history.

(56) References Cited

U.S. PATENT DOCUMENTS 4,172,128 A  10/1979 Thiele et al.
4,294,753 A  10/1981 Urist
(Continued)

FOREIGN PATENT DOCUMENTS

DE  2 253 086  9/1974
DE  693 24 117 T2  6/1994
(Continued)

OTHER PUBLICATIONS

Aspenberg et al., "Monkey Bone Matrix Induces Bone Formation in the Athymic Rat, but Not in Adult Monkeys," *J. of Orthop. Res.* 9:20-25 (1991).
(Continued)

*Primary Examiner* — Alvin Stewart
(74) *Attorney, Agent, or Firm* — Sorell Lenna & Schmidt LLP

(57) ABSTRACT

A covering for delivering a substance or material to a surgical site is provided. The covering, with substance provided therein, may be referred to as a delivery system. Generally, the covering may be a single or multi-compartment structure capable of at least partially retaining a substance provided therein until the covering is placed at a surgical site. Upon placement, the covering may facilitate transfer of the substance or surrounding materials. For example, the substance may be released (actively or passively) to the surgical site. The covering may participate in, control, or otherwise adjust the release of the substance. In various embodiments, the covering may be formed of a collagen material and is suitable for a variety of procedure specific uses.

9 Claims, 54 Drawing Sheets

(51) Int. Cl.
  *A61F 2/46* (2006.01)
  *A61B 17/82* (2006.01)
  *A61F 2/00* (2006.01)

(52) U.S. Cl.
  CPC .......... *A61F 2002/3007* (2013.01); *A61F 2002/30059* (2013.01); *A61F 2002/30064* (2013.01); *A61F 2002/3068* (2013.01); *A61F 2002/30072* (2013.01); *A61F 2002/3093* (2013.01); *A61F 2002/30588* (2013.01); *A61F 2002/30677* (2013.01); *A61F 2002/30971* (2013.01); *A61F 2002/4623* (2013.01); *A61F 2002/4627* (2013.01); *A61F 2250/0068* (2013.01); *A61F 2310/0097* (2013.01); *A61F 2310/00592* (2013.01); *A61F 2310/00958* (2013.01)

(56) References Cited

U.S. PATENT DOCUMENTS

| | | | | |
|---|---|---|---|---|
| 4,394,370 | A | 7/1983 | Jefferies | |
| 4,430,760 | A | 2/1984 | Smestad | |
| 4,440,370 | A | 4/1984 | Rood | |
| 4,440,750 | A | 4/1984 | Glowacki et al. | |
| 4,455,256 | A | 6/1984 | Urist | |
| 4,472,840 | A | 9/1984 | Jefferies | |
| 4,485,097 | A | 11/1984 | Bell | |
| 4,563,350 | A | 1/1986 | Nathan et al. | |
| 4,619,989 | A | 10/1986 | Urist | |
| 4,657,548 | A | 4/1987 | Nichols | |
| 4,678,470 | A | 7/1987 | Nashef et al. | |
| 4,743,259 | A | 5/1988 | Bolander et al. | |
| 4,755,184 | A | 7/1988 | Silverberg | |
| 4,761,471 | A | 8/1988 | Urist | |
| 4,774,228 | A | 9/1988 | Seyedin et al. | |
| 4,774,322 | A | 9/1988 | Seyedin et al. | |
| 4,787,906 | A | 11/1988 | Haris | |
| 4,789,663 | A | 12/1988 | Wallace et al. | |
| 4,789,732 | A | 12/1988 | Urist | |
| 4,795,804 | A | 1/1989 | Urist | |
| 4,804,744 | A | 2/1989 | Sen | |
| 4,810,691 | A | 3/1989 | Seyedin et al. | |
| 4,839,215 | A * | 6/1989 | Starling et al. | 428/131 |
| 4,843,063 | A | 6/1989 | Seyedin et al. | |
| 4,902,296 | A | 2/1990 | Bolander et al. | |
| 4,904,260 | A * | 2/1990 | Ray et al. | 623/17.12 |
| 4,919,668 | A * | 4/1990 | Rosenbaum et al. | 623/17.17 |
| 4,932,969 | A * | 6/1990 | Frey et al. | 623/17.12 |
| 5,041,138 | A | 8/1991 | Vacanti et al. | |
| 5,073,373 | A | 12/1991 | O'Leary et al. | |
| 5,106,748 | A | 4/1992 | Wozney et al. | |
| 5,166,187 | A | 11/1992 | Collombel et al. | |
| 5,211,664 | A | 5/1993 | Tepic et al. | |
| 5,236,456 | A | 8/1993 | O'Leary et al. | |
| 5,266,683 | A | 11/1993 | Oppermann et al. | |
| 5,270,300 | A | 12/1993 | Hunziker | |
| 5,284,655 | A | 2/1994 | Bogdansky et al. | |
| 5,290,558 | A | 3/1994 | O'Leary et al. | |
| 5,290,763 | A | 3/1994 | Poser et al. | |
| 5,314,476 | A | 5/1994 | Prewett et al. | |
| 5,336,264 | A | 8/1994 | Constanz et al. | |
| 5,354,557 | A | 10/1994 | Oppermann et al. | |
| 5,378,469 | A | 1/1995 | Kemp et al. | |
| 5,385,887 | A | 1/1995 | Yim et al. | |
| 5,405,390 | A | 4/1995 | O'Leary et al. | |
| 5,490,962 | A | 2/1996 | Cima et al. | |
| 5,501,706 | A | 3/1996 | Arenberg | |
| 5,507,813 | A | 4/1996 | Dowd et al. | |
| 5,518,680 | A | 5/1996 | Cima et al. | |
| 5,531,735 | A | 7/1996 | Thompson | |
| 5,549,679 | A * | 8/1996 | Kuslich | 623/17.12 |
| 5,563,124 | A | 10/1996 | Damien et al. | |
| 5,571,189 | A * | 11/1996 | Kuslich | 623/17.12 |
| 5,607,269 | A | 3/1997 | Dowd et al. | |
| 5,618,339 | A | 4/1997 | Ito | |
| 5,658,882 | A | 8/1997 | Celeste et al. | |
| 5,674,295 | A * | 10/1997 | Ray et al. | 623/17.12 |
| 5,723,012 | A | 3/1998 | Fages et al. | |
| 5,725,579 | A | 3/1998 | Fages et al. | |
| 5,755,797 | A * | 5/1998 | Baumgartner | 623/17.16 |
| 5,776,193 | A | 7/1998 | Kwan et al. | |
| 5,788,959 | A | 8/1998 | Singh | |
| 5,807,437 | A | 9/1998 | Sachs et al. | |
| 5,824,093 | A * | 10/1998 | Ray et al. | 623/17.16 |
| 5,830,493 | A | 11/1998 | Yokota et al. | |
| 5,846,484 | A | 12/1998 | Scarborough et al. | |
| 5,877,005 | A | 3/1999 | Castor et al. | |
| 5,894,070 | A | 4/1999 | Hansson et al. | |
| 5,899,939 | A | 5/1999 | Boyce et al. | |
| 5,902,562 | A | 5/1999 | Lagasse et al. | |
| 5,912,131 | A | 6/1999 | Eyre | |
| 5,961,554 | A * | 10/1999 | Janson et al. | 623/17.16 |
| 6,007,580 | A | 12/1999 | Lehto et al. | |
| 6,018,095 | A | 1/2000 | Lerch et al. | |
| 6,022,376 | A * | 2/2000 | Assell et al. | 623/17.16 |
| 6,030,635 | A | 2/2000 | Gertzman et al. | |
| 6,113,639 | A * | 9/2000 | Ray et al. | 623/17.16 |
| 6,117,646 | A | 9/2000 | Qvist et al. | |
| 6,120,558 | A | 9/2000 | Poddevin et al. | |
| 6,124,273 | A | 9/2000 | Drohan et al. | |
| 6,132,465 | A * | 10/2000 | Ray et al. | 623/17.16 |
| 6,143,030 | A | 11/2000 | Schroder | |
| 6,149,864 | A | 11/2000 | Dillow et al. | |
| 6,162,258 | A | 12/2000 | Scarborough et al. | |
| 6,180,606 | B1 | 1/2001 | Chen et al. | |
| 6,187,043 | B1 * | 2/2001 | Ledergerber | 623/8 |
| 6,197,325 | B1 | 3/2001 | MacPhee et al. | |
| 6,217,614 | B1 | 4/2001 | Fages et al. | |
| 6,245,537 | B1 | 6/2001 | Williams et al. | |
| 6,248,131 | B1 * | 6/2001 | Felt et al. | 623/17.12 |
| 6,267,767 | B1 * | 7/2001 | Strobel et al. | 606/104 |
| 6,294,041 | B1 | 9/2001 | Boyce et al. | |
| 6,294,187 | B1 | 9/2001 | Boyce et al. | |
| 6,311,690 | B1 | 11/2001 | Jefferies | |
| 6,326,018 | B1 | 12/2001 | Gertzman et al. | |
| 6,352,667 | B1 | 3/2002 | English | |
| 6,372,257 | B1 | 4/2002 | Marchosky | |
| 6,387,130 | B1 * | 5/2002 | Stone et al. | 623/17.16 |
| 6,387,391 | B1 | 5/2002 | Shikinami et al. | |
| 6,419,704 | B1 * | 7/2002 | Ferree | 623/17.12 |
| 6,436,138 | B1 | 8/2002 | Dowd et al. | |
| 6,440,444 | B2 | 8/2002 | Boyce et al. | |
| 6,443,988 | B2 * | 9/2002 | Felt et al. | 623/17.12 |
| 6,465,168 | B1 | 10/2002 | Castor et al. | |
| 6,468,543 | B1 | 10/2002 | Gilbertson et al. | |
| 6,478,825 | B1 | 11/2002 | Winterbottom et al. | |
| 6,482,234 | B1 * | 11/2002 | Weber et al. | 623/17.12 |
| 6,582,466 | B1 * | 6/2003 | Gauchet | 623/17.11 |
| 6,592,886 | B1 | 7/2003 | Zimmermann | |
| 6,595,998 | B2 | 7/2003 | Johnson et al. | |
| 6,599,515 | B1 | 7/2003 | Delmotte | |
| 6,616,698 | B2 | 9/2003 | Scarborough | |
| 6,618,698 | B1 | 9/2003 | Beausoleil et al. | |
| 6,623,749 | B2 | 9/2003 | Williams et al. | |
| 6,632,235 | B2 * | 10/2003 | Weikel et al. | 606/192 |
| 6,648,919 | B2 | 11/2003 | Ferree | |
| 6,696,073 | B2 | 2/2004 | Boyce et al. | |
| RE38,522 | E | 5/2004 | Gertzman et al. | |
| 6,733,533 | B1 * | 5/2004 | Lozier | 623/17.12 |
| 6,740,093 | B2 | 5/2004 | Hochschuler et al. | |
| 6,752,831 | B2 | 6/2004 | Sybert et al. | |
| 6,776,800 | B2 * | 8/2004 | Boyer et al. | 623/23.63 |
| 6,783,546 | B2 * | 8/2004 | Zucherman et al. | 623/17.16 |
| 6,843,807 | B1 | 1/2005 | Boyce et al. | |
| 6,884,428 | B2 | 4/2005 | Binette et al. | |
| 6,884,778 | B2 | 4/2005 | Jo et al. | |
| 6,911,212 | B2 | 6/2005 | Gertzman et al. | |
| 6,953,594 | B2 | 10/2005 | Lee et al. | |
| 6,969,404 | B2 | 11/2005 | Ferree | |
| 6,989,029 | B2 | 1/2006 | Bonutti | |
| 7,001,390 | B2 * | 2/2006 | Gebhardt et al. | 606/151 |
| 7,008,591 | B2 | 3/2006 | Kafesjian et al. | |
| 7,019,192 | B2 | 3/2006 | Gertzman et al. | |

(56) References Cited

U.S. PATENT DOCUMENTS

| | | | |
|---|---|---|---|
| 7,025,771 B2 | 4/2006 | Kuslich et al. | |
| 7,045,141 B2 | 5/2006 | Merboth et al. | |
| 7,060,287 B1 | 6/2006 | Hubbard et al. | |
| 7,108,832 B2 | 9/2006 | Christensen et al. | |
| 7,163,563 B2 * | 1/2007 | Schwartz et al. | 623/23.76 |
| 7,163,691 B2 | 1/2007 | Knaack et al. | |
| 7,179,299 B2 | 2/2007 | Edwards et al. | |
| 7,208,015 B2 | 4/2007 | Pointillart et al. | |
| 7,220,282 B2 | 5/2007 | Kuslich | |
| 7,226,481 B2 * | 6/2007 | Kuslich | 623/17.11 |
| 7,241,303 B2 | 7/2007 | Reiss et al. | |
| 7,261,720 B2 * | 8/2007 | Stevens et al. | 606/105 |
| 7,291,150 B2 * | 11/2007 | Graf | 606/86 A |
| 7,323,193 B2 * | 1/2008 | Morris et al. | 424/549 |
| 7,351,262 B2 * | 4/2008 | Bindseil et al. | 623/17.16 |
| 7,427,295 B2 * | 9/2008 | Ellman et al. | 623/17.16 |
| 7,465,318 B2 * | 12/2008 | Sennett et al. | 623/17.12 |
| 7,498,041 B2 * | 3/2009 | Masinaei et al. | 424/400 |
| 7,534,268 B2 * | 5/2009 | Hudgins et al. | 623/17.12 |
| 7,632,294 B2 * | 12/2009 | Milbodker et al. | 606/279 |
| 7,641,691 B2 * | 1/2010 | Lotz et al. | 623/17.12 |
| 7,666,205 B2 * | 2/2010 | Weikel et al. | 606/279 |
| 7,682,400 B2 * | 3/2010 | Zwirkoski | 623/23.48 |
| 7,731,753 B2 * | 6/2010 | Reo et al. | 623/17.13 |
| 7,799,079 B2 * | 9/2010 | Hestad et al. | 623/17.12 |
| 7,803,188 B2 * | 9/2010 | Justis et al. | 623/17.11 |
| 7,819,918 B2 * | 10/2010 | Malaviya et al. | 623/14.12 |
| 7,824,444 B2 * | 11/2010 | Biscup et al. | 623/17.12 |
| 7,939,108 B2 * | 5/2011 | Morris et al. | 424/549 |
| 7,947,079 B2 * | 5/2011 | Helm et al. | 623/17.12 |
| 7,967,864 B2 * | 6/2011 | Schaller | 623/17.11 |
| 7,993,402 B2 * | 8/2011 | Sidler | 623/17.11 |
| 8,012,211 B2 * | 9/2011 | Kuslich | 623/17.12 |
| 8,043,381 B2 * | 10/2011 | Hestad et al. | 623/17.16 |
| 8,092,529 B2 * | 1/2012 | Malaviya et al. | 623/14.12 |
| 8,110,003 B2 * | 2/2012 | Johnson et al. | 623/17.11 |
| 8,236,057 B2 * | 8/2012 | Wirtel et al. | 623/17.12 |
| 8,267,971 B2 * | 9/2012 | Dutoit et al. | 606/279 |
| 8,273,110 B2 * | 9/2012 | Seifert et al. | 606/279 |
| 2001/0031254 A1 | 10/2001 | Bianchi et al. | |
| 2001/0043258 A1 | 11/2001 | Ohki | |
| 2002/0058947 A1 * | 5/2002 | Hochschuler et al. | 606/94 |
| 2002/0068974 A1 * | 6/2002 | Kuslich et al. | 623/17.11 |
| 2002/0077701 A1 | 6/2002 | Kuslich | |
| 2002/0123750 A1 * | 9/2002 | Eisermann et al. | 606/69 |
| 2002/0133166 A1 | 9/2002 | McKay et al. | |
| 2002/0183848 A1 * | 12/2002 | Ray et al. | 623/17.12 |
| 2002/0197297 A1 | 12/2002 | Risbud et al. | |
| 2003/0004574 A1 * | 1/2003 | Ferree | 623/17.12 |
| 2003/0008328 A1 | 1/2003 | Wironen et al. | |
| 2003/0039676 A1 | 2/2003 | Boyce et al. | |
| 2003/0044445 A1 | 3/2003 | Kay et al. | |
| 2003/0065392 A1 | 4/2003 | Fan et al. | |
| 2003/0072677 A1 | 4/2003 | Kafesjian et al. | |
| 2003/0129178 A1 | 7/2003 | Wegman et al. | |
| 2003/0143258 A1 | 7/2003 | Knaack et al. | |
| 2003/0152548 A1 | 8/2003 | Mikos et al. | |
| 2003/0194708 A1 | 10/2003 | Binnerts et al. | |
| 2004/0023387 A1 | 2/2004 | Morris et al. | |
| 2004/0024457 A1 | 2/2004 | Boyce et al. | |
| 2004/0059364 A1 | 3/2004 | Gaskins et al. | |
| 2004/0072322 A1 | 4/2004 | Thorne | |
| 2004/0097930 A1 * | 5/2004 | Justis et al. | 606/61 |
| 2004/0133280 A1 * | 7/2004 | Trieu | 623/17.16 |
| 2004/0146543 A1 | 7/2004 | Shimp et al. | |
| 2004/0220615 A1 | 11/2004 | Lin | |
| 2004/0249464 A1 * | 12/2004 | Bindseil et al. | 623/17.16 |
| 2004/0249471 A1 * | 12/2004 | Bindseil et al. | 623/23.51 |
| 2005/0008620 A1 | 1/2005 | Shimp et al. | |
| 2005/0008672 A1 | 1/2005 | Winterbottom et al. | |
| 2005/0020506 A1 | 1/2005 | Drapeau et al. | |
| 2005/0027033 A1 | 2/2005 | Knaack et al. | |
| 2005/0037978 A1 | 2/2005 | Damien | |
| 2005/0090901 A1 * | 4/2005 | Studer | 623/17.12 |
| 2005/0131417 A1 | 6/2005 | Ahern et al. | |
| 2005/0154460 A1 * | 7/2005 | Yundt | 623/17.11 |
| 2005/0244450 A1 | 11/2005 | Reddi | |
| 2005/0244457 A1 | 11/2005 | Reddi | |
| 2005/0251267 A1 | 11/2005 | Winterbottom et al. | |
| 2005/0278023 A1 * | 12/2005 | Zwirkoski | 623/11.11 |
| 2005/0283255 A1 * | 12/2005 | Geremakis et al. | 623/23.51 |
| 2006/0184246 A1 * | 8/2006 | Zwirkoski | 623/11.11 |
| 2006/0216321 A1 | 9/2006 | Lyu et al. | |
| 2006/0216323 A1 | 9/2006 | Knaack et al. | |
| 2006/0265077 A1 * | 11/2006 | Zwirkoski | 623/17.16 |
| 2006/0287732 A1 | 12/2006 | Pezeshkian | |
| 2007/0043440 A1 * | 2/2007 | William et al. | 623/17.11 |
| 2007/0073401 A1 | 3/2007 | Pointillart et al. | |
| 2007/0093822 A1 * | 4/2007 | Dutoit et al. | 606/61 |
| 2007/0093896 A1 | 4/2007 | Malinin | |
| 2007/0098756 A1 | 5/2007 | Behnam | |
| 2007/0110820 A1 | 5/2007 | Behnam | |
| 2007/0118222 A1 | 5/2007 | Lang | |
| 2007/0125700 A1 | 6/2007 | Ding et al. | |
| 2007/0142916 A1 | 6/2007 | Olson et al. | |
| 2007/0154563 A1 * | 7/2007 | Behnam et al. | 424/549 |
| 2007/0162132 A1 * | 7/2007 | Messerli | 623/17.11 |
| 2007/0178158 A1 | 8/2007 | Knaack et al. | |
| 2007/0231788 A1 | 10/2007 | Behnam et al. | |
| 2008/0027546 A1 | 1/2008 | Semler et al. | |
| 2008/0039586 A1 * | 2/2008 | Hasenwinkel et al. | 525/192 |
| 2008/0051800 A1 * | 2/2008 | Diaz et al. | 606/92 |
| 2008/0069852 A1 | 3/2008 | Shimp et al. | |
| 2008/0091270 A1 | 4/2008 | Miller et al. | |
| 2008/0172058 A1 * | 7/2008 | Trieu et al. | 606/94 |
| 2008/0172131 A1 * | 7/2008 | Trieu et al. | 623/23.73 |
| 2008/0260794 A1 | 10/2008 | Lauritzen et al. | |
| 2008/0305145 A1 * | 12/2008 | Shelby et al. | 424/423 |
| 2009/0024147 A1 * | 1/2009 | Ralph et al. | 606/151 |
| 2009/0069900 A1 * | 3/2009 | Lin et al. | 623/23.48 |
| 2009/0087471 A1 | 4/2009 | Shimp et al. | |
| 2009/0130173 A1 * | 5/2009 | Behnam et al. | 424/426 |
| 2009/0155378 A1 | 6/2009 | Behnam et al. | |
| 2009/0157087 A1 * | 6/2009 | Wei et al. | 606/99 |
| 2009/0187249 A1 * | 7/2009 | Osman | 623/17.16 |
| 2009/0192474 A1 * | 7/2009 | Wei et al. | 604/285 |
| 2009/0220605 A1 | 9/2009 | Wei et al. | |
| 2010/0076497 A1 * | 3/2010 | Zwirkoski | 606/301 |
| 2010/0082073 A1 * | 4/2010 | Thramann | 606/86 R |
| 2010/0121310 A1 * | 5/2010 | Simonton et al. | 604/518 |
| 2010/0145392 A1 * | 6/2010 | Dutoit et al. | 606/279 |
| 2010/0215718 A1 * | 8/2010 | Swords et al. | 424/423 |
| 2011/0015680 A1 * | 1/2011 | Justis et al. | 606/279 |
| 2011/0054408 A1 * | 3/2011 | Wei et al. | 604/175 |
| 2012/0290096 A1 * | 11/2012 | Messerli | 623/17.16 |
| 2013/0189338 A1 * | 7/2013 | Drapeau et al. | 424/402 |
| 2014/0005793 A1 * | 1/2014 | Koford et al. | 623/23.5 |
| 2014/0205674 A1 * | 7/2014 | Wei | 424/549 |
| 2014/0314822 A1 * | 10/2014 | Carter et al. | 424/423 |

FOREIGN PATENT DOCUMENTS

| | | |
|---|---|---|
| EP | 0 082 621 | 6/1983 |
| EP | 0 212 474 | 3/1987 |
| EP | 0 309 241 | 3/1989 |
| EP | 0 148 155 | 4/1989 |
| EP | 0 332 826 A1 | 9/1989 |
| EP | 0 440 991 A1 | 8/1991 |
| EP | 0 567 391 A | 10/1993 |
| EP | 0 603 920 A1 | 6/1994 |
| EP | 0 621 020 A1 | 10/1994 |
| EP | 0 781 564 A2 | 7/1997 |
| JP | 01/179689 | 7/1989 |
| WO | WO 88/00205 | 1/1988 |
| WO | WO 88/01517 | 3/1988 |
| WO | WO 90/03733 | 4/1990 |
| WO | WO 94/21298 | 9/1994 |
| WO | WO 95/31948 | 11/1995 |
| WO | WO 96/39170 | 12/1996 |
| WO | WO 00/13615 | 3/2000 |
| WO | WO 00/45870 | 8/2000 |
| WO | WO 00/47736 | 8/2000 |
| WO | WO 01/28461 A2 | 4/2001 |
| WO | WO 01/70136 A2 | 9/2001 |

(56) References Cited

FOREIGN PATENT DOCUMENTS

| WO | WO 01/79342 A2 | 10/2001 |
|---|---|---|
| WO | WO 02/069818 A2 | 9/2002 |
| WO | WO 03/025271 | 3/2003 |
| WO | WO 03/030956 A3 | 4/2003 |
| WO | WO 2004/073563 A | 9/2004 |
| WO | WO 2005/065396 A2 | 7/2005 |
| WO | WO 2005/072656 A1 | 8/2005 |
| WO | WO 2005/081699 A2 | 9/2005 |
| WO | WO 2006/076712 | 7/2006 |
| WO | WO 2007/053850 | 5/2007 |
| WO | WO 2007/133451 | 11/2007 |

OTHER PUBLICATIONS

Aspenberg P. et al., "Bone morphogenetic protein induces bone in the squirrel monkey, but bone matrix does not", Acta Orthop Scand. 63(6): 619-22 (Dec. 1992).
Blumenthal et al. "The use of collagen membrane barriers in conjunction with combined demineralized bone-collagen gel implants in human infrabony defects," J. Periodontal 61(6): 319-327 (Jun. 1990).
Bravo, D.A. et al., "Accurate and Efficient Cleavage of the Human Insulin Proreceptor by the Human Proprotein-Processing Protease Furin," Journal Biol Chem. 269: 25830-25873 (1994).
Cameron, A. et al., "Polyarginines are potent inhibitors," J. Biol. Chem. 275: 36741-36749 (2000).
Canalis et al., "Bone morphogenetic proteins, their antagonists, and the skeleton," Endocrine Rev. 24(2): 218-235 (2003).
Canalis et al., "Stimulation of DNA and Collagen Synthesis by Autologous Growth Factor in Cultured Fetal Rat Calvaria," Science, 210:1021-1023 (1980).
Caplanis et al., "Effect of allogenic freeze-dried demineralized bone matrix on guided tissue regeneration in dogs," J. Periodontal, 851-856 (Aug. 1998).
Constantino, et al. "Bone Healing and Bone Substitutes," Facial Plastic Surgery 18(1): pp. 14-26 (2002).
Crowe et al., "Inhibition of Enzymatic Digestion of Amylose by Free Fatty Acids in Vitro Contributes to Resistant Starch Formation", J. Nutr., 130(8): 2006-2008 (2000).
Cui et al., "The activity and signaling range of mature BMP-4 is regulated by sequential cleavage at two sites within the prodomain of the precursor," Genes and Development, 15:2797-2802 (2001).
Cui et al., "BMP-4 is proteolytically activated by furin and/or PC6 during vertebrae embryonic development," The Embo Journal, 17(16):4735-4743 (1998).
Deatherage et al., "Packaging and Delivery of Bone Induction Factors in a Collagenous Implant," Collagen Rel. Res. 7:225-231 (1987).
Dubois et al., "Evidence that Furin Is an Authentic Transforming Growth Facto-B-1-Converting Enxyme," American Journal of Pathology, 158(1):305-316 (2001).
Edwards et al., "Osteoinduction of Human Demineralized Bone: Characterization in a Rat Model," Clinical Orthopaedics & Rel. Res., 357: 219-228 (Dec. 1998).
Elliott, J.C., "Structure and Chemistry of the Apatites and Other Calcium Orthophosphates", Elsevier Science B.V., Amsterdam (1994).
Enlow, Donald H., "Principles of Bone Remodeling: An Account of Post-natal Growth and remodeling Processes in Long Bones and the Mandible," Charles C. Thomas, Springfield, Ill., (1963).
Farley et al., "Human Skeletal Growth Factor: Characterization of the Mitogenic Effect on Bone Cells in Vitro," Biochem, 21:3508-3513 (1982).
Flemmig, et al. "Long-Term Maintenance of Alveolar Bone Gain After Implantation of Autolyzed, Antigen-Extracted, Allogenic Bone in Periodontal Intraosseous Defects," J. Periodontal, 69(1): 47-53 (Jan. 1998).
Fujishiro, et al. "Histological evaluation of an impacted bone graft substitute composed of a combination of mineralized and demineralized allograft in a sheep vertebral bone defect," Journal of Biomedical Materials Research Part A, 538-544 (Aug. 4, 2006).

Gamradt, et al. "Bone Graft for Revision Hip Arthroplasty", Clin. Ortho. and Related Research, 417: 183-194 (2003).
Gepstein et al. "Bridging Large Defects in Bone by Demineralized Bone Matrix in the Form of a Powder," The Journal of Bone and Joint Surgery, 69A(7): 984-991 (1987).
Glowacki, "Cellular Reactions to Bone-Derived Material," Clin. Ortho. and Related Research, 324: 47-54 (1996).
Glowacki et al., "Fate of Mineralized and Demineralized Osseous Implants in Cranial Defects," Calcif. Tissue Int., 33: 71-76 (1981).
Glowacki et al., "Demineralized bone implants," Symposium on Horizons in Plastic Surgery, 12(2): 233-41 (1985).
Han B., et al., "Quantitive and sensitive in vitro assay for osteoinductive activity of demineralized bone matrix," J. Orthop. Res. 21(4): 648-54 (Jul. 2003).
Han, C. et al. "Autolysed Antigen-Extracted Allogeneic Boen for Repair of Diaphyseal Boen Defects in Rabbits," Yonsei Medical Journal, 31(3): 251-257 (1990).
Hollinger, et al. "A comparison of four particulate bone derivatives," Clin. Ortho. and Related Research, 267: 255-263 (Jun. 1991).
Hunziker et al., "Repair of Partial Thickness Defects in Articulate Cartilage: Cell Recruitment From the Synovial Membrane", Journal Bone Joint Surg., 78-A: 721-733 (1996).
Iwata et al. "Chemosterilized Autolyzed Antigen-Extracted Allogeneic (AAA) Bone Matrix Gelatin for Repair of Defects from Excision of Benign Bone Tumors," Clin. Ortho and Related Research, 154: 150-155 (1981).
Jain et al., "Anchoring of phospholipase $A_2$: the effect of anions and deuterated water, and the role of N-terminus region," Biochem. Et Biophys. Acta, 860: 448-461 (1986).
Janovec, et al. "Autolyzed Antigen-Extracted Allogeneic Bone for Bridging Segmented Diaphyseal Bone Defects in Rabbits," Clin. Ortho. and Related Research, 229: 249-256 (Apr. 1988).
Jean et al., "Alpha 1-Antitrypsin Portland, a bioengineered serpin highly selective for furin: Application as an antipathogenic agent", Proc. Natl. Acad. Sci., USA 95: 7293-7298 (1998).
Johnson et al. "Human Bone Mortphogenetic Protein Allografting for Reconstruction of Femoral Nonunion," Clin. Ortho. and Related Research, 371: 61-74 (2000).
Johnson et al. "Preliminary explorations of reconstructive surgery with implants of autolyzed antigen-extracted allogeneic (AAA) bone supercharged with bone morphogenetic protein (BMP)," Bone Grafts, Derivatives and Substitutes, published by Butterworth-Heinemann, Oxford, pp. 363-376 (1994).
Johnson et al. "Resistant Nonunions and Partial or Complete Segmental Defects of Long Bones," Clin. Ortho. and Related Research, 277: 229-237 (Apr. 1992).
Kaban et al., "Treatment of Jaw Defects with Demineralized Bone Implants", Journal of Oral and Maxillofacial Surgery, pp. 623-626 (Jun. 6, 1989).
Kasten et al., "Comparison of Human Bone Marrow Stromal Cells Seeded on Calcium-Deficient Hydroxyapatite, Betatricalcium Phosphate and Demineralized Bone Matrix", Biomaterials, 24(15):2593-603 (2003).
Katz, "The Biology of Heavy Water," Scientific American, 106-116 (1960).
Kawai et al., Clin. Orthopaedics and Related Res., 233: 262-267 (1988).
Krysan, D.J., et al., "Quantitative Characterization of Furin Specificity", Journal Biol. Chem. 274, pp. 23229-23234 (1999).
Kubler et al. "Allogenic Bone & Cartilage Morphogenesis," J. Craniomaxillofac. Surg., 19(7):283-288 (1991).
Kubler et al. "Osteoinductive, morphologic, and biomechanical properties of autolyzed, antigen-extracted, allogeneic human bone," J. Oral Maxillofac Surg, 51: 1346-1357 (1993).
Kubler et al. "Repair of human skull defects using osteoinductive bone alloimplants," J. of Cranio Maxillofac. Surg. 23: 337-346 (1995).
Landesman et al, "In Vivo analysis of the half-life of the osteoinductive potential of demineralized bone matrix using diffusion chambers," Calcif. Tissue Int., 45(6): 348-353 (1989).

(56) References Cited

OTHER PUBLICATIONS

Laursen, Malene et al. "Optimal Handling of fresh cancellous bone graft—Different peroperative storing techniques evaluated by in vitro osteobalst-like cell metabolism," *Acta Orthop Scand.*, 74(4): 491 (2003).
Lee et al., *Nature*, 424: 389 (2003).
Lewandrowski et al., "Flexural Rigidity in Partially Demineralized Diaphyseal Bone Grafts", *Clin, Ortho. Rel. Res.*, 317: 254-262 (1995).
Lewandrowski et al. "Improved Osteoinduction of Cortical Bone Allografts: A Study of the Effects of Laser Perforation and Partial Demineralization" *J. Orthop. Res.* vol. 15(5): 748-756 (1997).
Lewandrowski et al. "Kinetics of cortical bone demineralization: Controlled demineralization—a new method for modifying cortical bone allografts", *Journal of Biomedical Materials Research*, vol. 31: 365-372 (1996).
Lewandrowski et al. "Mechanical Properties of Perforated and Partially Demineralized Bone Grafts," *Clin. Ortho. and Related Research*, 353: 238-246 (1998).
Lewandrowski et al., "An Electron Microscopic Study on the Process of Acid Demineralization of Cortical Bone," *Calcified Tissue Int.* 61:294-297 (1997).
Lieberman, et al. "Treatment of Osteonecrosis of the Femoral Head with Core Decompression and Human Bone Morphogenetic Protein," *Clin. Ortho. and Related Research*, 429: 139-145 (2004).
Lotz, *Clin. Orthopaedics and Related Res.*, 391S: S108-S115 (2001).
Mellonig, James. "Bone Allografts in Periodontal Therapy," *Clin. Ortho. and Related Research*, 324: 116-125 (1996).
Mellonig, J.T. "Decalcified freeze-dried bone allograft as an implant material in human periodontal defects," *The Int'l Journal of Periodontics and Restorative Dentistry* 4(6): 40-55 (1984).
Miloslav et al., "Autolyzed antigen-extracted allogeneic bone for bridging segmented diaphyseal bone defects in rabbits," *Clinical Orthopaedics and Related Research*, 229: 249-256 (Apr. 1988).
Nade et al. "Decalcified Bone as a Substrate for Osteogenesis," *Bone Joint Surg.* 59(2): 189-1996 (1977).
Neigel et al. "Use of Demineralized Bone Implants in Orbital and Craniofacial Reconstruction and Review of the Literature," *Opthal. Plast. Reconst. Surg.*, 12:108 (1996).
Nogami et al., "Sustrata Prepared from Bone Matrix for Chondrogenesis in Tissue Culture", *The Journal of Cell Biology*, 62: 510-519 (1974).
Nogami et al., "Transmembrane Bone Matrix Gelatin-Induced Differentiation of Bone", *Calcif. Tiss. Res.*, 19: 153-163 (1975).
Oberg et al. "Bone formation after implantation of autolysed antigen extracted allogeneic bone in ovariectomized rabbits," *Int. J. Oral Maxillofac. Surg.* 32: 628-632 (2003).
Oberg et al. "Bone healing after implantation of hydroxyapatite granules and blocks (Interpore 200) combined with autolyzed antigen-extracted allogeneic bone and fibrin glue," *Int. J. Oral. Maxillofac. Surg.* 23: 110-114 (1994).
"Organic Reactions", vols. 1-40, John Wiley and Sons, New York, NY (1991).
Ousterhout. "Clinical Experience in Cranial and Facial Reconstruction with Demineralized Bone," *Ann. Plast. Surg.* 15(5): 367-373 (1995).
Paralkar et al., "An EP2 receptor-selective prostaglandin $E_2$ agonist induces bone healing," *PNAS*, 100(11): 6736-6740 (2003).
Peel SA et al., "In search of the ideal bone morphogenetic protein delivery system: in vitro studies on demineralized bone matrix, purified, and recombinant bone morphogenetic protein", *J. Craniofac. Surg.*, 14(3): 284-91 (May 2003).
Ray et al., "Bone Implants," *J. Bone Joint Surgery*, 39A(5): 1119-1128 (1957).
Reddi et al., "Biochemical Sequences in the Transformation of Normal Fibroblasts in Adolescent Rats," *Proc. Natl. Acad. Sci. USA*, 69(6): 1601-1605 (1972).
Ripamonti et al. "Bone induction in a composite allogeneic bone/alloplastic implant," *J. Oral Maxillofac. Surg.* 47: 963-969 (1989).

Ripamonti et al. "The induction of bone in osteogenic composites of bone matrix and porous hydroxyapatite replicas: Experimental study on the baboon," *Oral Maxillofac. Surg.* 9: 817-830 (1991).
Ripamonti. "Bone induction in nonhuman primates: an experimental study on the baboon," *Clin. Ortho. and Related Research*, 269: 284-294 (Aug. 1991).
Ripamonti. "Calvarial regeneration in primates with autolyzed antigen-extracted allogeneic bone," *Clin. Ortho. and Related Research*, 282: 293-303 (Sep. 1992).
Rodd, "Chemistry of Carbon Compounds", vols. 1-5 and supplementals, Elsevier Science Publishers, Amsterdan (1989).
Ronningen et al. "Bone formation enhanced by induction," *Acta Orthop Scan* 56: 67-71 (1985).
Ronningen et al. "Osteogenesis promoted by bone matrix combined with marrow," *Acta Orthop Scand* 5Z: 15-18 (1986).
Rosenquist et al. "Effects of bone grafting on maxillary bone healing in the growing pig," *J. Oral Maxillofac. Surg.* 40: 566-569 (1982).
Rosenthal et al. "Demineralized bone implants for nonunion fractures, bone cysts, and fibrous lesions," *Clin. Ortho. and Related Research* 362: 61-69 (1999).
Russell et al., "Clinical Utility of Demineralized Bone Matrix for Osseous Defects, Arthrodesis, and Reconstruction; Impact of Processing Techniques and Study Methodology," *Orthopaedics*, 22(5): 524-531 (May 1999).
Sailer et al. "Application of purified bone morphogenetic protein (BMP) in cranio-maxillo-facial surgery," *Jour. of Cranio-Maxillo-Facial Surgery* 22: 2-11 (1994).
Sambrook, et al. Molecular Cloning: A Laboratory Manual, $3^{rd}$ ed., Cold Spring Harbor Laboratory Press, Cold Spring Harbor (2001).
Sampath and Reddi, "Homology of bone-inductive proteins from human, monkey, bovine, and rat extracellular matrix," *Proc. Nat. Acad. Sci.* 80:6591-6594 (1983).
Sampath et al., "Bovine osteogenic protein is composed of dimmers of OP-1 and BMP-2A, Two members of the transforming growth factor-beta superfamily,"*J. Biol. Chem.*, 5:265(22): pp. 13198-13205 (Aug. 1990).
Sampath et al., "Isolation of osteogenin, an extracellular matrix-associated, bone-inductive protein, by heparin affinity chromatography," *Proc. Natl. Acad. Sci.* 84(7): 7109-7113 (1987).
Schmid et al. "Osteoinduction in tibial defects in the dog," *Unfallchirurgie* 19: 1-8 (1993).
Schwarz et al., "Dog bone less osteogenetic than rat bone," *Acta. Orthop. Scan.* 60(6): 693-695 (1989).
Schwarz et al. "Decalcified and undecalcified cancellous bone block implants do not heal diaphyseal defects in dogs," *Arch. Orthop. Trauma Surg.* 111:47-50 (1991).
Serini et al., "Class 3 semaphorins control vascular morphogenesis by inhibiting integrin function," *Nature*, 424:391-397 (Jul. 2003).
Smith, Michael et al. "March's Advanced Organic Chemistry", $5^{th}$ edition, John Wiley and Sons, New York, NY (Mar. 2001).
Steadman et al., "Microfracture: Surgical Technique and Rehabilitation to Treat Chondral Defects", *Clin. Orthop.*, 391 S:362-369 (2001).
Steiner, D.F., "The proprotein convertases," *Curr. Opinion Chem. Biol.* 2: 31-39 (1998).
Temenoff et al., "Effect of poly(ethylene glycol) molecular weight on tensile and swelling properties of oligo(poly(ethylene glycol) fumarate) hydrogels for cartilage tissue engineering", *OPF Hydrogel Material Properties*, John Wiley & Sons, Inc., pp. 429-437 (2001).
Terashima et al., Chondrogenesis in Outgrowths of Muscle Tissue onto Modified Bone Matrix in Tissue Culture, *Clinical Orthopaedics and Related Research*, 127: 248-256 (Sep. 1977).
Todescan et al., "A Small Animal Model for Investigating Endosseous Dental Implants: Effect of Graft Materials on healing of Endoss, Porous-Surfaced Implants Placed in a Fresh Extraction Socket," *The Journal of Oral and Maxillofacial Implants*, 2(2): 217-223 (1987).
Toriumi et al. "Demineralized Bone," Arch Otolaryngol Head Neck Surg. 116: 676-680 (Jun. 1990).
Ueland et al., *J. Clin. Endocrinol. & Metab.*, 84(1): 123-127 (1999).
Urist. "Bone: Formation by Autoinduction," *Science*, 150(698): pp. 893-899 (1965).

(56) References Cited

OTHER PUBLICATIONS

Urist. "The Bone Induction Principle," *Clin. Ortho. Rel. Res.*, 55: 243-283 (1967).
Urist et al., "Bone morphogenesis in Implants of Insoluble Bone Gelatin," *Proc. Natl. Acad. Sci.*, 70(12): 3511-5 (Dec. 1973).
Urist et al., ., "Preservation and biodegradation of the morphogenetic property of bone matrix," *J. Theor. Biol.* 38: 155-67 (1973).
Urist et al., "Observations implicating an extracellular enzymic mechanism of control of bone morphogenesis," *J. Histochem & Cytochem*, 22(2): 88-103 (1974).
Urist et al., "A Chemosterilized Antigen-Extracted Autodigested Alloimplant for Bone Banks," *Arch Surg.* vol. 110: 416-428 (Apr. 1975).
Urist et al., "Cartilage Tissue Differentiation from Mesenchymal Cells Derived from Mature Muscle in Tissue Culture", *In Vitro*, 14(8): 697-706 (1978).
Urist et al. "Intertransverse Process Fusion with the Aid of Chemosterilized Autolyzed Antigen-Extracted Allogeneic (AAA) Bone," *Clin. Ortho. and Related Research*, 154: 97-113 (1981).
Urist et al., "Human Bone Morphogenetic Protein (hBMP)," *Proc. Soc. Exp. Biol.* 173:194-199 (1983).
Urist et al., "Purification of bovine bone morphogenetic protein by hydroxyapatite chromatography," *Prop. Natl. Acad. Sci.* 81:371-375 (1984).
Van den Berg et al., "Tissue Engineering, Cells, Scaffolds, and Growth Factors," *Clin. Orthopaedics and Related Res.*, 391S: S244-S250 (2001).
Van den Ouweland, A.M.W. et al., "Structural homology between the human *fur* gene product and the subtilisin-like protease encoded by yeast *KEX2*," *Nucl. Acid Res.* 18(3): 664 (1990).
Wang et al., "Purification and characterization of other distinct bone-inducing factors," *Proc. Nat. Acad. Sci.* 85:9484-9488 (1988).
Wang et al., "Recombinant human bone morphogenetic protein induces bone formation," *Proc. Nat. Acad. Sci.* 87:2220-2224 (1990).
White et al., "Effective terminal sterilization using supercritical carbon dioxide," *Journal of Biotechnology*, 123: 504-515 (2006).
Whiteman et al., "Demineralized Bone Powder," *J. Hand. Surg.*, 18B(4): 487-90 (1993).
Wise, D.L., "Encyclopedia Handbook of Biomaterials and Bioengineering Part B", Applications New York: Marcel Decker (1995).
Xiaobo, H., et al., "Experimental and Clinical Investigations of Human Insoluble Bone Matrix Gelatin," *Clin. Orthopaedics and Related Research*, vol. 293: 360-365 (1993).
Young et al. "Morphological changes of autoclaved autogenic bone implantation and autoclaved autogenic bone supplemented with allogenic demineralized bone matrix in rat parietal bone," *Histol Histopathol.* 11: 361-369 (1996).
Zhang et al., "A Quantitative assessment of osteoinductivity of human demineralized bone matrix," *J. Periodontal*, 68(11): 1076-84 (Nov. 1997).
Ou, Wenbin et al. "Effects of Glycerol in the Refolding and Unfolding of Creatine Kinase," *Tsinghua Science and Technology*, 7(4): 352-367 (Aug. 2002).
Ou, Wenbin et al. "Molecular Mechanism for Osmolyte Protection of Creatine Kinase Against Guanidine Denaturation," *Eur. J. Biochem.*, 268: 5901-5911 (2001).

\* cited by examiner

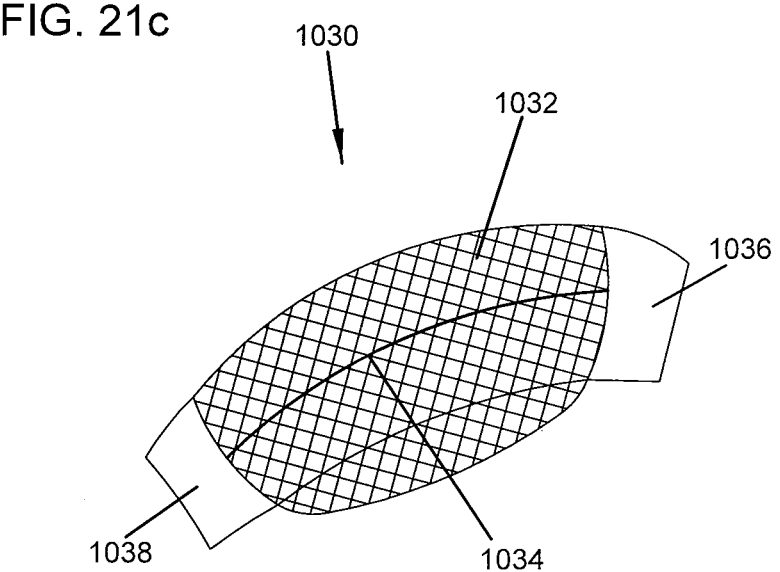

1400

1406
1408
1404
1402

SEGMENTED DELIVERY SYSTEM

CROSS REFERENCE TO RELATED APPLICATIONS

This application claims benefit under 35 U.S.C. §119(e) of priority to U.S. Provisional Application No. 61/152,057 filed Feb. 12, 2009, U.S. Provisional Application No. 61/154,673 filed Feb. 23, 2009, U.S. Provisional Application No. 61/154,689 filed Feb. 23, 2009, and U.S. Provisional Application No. 61/154,679 filed Feb. 23, 2009, the contents of all of which are hereby incorporated in their entirety by reference.

FIELD

A delivery system for delivering a substance or material to a surgical site is provided. More particularly, a delivery system comprising a covering and a substance, the covering being configured for at least partially retaining the substance provided therein until the delivery system is placed at a surgical site, and thereafter facilitating transfer of the substance or surrounding materials, is provided.

BACKGROUND

The use of bone grafts and bone substitute materials in orthopedic medicine is known. While bone wounds can regenerate without the formation of scar tissue, fractures and other orthopedic injuries take a long time to heal, during which time the bone is unable to support physiologic loading unaided. Metal pins, screws, rods, plates and meshes are frequently required to replace the mechanical functions of injured bone. However, metal is significantly more stiff than bone. Use of metal implants may result in decreased bone density around the implant site due to stress shielding. Physiologic stresses and corrosion may cause metal implants to fracture. Unlike bone, which can heal small damage cracks through remodeling to prevent more extensive damage and failure, damaged metal implants can only be replaced or removed. The natural cellular healing and remodeling mechanisms of the body coordinate removal of bone and bone grafts by osteoclast cells and formation of bone by osteoblast cells.

Conventionally, bone tissue regeneration is achieved by filling a bone repair site with a bone graft. Over time, the bone graft is incorporated by the host and new bone remodels the bone graft. In order to place the bone graft, it is common to use a monolithic bone graft or to form an osteoimplant comprising particulated bone in a carrier. The carrier is thus chosen to be biocompatible, to be resorbable, and to have release characteristics such that the bone graft is accessible. Generally, the formed implant, whether monolithic or particulated and in a carrier, is substantially solid at the time of implantation and thus does not conform to the implant site. Further, the implant is substantially complete at the time of implantation and thus provides little ability for customization, for example by the addition of autograft.

The use of bone grafts is generally limited by the available shape and size of grafts. Bone grafts using cortical bone remodel slowly because of their limited porosity. Traditional bone substitute materials and bone chips are more quickly remodeled but cannot immediately provide mechanical support. In addition, while bone substitute materials and bone chips can be used to fill oddly shaped bone defects, such materials are not as well suited for wrapping or resurfacing bone.

Thus, it would be useful to provide a delivery system for delivering a substance, such as bone graft, to a surgical site that conforms to the surgical site, that maintains a substance provided therein in a coherent mass, and that can be customized at the time of implantation.

SUMMARY

A delivery system for delivering a substance or material to a surgical site is provided. The delivery system comprises a covering and a substance to be retained within and delivered by the covering. Generally, the covering may be a single or multi-compartment structure capable of at least partially retaining a substance provided therein until the covering is placed at a surgical site. In some examples, upon placement, the covering facilitates transfer of the substance and/or materials from the covering to the surgical site. The covering may participate in, control, or otherwise adjust, the release of the substance or penetration of the covering by surrounding materials, such as cells or tissues.

In accordance with another embodiment, a delivery system comprising a plurality of operably linked segments of at least two types is provided. The first segment type of the delivery system comprises a covering material defining at least one compartment containing a bone growth substance, and the second segment type is configured to connect segments of the first type. In further embodiments of the delivery system, each of the first segment types contain the same or different amounts and/or types of bone growth substance. In some embodiments, the segments of the first type vary in size and/or covering material. In still further embodiments, the second segment type is also made of a covering material that is unfilled or partially filled with a bone repair substance.

In accordance with another embodiment, a delivery system comprising linked segments of at least two types, the delivery system is designed for use in a sternum closure procedure, or filling an irregular shaped bone void is provided. When used to fill an irregular void, many embodiments of the delivery system include at least two segments of the first type within the bone void packed substantially in parallel. In still further embodiments, the delivery system is terminally sterilized, for example by gamma radiation, electron beam radiation, UV irradiation, cobalt source radiation; autoclaving, dry heating, EtO, EtOH, and by supercritical fluid exposure. In still other embodiments, the bone growth substance is sterilized by a method other than that used to sterilize the covering material.

In accordance with another embodiment, a delivery system that comprises bone growth substance contained within a covering material is provided. The volume of the bone growth substance is less than the maximum volume of the compartment. The covering material containing the bone growth substance is configured to fit an irregular bone void. The covering material and bone growth substance therein is manipulated to fit an irregular void. In some embodiments, the bone repair substance and covering material in excess of that needed to substantially fill the irregular void is removed and discarded. In some embodiments, the delivery system is used in a surgical procedure, for example a discectomy.

In accordance with another embodiment, a tool for grasping and placing a delivery system near a bone is provided. The tool comprises a handle connected to a docking port, and a plunger. The docking port is configured to attach to a rigid structure attached to a bone repair delivery system. The plunger is disposed in the handle and configured to push and release the rigid structure into a bone location.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description is to be regarded as illustrative in nature and not restrictive.

BRIEF DESCRIPTION

FIG. 1b illustrates an alternative view of the delivery system of FIG. 1a.

FIG. 2b illustrates an alternative view of the delivery system of FIG. 2a.

FIG. 5b illustrates a top view of the covering of FIG. 5a.

FIG. 5c illustrates an end cross-sectional view of the covering of FIG. 5a.

FIG. 6b illustrates a top view of the covering of FIG. 6a.

FIG. 6c illustrates an end cross-sectional view of the covering of FIG. 6a.

FIG. 7b illustrates a top view of the covering of FIG. 7a.

FIG. 7c illustrates an end cross-sectional view of the covering of FIG. 7a.

FIG. 21c illustrates an embodiment of a curved covering with a shaping or reinforcing structure, in accordance with one embodiment.

DEFINITIONS

Figure 1A:
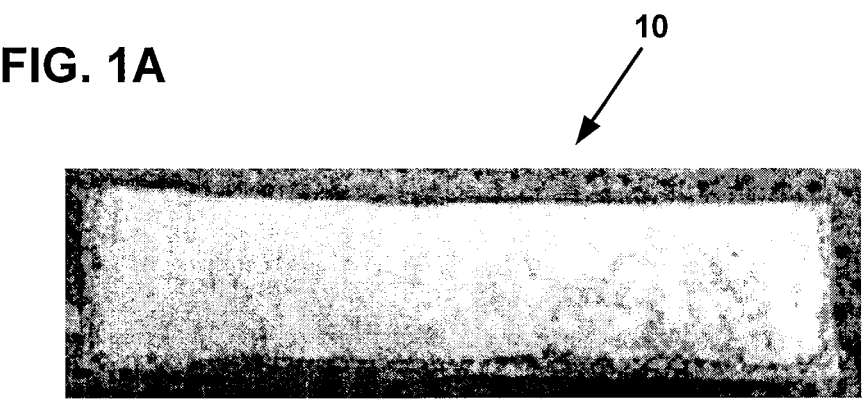
FIG. 1a illustrates a delivery system comprising a relatively narrow tubular covering and a particulated substance, in accordance with one embodiment.

Bioactive Agent or Bioactive Compound, as used herein, refers to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. In some embodiments, the bioactive agent is a growth factor, cytokine, extracellular matrix molecule or a fragment or derivative thereof, for example, a cell attachment sequence such as RGD. A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996; and the United States Pharmacopeia-25/National Formulary-20, published by the United States Pharmacopeial Convention, Inc., Rockville Md., 2001, each of which is incorporated herein by reference.

Biocompatible, as used herein, refers to materials that, upon administration in vivo, do not induce undesirable long-term effects.

Bone, as used herein, refers to bone that is cortical, cancellous or cortico-cancellous of autogenous, allogenic, xenogenic, or transgenic origin.

Demineralized, as used herein, refers to any material generated by removing mineral material from tissue, e.g., bone tissue. In certain embodiments, the demineralized compositions described herein include preparations containing less than 5% calcium and preferably less than 1% calcium by weight. Partially demineralized bone (e.g., preparations with greater than 5% calcium by weight but containing less than 100% of the original starting amount of calcium) is also considered within the scope of the invention. In some embodiments, demineralized bone has less than 95% of its original mineral content. Demineralized is intended to encompass such expressions as "substantially demineralized," "partially demineralized," and "fully demineralized."

Demineralized bone matrix, as used herein, refers to any material generated by removing mineral material from bone tissue. In preferred embodiments, the DBM compositions as used herein include preparations containing less than 5% calcium and preferably less than 1% calcium by weight. Partially demineralized bone (e.g., preparations with greater than 5% calcium by weight but containing less than 100% of the original starting amount of calcium) are also considered within the scope of the invention.

Osteoconductive, as used herein, refers to the ability of a non-osteoinductive substance to serve as a suitable template or substance along which bone may grow.

Osteogenic, as used herein, refers to the ability of an agent, material, or implant to enhance or accelerate the growth of new bone tissue by one or more mechanisms such as osteogenesis, osteoconduction, and/or osteoinduction.

Osteoimplant, as used herein, refers to any bone-derived implant prepared in accordance with the embodiments of this invention and therefore is intended to include expressions such as bone membrane, bone graft, etc.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," *Clinical Orthopaedics & Rel. Res.,* 357:219-228, December 1998, incorporated herein by reference.

Superficially demineralized, as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

DETAILED DESCRIPTION

I. Introduction

A delivery system for delivering a substance or material to a surgical site is provided. In various embodiments, the delivery system comprises a covering and a substance for delivery by the covering. The covering provides superior containment of the substance, such as graft material, which helps focus and concentrate materials that provide healing at the surgical site. In some embodiments, the covering also helps the surgeon perform less invasive procedures, by delivering a contained unit of grafting material to the surgical site.

The delivery system may be used to treat a wide variety of bone or soft tissue defects including surgically created or pre-existing (such as by trauma) defects. In some embodiments, the delivery system may be used to treat contained bony voids or contained defects. Such bony voids are voids or cavities that have a cortical shell on three sides. In some embodiments, the delivery system may be used to treat critical defects. Generally, critical defects are defects that will not heal spontaneously and must be grafted in order to assure healing. In some embodiments, the delivery system may be used to treat segmental defects. Segmental defects are defects in the cortical shaft of a long bone in which a segment is missing. In some embodiments, the delivery system may be used to treat contained or non-critical defects wherein the delivery system may act as a plug to assist healing. Other applications for the delivery system are discussed herein and none are intended to be limiting.

The delivery system comprises a covering and a substance wherein the substance is provided within the covering for delivery to the surgical site. The delivery system provides increased handling properties, ability to place grafting material reliably using minimally invasive procedures, and improved delivery characteristics such as graft retention compared with other systems. In some embodiments, upon placement, the covering facilitates transfer of the substance and/or materials to the surgical site. In some embodiments, for example wherein the covering holds graft materials, the covering substantially prevents graft migration. The covering may participate in, control, or otherwise adjust, the release of the substance from the covering or penetration of the covering by surrounding materials, such as cells or tissues.

Generally, the covering may be a single or multi-compartment structure capable of at least partially retaining a substance provided therein until the covering is placed at a surgical site. In some embodiments, the covering may be substantially non-expandable or minimally deformable. In some embodiments, the covering may be a temporary covering wherein the covering is substantially resorbable. For example, in some embodiments, the covering may be formed of a material that is substantially resorbed within 2 weeks, within 4 weeks, within 12 weeks, or within other suitable time frame. Accordingly, in some embodiments a delivery system including the covering may be a temporary delivery system. The covering may include one or more attachment mechanisms for retaining the covering at the surgical site. The attachment mechanism may be a mechanical attachment mechanism, a physical attachment mechanism, a biological attachment mechanism or a chemical attachment mechanism, or may employ combinations of these. The attachment mechanism may be used to attach the covering to skeletal or soft tissue proximate the surgical site.

In some embodiments, the covering may be used for containment of particulate or morselized materials (the substance provided in the covering), optionally to provide a focus or concentration of biological activity. In some embodiments, the covering may be used for containment of a substance one or more of bone particles, bone fibers, other osteoinductive or osteoconductive materials, BMP, antibiotics, or other materials.

In some embodiments, the covering may be used for maintaining materials (the substance provided in the covering) in spatial proximity to one another, possibly to provide a synergistic effect. In some embodiments, the covering may be used to control availability of a substances provided within the covering to cells and tissues of a surgical site over time. In some embodiments, the covering may be used for delivery through a limited opening, such as in minimally invasive surgery or mini-open access. In some embodiments, the covering may be used to deliver morselized or particulated materials (the substance provided in the covering) in pre-measured amounts. In other embodiments, the substance may be liquid or flowable, or combinations of these with particulate, morselized, and/or other materials.

In various embodiments, the covering may contain a substance or material such as a graft material. The covering limits, and in some embodiments eliminates, graft migration and maintains graft density. The delivery system, with contained substance or material, may be configured to conform to surrounding bony contours or implant space. In some embodiments, the delivery system provides a pathway for healing/cell penetration and tissue ingrowth. Thus, the covering may facilitate transfer or diffusion of materials into and out of the covering. For example, the covering may facilitate diffusion from the covering of a substance provided within the covering or may facilitate diffusion into the covering of materials in the surgical site, such as cells and tissues, into the covering. The covering may be configured to permit diffusion of some materials while substantially preventing diffusion of other materials. Further, in various embodiments, the covering may be configured such that diffusion is permitted into or out of certain portions of the covering but not other portions of the covering. In some embodiments, the covering may merely retain a substance at the surgical site.

The covering may have a single compartment or may have a plurality of compartments. Thus, in one embodiment, the covering is dual-compartment and comprises first and second compartments. A first substance may be provided in the first compartment and a second substance may be provided in the second compartment. The second compartment may be adjacent to, apart from, inside, or surrounding the first compartment. Materials forming the first compartment and the second compartment may be the same or may be different. Selection of materials, positioning of the compartments, and other factors relating to the first and second compartments may be chosen to achieve simultaneous or sequential delivery or release of a substance or substances.

II. Covering Material

The covering may comprise a structural material and, in some embodiments, a functional material. The structural material may comprise a mesh material, a polymeric material, a substantially solid material, or other. The functional material may comprise, for example, a radiopaque material, a bacteriocidal material, or other.

Structural Material Characteristics

In various embodiments, in accordance with the specific application for which the covering is being used, the covering may be rigid, may be flexible, may be non-elastic, or may be elastic. The covering material may be braided, woven, non-woven shape memory, particulate, threaded, porous, non-porous, or substantially solid. While the term "structural" is used to describe the material forming the main structure of the covering, it is to be appreciated that this is not intended to imply that the covering need have structural or load-bearing characteristics.

The covering may participate in, control, facilitate, prevent, or otherwise adjust the release of the substance. For example, the covering may act as a selectively permeable membrane and/or may be porous, with the level of porosity being related to the nature of the substances inside the covering. Thus, the material for and configuration of the covering may be selected or adjusted based on desired release characteristics. Specific properties of the structural material that may be adjusted include thickness, permeability, porosity, strength, flexibility, elasticity, and others. It is to be appreciated that some of these properties may depend on others. For example, the thickness and porosity of the material may contribute to its strength, flexibility, and elasticity. In some embodiments, the covering may be made of a squishy, moldable, sticky, and/or tacky material to facilitate placement and packing of the covering.

In some embodiments, the covering may be porous to fluid and/or cells, may be biocompatible, and may be resistant to rupture (including should the substance provided therein swell). In some embodiments, the covering with the substance provided therein may be load-bearing. The covering may be resorbable or non-resorbable. The covering may provide increased handling properties, may have irrigation resistance, may have material retention characteristics, and/or may support cellular penetration. Flexibility of the covering may be selected to suit particular applications. In some applications, it may be desirable to have a flexible covering.

If the covering is made from a resorbable material, the covering degrades and disappears after a period of time. The covering thus may be considered a temporary covering. If the covering is not made of a resorbable material, the covering remains in the body. Tissue ingrowth may occur to bind the host tissue to the substance provided within the covering. Tissue ingrowth through and around the covering, between the host tissue and the substance provided within the covering, may be promoted via openings in the covering.

In various embodiments, the covering may comprise a porous material or a mesh material. The size of the pores of the covering may be designed to permit cellular infiltration (approximately several microns to several millimeters), but may also be designed specifically to exclude cells from the inside of the covering (e.g. approximately 0.45 microns) and only allow diffusion of small molecules (proteins and hormones). Thus, the covering may act to control access to the interior of the delivery system by cells. U.S. Patent Application Publication No. 2005/0283255; for Tissue-Derived Mesh for Orthopedic Regeneration describes suitable manners for forming a mesh for use with a covering as provided herein and is herein incorporated by reference in its entirety.

The covering may be formed of a resorbable or nonresorbable, natural or synthetic, biocompatible material. In some embodiments, more than one material may be used, including as multiple layers. For example, in an embodiment comprising two compartments, one or more materials may be used for the first compartment and a different material or materials may be used for the second compartment. For example, one compartment or portions thereof may be made of material or materials that provide a desired property or properties relative to other compartments or portions thereof, such as increased or decreased resorbability or stiffness, or the different compartments or portions thereof may be imparted with different drug delivery properties, etc. Alternatively, all compartments may comprise the same material or mixtures of materials. Where the characteristics of the material are varied between compartments, or over the surface of a single compartment, the pores of the first compartment or portion thereof may be larger than the pores of the second compartment.

The covering may comprise any suitable structure for delivering a substance in vivo. Thus, as described, the covering may comprise a mesh. In other embodiments, the covering may comprise a polymeric structure with a chamber provided therein. The chamber may be filled with a substance for delivering in vivo, such as autograft, demineralized bone matrix, or others disclosed herein.

In embodiments comprising more than one compartment, characteristics of the covering material may be varied between compartments. Generally, the porosity, flexibility, strength, or any other characteristic of one compartment may vary from that characteristic of the other compartment. Further, characteristics of the covering may vary at different positions of the covering regardless of compartmental configuration of the covering.

In some embodiments, the covering may expand when placed in the body. Expansion can be provided in at least two ways: the covering may be compressed such that the covering expands when placed in the body or the covering may be made of a material that expands when it comes in contact with water or other bodily fluids, either by way of liquid absorption, or by stretching when the materials inside it absorb liquid and themselves expand. In some embodiments, the covering may comprise a shape memory material such as copper-zinc aluminum-nickel alloy, copper-aluminum-nickel alloy, and nickel-titanium (NiTi) alloy. Reinforcing materials such as cortical bone, calcium phosphates, etc. may be incorporated into the structure of the covering to reinforce it. In other embodiments, the covering may be substantially non-expandable or minimally deformable.

The covering may be configured for specific compressive strength and rigidity by adjusting density and resorption time of the covering. In some embodiments, a coating may be provided over the covering. For example, the coating may be a compound of poly-L-lactide, of polyglycolic acid, or their polymers, or polyhydroxyalkanoates (polyhydroxybutyrates and polyhydroxyvalerates and copolymers). The coating may be selected such that it has a resorption time wherein it is resorbed by the body and the material within the covering is permitted to exit through openings in the covering.

Exemplary Covering Materials

Polymeric material (for example, see U.S. Pat. Nos. 6,696,073, 6,478,825, 6,440,444, and 6,294,187 and U.S. Patent Publications Nos. 2006/0216323 and 2005/0251267, all herein incorporated by reference in their entirety); woven material and braided material (for example, see U.S. Patent Publication No. 2005/0283255, herein incorporated by reference in its entirety); non-woven materials; shape memory material; porous materials; and non-porous materials may be used. In some embodiments, outer particles may be used to contain inner particles; particles may be attached to threads of material, and/or porosity may be added to mesh fibers. In some embodiments, materials may be used for portions of the covering, such as for a compartment of the covering, that are substantially impenetrable.

In some embodiments, the covering may comprise a mesh material. Suitable mesh materials include natural materials, synthetic polymeric resorbable materials, synthetic polymeric non-resorbable materials, and other materials. Natural mesh materials include silk, extracellular matrix (such as DBM, collagen, ligament, tendon tissue, or other), silk-elastin, elastin, collagen, and cellulose. Synthetic polymeric resorbable materials include poly(lactic acid) (PLA), poly (glycolic acid) (PGA), poly(lactic acid-glycolic acid) (PLGA), polydioxanone, PVA, polyurethanes, polycarbonates, polyhydroxyalkanoates (polyhydroxybutyrates and polyhydroxyvalerates and copolymers), polysaccharides, polyhydroxyalkanoates polyglycolide-co-caprolactone, polyethylene oxide, polypropylene oxide, polyglycolide-co-trimethylene carbonate, poly(lactic-co-glycolic acid), and others. See Chen and Wu, "The Application of Tissue Engineering Materials," Biomaterials, 2005, 26(33): p. 6565-78, herein incorporated by reference in its entirety. Other suitable materials include carbon fiber, metal fiber, polyertheretherketones, non-resorbable polyurethanes, polyethers of all types, polyethylene terephthalte, polyethylene, polypropylene, Teflon, and various other meshes. In other embodiments, the covering may comprise non-woven material such as spun cocoon or shape memory materials having a coil shape or shape memory alloys. Alternatively, any of these materials may be used in a non-mesh form.

Generally, the covering may be formed of any natural or synthetic structure (tissue, protein, carbohydrate) that can be used to form a covering configuration. Thus, the covering may be formed of a polymer (such as polyalkylenes (e.g., polyethylenes, polypropylenes, etc.), polyamides, polyesters, poly(glaxanone), poly(orthoesters), poly(pyrolicacid), poly (phosphazenes), polycarbonate, other bioabsorbable polymer such as Dacron or other known surgical plastics, a natural biologically derived material such as collagen, gelatin, chitosan, alginate, a ceramic (with bone-growth enhancers, hydroxyapatite, etc.), PEEK (polyether-etherketone), dessicated biodegradable material, metal, composite materials, a biocompatible textile (e.g., cotton, silk, linen), extracellular matrix components, tissues, or composites of synthetic and natural materials, or other. Various collagen materials can be used, alone or in combination with other materials, including collagen sutures and threads. Any suitable collagen material may be used, including known collagen materials, or collagen materials as disclosed in U.S. patent application Ser. No. 12/030,188, filed Feb. 12, 2008, hereby incorporated by reference in its entirety, which discloses collagen materials that may be used for forming a covering. Some examples include polymer or collagen threads woven, or knitted, into a mesh. Other suitable materials include thin polymer sheets molded in the presence of a porogen and having underwent leaching; polymer sheets or naturally derived sheets such as fascia and other collagen materials, small intestinal submucosa, or urinary bladder epithelium, the sheets being punctured to introduce porosity; specific shapes printed using available or future printing technologies; naturally secreted materials such as bacterial cellulose grown within specific molds; etc.

In some embodiments, mesh fibers may be treated to impart porosity to the fibers. This may be done, for example, to PLA, PLGA, PGA, and other fibers. One suitable method for treating the mesh fibers comprises supercritical carbon dioxide treatment to partially solubilize the particles. This treatment may further be carried out for viral inactivation. Another suitable method for treating the mesh fibers comprises explosive decompression. Explosive decompression generates porosity and leads to controlled permeability. The mesh material further may be loaded with cells, growth factors, or bioactive agents.

In further embodiments, fibers of a mesh material may be treated such as by having particles adhered thereto. The particles may be, for example, bone particles. Thus, in one embodiment, the covering may comprise a plurality of threads formed into a fabric. The threads may have particles adhered thereto. For example, the threads may have particles strung on the thread. In an alternative embodiment, the covering may be formed of a material and the material may be coated with particles.

In yet other embodiments, the covering may comprise a non-porous material, which may be permeable. A non-porous material may be used for later (or delayed) delivery of a substance provided therein. Such substance may comprise, for example, cells, growth factors, or bone morphogenetic proteins. Accordingly, in one embodiment, a delivery system for delayed delivery of cells, growth factors, or bone morphogenetic proteins is provided comprising a non-porous covering.

While certain embodiments are described with respect to having mesh characteristics, it is to be appreciated that not all embodiments may have such mesh characteristics. Further, the material used for the covering and its characteristics may be selected for specific applications. For example, in some embodiments, the covering may be formed of a resorbable material, such as formed as a resorbable container or capsule. Such resorbable material may be useful in delivering, for example, antibiotic to a site by an outer resorbable material, and then gradually exposing inner graft material after the infection is cleared. In such embodiments, the delivery system comprises a temporary delivery system.

Functional Material Characteristics

The covering material may have functional characteristics. Alternatively, other materials having functional characteristics may be incorporated into the covering. Functional characteristics may include radiopacity, bacteriocidity, source for released materials, tackiness, etc. Such characteristics may be imparted substantially throughout the covering or at only certain positions or portions of the covering.

Suitable radiopaque materials include, for example, ceramics, mineralized bone, ceramics/calcium phosphates/calcium sulfates, metal particles, fibers, and iodinated polymer (see, for example, WO/2007/143698). Polymeric materials may be used to form the covering and be made radiopaque by iodinating them, such as taught for example at (http://www.teamreva.com/tech_bioresorbable.html and http://www.teamreva.com/company_news_xray.html and U.S. Pat. No. 6,585,755, herein incorporated by reference in its entirety. Other techniques for incorporating a biocompatible metal or metal salt into a polymer to increase radiopacity of the polymer may also be used. Suitable bacteriocidal materials may include, for example, trace metallic elements. In some embodiments, trace metallic elements may also encourage bone growth.

Functional material, such as radiopaque markers, may be provided at one or more locations on the covering or may be provided substantially throughout the covering. Thus, for example, in a tubular covering, a radiopaque marker may be provided at a tip of the tubular covering. Such marker may facilitate placement of the covering. Radiopaque materials may be incorporated into the covering and/or into the substance for delivery by the covering. Further, radiopaque materials may be provided at only some locations on the covering such that visualization of those locations provides indication of the orientation of the covering in vivo.

The covering itself may be designed to release materials during degradation of the covering material. Thus, bone morphogenic proteins (BMPs), growth factors, antibiotics, angiogenesis promoting materials (discussed more fully below), bioactive agents (discussed more fully below), or other actively releasing materials may be incorporated into the covering material such that as the covering material is degraded in the body, the actively releasing material is released. For example, an actively releasing material may be incorporated into a biodegradable polymer covering such as one manufactured of a biodegradable polyester such as poly(lactic acid) (PLA), poly(glycolic acid) (PGA), poly(lactic-co-glycolic acid) (PLGA), or polyhydroxyalkanoates (polyhydroxybutyrates and polyhydroxyvalerates and copolymers). In some embodiments, poly(ethylene glycol) (PEG) may be incorporated into the biodegradable polyester to add hydrophilic and other physico-chemical properties to enhance drug delivery. In some embodiments, composites of allograft bone and biodegradable polymers (for example, PLEXUR® products available from Osteotech) may be used in the covering.

In some embodiments, the covering may comprise a material that becomes tacky upon wetting. Such material may be, for example, a protein or gelatin based material. Tissue adhesives, including mussel adhesive proteins and cryanocrylates, may be used to impart tackiness to the covering. In further examples, alginate or chitosan material may be used to impart tackiness to the covering. In further embodiments, an adhesive substance or material may be placed on a portion of the covering or in a particular region of the covering to anchor that portion or region of the covering in place at an implant site.

In one embodiment of a covering comprising two compartments, first and second materials may be used for the first and second compartments, respectively. The first material may release or expose a growth factor according to a first rate and the second material may release a growth factor according to a second rate. Further, the growth factors released by the first and second compartments may be the same or may be different. For example, an angiogenic growth factor may be provided with the first compartment and an osteoinductive growth factor may be provided with the second compartment.

Mesh Formulation

Any suitable technique may be used for forming a material for the covering. Generally, the material may be formed as a substantially solid material, as a sheet, as a mesh, or in other configuration. In some embodiments, the material may be a textile type material. Thus, for example, the material may be formed using a textile approach such as be weaving, rug making, knitting, etc. Such formation may be by a mechanical or industrial method. In another embodiment, a substantially solid sheet may be formed and may be treated to assume a configuration penetrable by cells, fluids, and proteins. For example, the sheet may be perforated, may be expanded to create openings, or other. Also, it would be perfectly suitable to take a thin sheet of the covering material, and to perforate it, expand it to create openings, or otherwise make it penetrable by cells, fluids and proteins.

In one embodiment, elongated bone-derived particles or fragments of small intestinal submucosa (for example, approximately 6) may be combined longitudinally into three small bundles, each having, for example, from about 1 to about 3 tissue particles. The three bundles may then be braided. Various methods of braiding and types of braids any of which may be useful in producing the material of the invention herein are also described, e.g., by Shaw, KNOTS—Useful & Ornamental, Bonanza Books, New York (1983), incorporated herein by reference. The ends of the braided tissue-derived particles may then be glued together using a fixation agent to prevent their unraveling, or they may be held together with a biocompatible polymer or metal band.

In an alternative embodiment, bone-derived particles are combined with a solvent to form a material. Exemplary solvents include water, lower alkanols, ketones, and ethers and mixtures of any of these or other materials. The material may then be extruded at an appropriate temperature and pressure to create a thread. Threads may also be produced by spinning, drawing, rolling, solvent-extruding, cutting or laser cutting from a sheet or bar stock. The material may alternatively be cast or molded into a solid sheet or bar stock and then cut into thin threads. These may be used immediately or woven into a mesh. Alternatively or in addition, they may be spliced, wrapped, plied, cabled, braided, woven, or some combination of these. The material may be shaped by thermal or chemical bonding, or both. In one embodiment, a portion of the solvent is removed from the material before extrusion.

Alternatively or in addition, the material may be cast as a slurry, extruded, or molded. A variety of materials processing methods will be well known to those skilled in the art. For example, the material may be solvent cast using a press such as a Carver press to spread the material into a film. Solvent evaporation will yield a porous film. Alternatively, the material may be compression molded into a film. The mesh size or porosity of the film will depend on the thickness of the film and the viscosity of the precursor and can be easily manipulated by one skilled in the art. Where elongated particles are used in an extruded aggregate, they will tend to be aligned roughly parallel to one another.

In an alternative embodiment, a thread of a biocompatible natural or synthetic material, for example, polylactide or collagen, may be coated with tissue-derived or other elements, for example, by dubbing. For example, a polymer fiber may be coated with an adhesive, for example, lecithin, and bone particles or other osteoconductive or osteoinductive fibrils allowed to adhere to the thread. The thread may then be twisted on itself or with a second or a plurality of similarly treated threads. Alternatively or in addition, the threads may be braided. The adhesive may be a lipid that is waxy at room temperature, for example, a di- or tri-glyceride that is solid at room temperature. Alternatively or in addition, the adhesive may be a phosphocholine or phosphatidylcholine. In some embodiments, the adhesive is a material that binds both the thread and the material that is used to coat the thread (e.g., bone particles) but that does not degrade either. Non-aqueous adhesives may improve the stability of the final aggregate as compared to aqueous adhesives.

Suitable fibers may be formed utilizing well known techniques, e.g., braiding, plying, knitting, weaving, felting, that are applied to processing natural fibers, e.g., cotton, silk, etc., and synthetic fibers made from synthetic bioabsorbable polymers, e.g., poly(glycolide) and poly(lactic acid), nylon, cellulose acetate, etc. See, e.g., Mohamed, American Scientist, 78: 530-541 (1990). For example, U.S. Pat. No. 5,378,469, herein incorporated by reference in its entirety, describes the braiding of crosslinked and noncrosslinked collagen threads using a harness braiding machine (New England Butt Co., Providence, R.I.). Specifically, collagen thread is wound onto cylindrical stainless steel spools. The spools are then mounted onto the braiding carousel, and the collagen thread is then assembled in accordance with the instructions provided with the braiding machine. In one particular run, a braid was formed of four collagen threads, which consisted of two threads of noncrosslinked collagen and two threads of crosslinked collagen. One skilled in the art will recognize that these techniques may be applied to the other fibrous materials described herein.

Fibers and more evenly dimensioned particles may also be plied into yarns using the same methods and same machinery known to those skilled in the art in plying threads made out of other material, e.g., cotton, polyester, etc. For example, U.S. Pat. No. 5,378,469 describes the production of a 60 ply yarn from noncrosslinked collagen threads. Four collagen threads were twisted together. Three of the resultant 4-ply strands were then twisted together in the opposite direction, and then 5 of the resultant 12 ply strands were twisted in the opposite direction.

Elongated materials including multistranded materials, e.g., braids, plied yarns, cables, etc., may be knitted into tubular or flat fabrics by using techniques known to those skilled in the art of producing fabrics manufactured from other types of threads. Various biologically active substances can be incorporated in, or associated with, the braided, knitted, or woven materials. Particles and fibers and materials of these (including multistranded materials) may alternatively or additionally be assembled into a material by non-woven methods such as laying, needle-punching, and hooking (as for a rug). For example, a thread may be attached to another thread or a pressed film.

Regardless of the assembly method, the material shape, mesh size, cable thickness, and other structural characteristics, e.g., architecture, may be customized for the desired application. For example, where a two dimensional aggregate is used to retain a thixotropic material within a gap, a tight weave is preferred to prevent leakage. To optimize cell or fluid migration through the mesh, the pore size may be optimized for the viscosity and surface tension of the fluid or the size of the cells. For example, pore sizes on the order of approximately 100-200 μm may be used if cells are to migrate through the mesh. Mesh size may be controlled by physically weaving strands of the material by controlling the ratio of solvent to solids in a precursor material.

Cells may be seeded onto the material, or contained within it. In one embodiment, cells may be encapsulated in a matrix such as alginate or collagen gel and the capsules placed on the material. Methods for encapsulating cells are well known to those skilled in the art; an exemplary method is disclosed in U.S. Pat. No. 4,391,909, herein incorporated by reference in its entirety. Seeded materials generally do not need to be incubated for long periods of time in solutions that could partially dissolve the binding agent. Instead, the capsules may be placed on the material or covering shortly before implantation. In another embodiment, cells are simply mixed with a gel which is then combined with the material. Alternatively, a material or covering may be cultured with cells before implantation. In one embodiment, thicker materials are used for culturing to increase mechanical integrity during implantation. Any class of cells, including connective tissue cells, organ cells, muscle cells, nerve cells, and stem cells, may be seeded onto the implant. In an exemplary embodiment, connective tissue cells such as osteoblasts, osteoclasts, fibroblasts, tenocytes, chondrocytes, and ligament cells and partially differentiated stem cells such as mesenchymal stem cells and bone marrow stromal cells are employed.

III. Covering Configuration or Form

The shape, configuration, or form of the covering may be selected for particular applications. Such shape and configuration may include, for example, the basic shape of the covering (e.g., a cylinder or a bag), whether the covering has a single or a plurality of compartments, and whether the covering includes attachment mechanisms. The covering (or delivery system) may be configured to conform to surrounding bony contours of the space in which it is placed.

Form

As previously discussed, the covering may be formed of as a mesh. Thus, the covering may comprise a woven material. The woven material may have varying degrees of permeability. It may be permeable, semi-permeable, or non-permeable. Permeability may be with respect to cells, to liquids, to proteins, to growth factors, to bone morphogenetic proteins, or other. In further embodiments, the material may be braided.

In alternative embodiments, the covering may comprise a substantially solid structure, such as a polymer structure with a chamber, or a spun cocoon.

Shape

The covering may have any suitable configuration. For example, the covering may be formed as a ring, a cylinder, a cage, a rectangular shape, a mesh, a suture-like wrap, a continuous tube, or other configuration. In specific embodiments, the covering may be formed as a thin tube designed to be inserted through catheters or an introducer tube, a rectangular shape designed to fit adjacent to spinal processes for posterolateral spine fusion, a cube like structure designed to fit between vertebral bodies or within cages for interbody spinal fusion, a tube-like shape where the ends are designed to be fitted onto nonunion long bone defects, relatively flat shapes designed to fill cranial or maxillofacial defects, rectangular structures designed for osteochondral defects, structures preshaped to fit around various implants (e.g. dental, doughnut with hole for dental implants), or relatively elastic ring-like structures that will stretch and then conform to shapes (e.g. rubber band fitted around processes). In an embodiment wherein the covering is formed as a cage, the cage may comprise a plurality of crossed filaments which define between them a series of openings for tissue ingrowth. Any of these shapes may be used for a covering comprising a plurality of compartments. For example, in a tubular embodiment, the tube may be formed into a plurality of compartments by tying a cord around the tube at one or more points, or by other suitable mechanism such as crimping, twisting, knotting, stapling, sewing, or other. The configuration of the covering may be determined by the substance to be provided within the covering. For example, if the substance to be contained comprises fibers, the covering may be formed as strings or sutures that are wrapped around the fibers.

In certain embodiments, a bone void can be filled. A compartment within the covering material can be at least partially filled with a bone repair substance. In various embodiments, at least partially filled as used herein, can mean that a percentage of the volume of a compartment (or covering material, as applicable) is at least 70% occupied, at least 75% occupied, at least 80% occupied, at least 85% occupied, at least 90% occupied, at least 95% occupied, or 100% occupied. The covering material can be inserted into an opening in the defect until the defect is substantially filled. In various embodiments, a substantially filled as used herein can mean that a percentage of the volume of a defect (or covering material, as applicable) is at least 70% occupied, at least 75% occupied, at least 80% occupied, at least 85% occupied, at least 90% occupied, at least 95% occupied, or 100% occupied. The excess material extending beyond the surface of the bone if the bone were without the defect can then be removed, or at least partially removed such that the opening of the defect is flush with the uninjured bone surface.

Figure 1B:
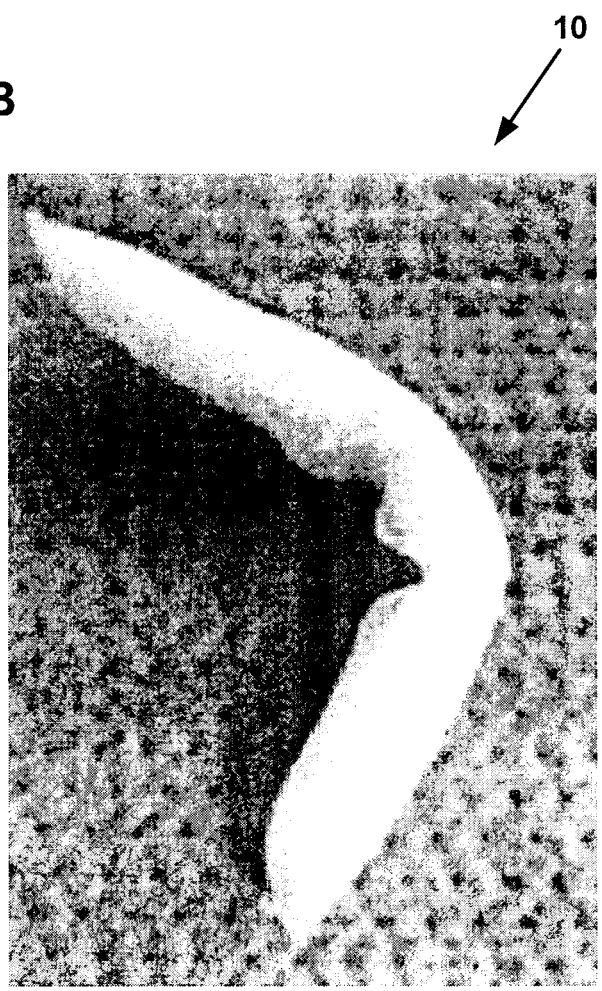
Figure 2A:
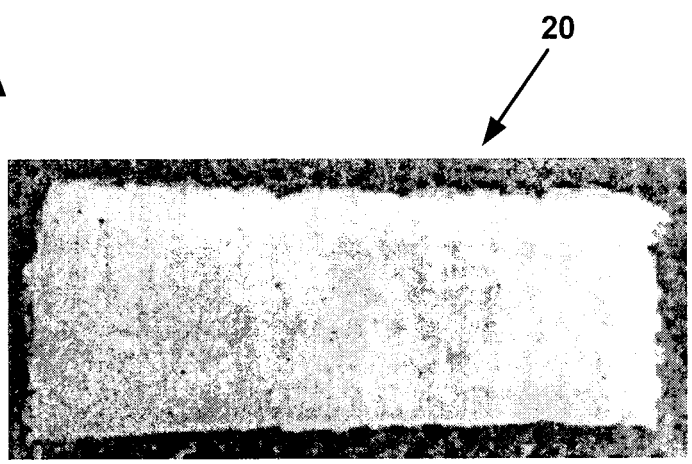
FIG. 2a illustrates a delivery system comprising a relatively wide tubular covering and a particulated substance, in accordance with one embodiment.
Figure 2B:
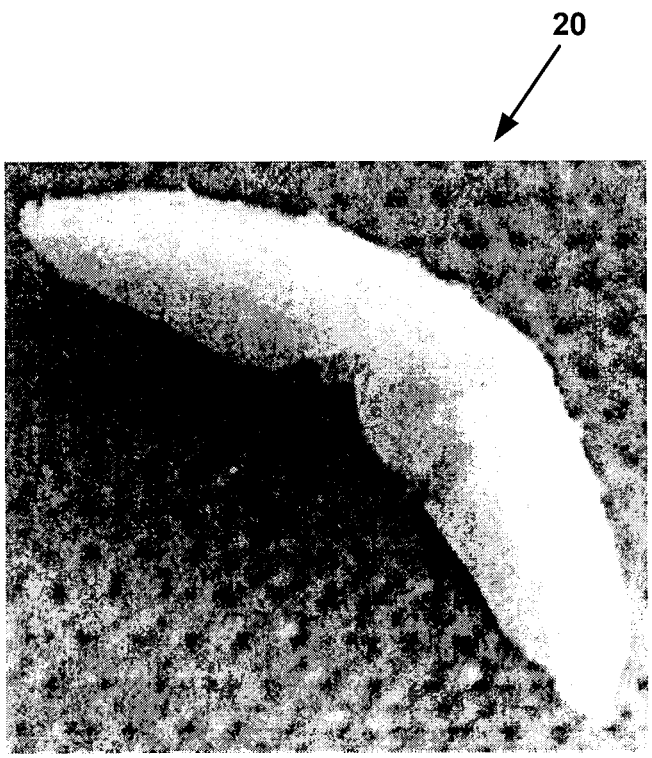

FIGS. 1a and 1b illustrate a delivery system comprising tubular covering 10 and particulated substance. In the embodiment of FIGS. 1a and 1b, the covering 10 is relatively narrow. In contrast, FIGS. 2a and 2b illustrate a delivery system comprising relatively wide covering 20. In the embodiments shown in FIGS. 1a, 1b, 2a, and 2b, the coverings 10, 20 comprise a mesh material. The particulated substance is provided within the coverings 10, 20.

Figure 3:
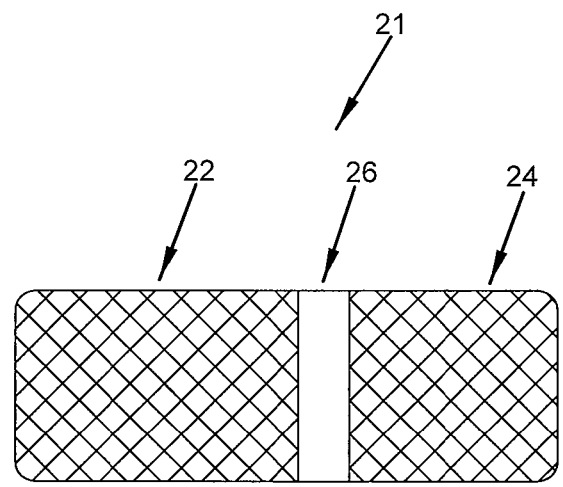
FIG. 3 illustrates a two-compartment covering comprising two single-compartment coverings coupled together, in accordance with one embodiment.

A covering as provided herein may further comprise an attachment or coupling mechanism. Any suitable attachment mechanism can be used, such as a tab, loop, tack or other structure adapted for attachment at the site. Also, for example, a covering may include a hook-and-eye (Velcro) portion. The hook-and-eye portion may be used to couple the covering to a tissue structure, such as bone, or to another covering. For example, as shown in FIG. 3, a dual compartment covering 21 may be formed by two single-compartment coverings 22, 24 coupled at portion 26 at complementary ends thereof. In the embodiment shown, the coupling portion 26 may comprise overlapping/mating Velcro portions. The size and shapes of the single compartment coverings 22, 24 may be the same or may be different. Further, the materials of the compartment coverings 22, 24 and the substances provided therein may be the same or may be different. The coupling may be done pre-implantation or post-implantation. In post-implantation embodiments, the coupling may be done by inserting first and second coverings through an opening into a space and coupling the coverings within the space. Other suitable attachment, or coupling, mechanisms are described more fully below.

In some embodiments, the covering may be labeled. Such labeling may be done in any suitable manner and at any suitable location on the covering. In some embodiments, labeling may be done by using a silk screen printing, using an altered weaving or knotting pattern, by using different colored threads, or other. The labeling may indicate information regarding the covering. Such information might include part number, donor id number, number, lettering or wording indicating order of use in the procedure or implant size, etc.

Compartments

Single Compartment

Figure 4:
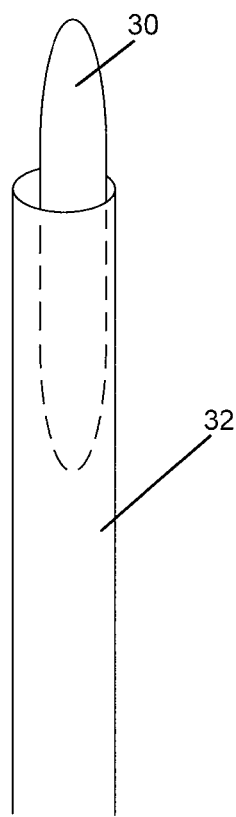
FIG. 4 illustrates a tubular covering for delivery in a catheter, in accordance with one embodiment.

As shown in FIGS. 1a, 1b, 2a, and 2b the covering may comprise a single compartment covering 10, 20. Those figures illustrated generally tubular embodiments. In further embodiments, such as shown in FIG. 4 the covering 30 may be a narrow tube for delivery through a catheter 32. For example, the covering may be delivered percutaneously using a catheter through which it is inserted. Thus, as shown, the covering 30 may have dimensions suitable for receipt in the catheter. Optionally, the covering 30 may be stiffened to facilitate insertion into the catheter 32. Such stiffening may be achieved through choice of material for the covering, by treating the material of the covering, or other. In some embodiments, the covering 30 may be coated with a material to facilitate sliding engagement with the catheter 32.

Figure 5A:
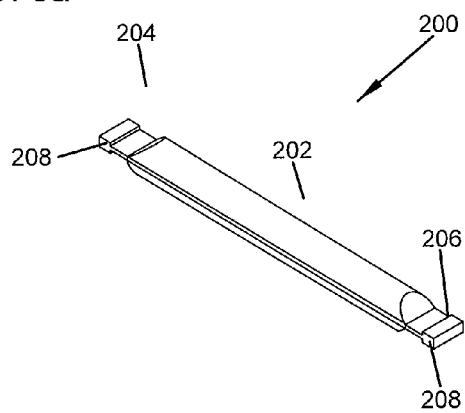
FIG. 5a illustrates a perspective view of a covering having an elongated containment portion, in accordance with one embodiment.
Figure 5B:
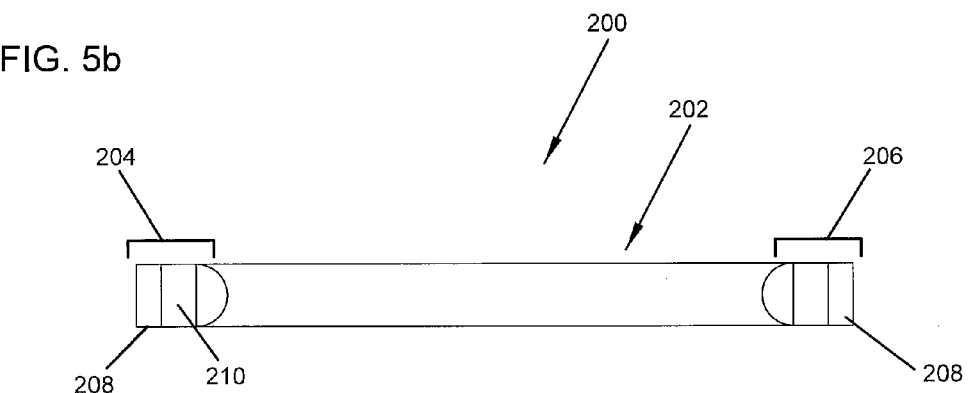
Figure 5C:
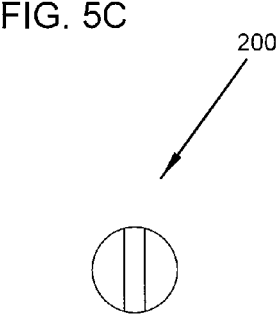

FIGS. 5a-5c illustrate a covering embodiment 200 having an elongated containment portion 202 for housing a substance for delivery, and having first and second ends 204, 206. One or both of the first and second ends 204, 206 may have an attachment mechanism 208. Any suitable attachment mechanism may be used. In the embodiment shown, each of the first and second ends 204, 206 comprises a tab attachment mechanism 208. One or both of the first and second ends 204, 206 further may be sealed. In the embodiment shown, the first end 204 is sealed. The seal 210 may comprise a portion of the tab 208, as shown, or may be separate from the tab 208. The seal 210 may have a width and a thickness suitable for maintaining a seal with the substance provided within the containment portion. For example, the seal 210 may have a length of approximately 0.6 cm, with the tab 208, including the seal 210, having a length of approximately 1.0 cm. Accordingly, the tab 208 is coextensive with the seal 210 for approximately 0.6 cm and extends approximately 0.4 cm beyond an outer edge of the seal 210. In some embodiments, one or both ends 204, 206 may be unsealed such that the covering 200 may be filled with a substance and sealed, for example via heat sealing, in the operating room. The elongated containment portion 202 comprises a length, a width, and a cross section. The length may be, for example, approximately 5 cm, approximately 10 cm, approximately 20 cm, or any other suitable length. The width may be, for example, approximately 1 cm. The length to width ratio may vary depending on application. In the embodiment of FIGS. 5a-5c, the containment portion 202 has a generally circular cross-sectional shape with an approximately 1.0 cm diameter. While exemplary dimensions are provided with respect to FIGS. 5a-5c, these dimensions are intended for illustration only and are not limiting.

Figure 6A:
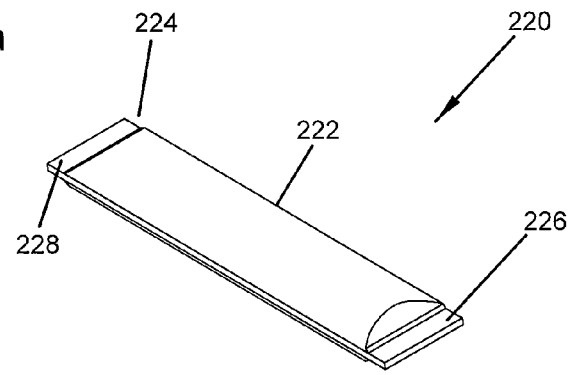
FIG. 6a illustrates a perspective view of an alternative embodiment of a covering having an elongated containment portion.
Figure 6B:
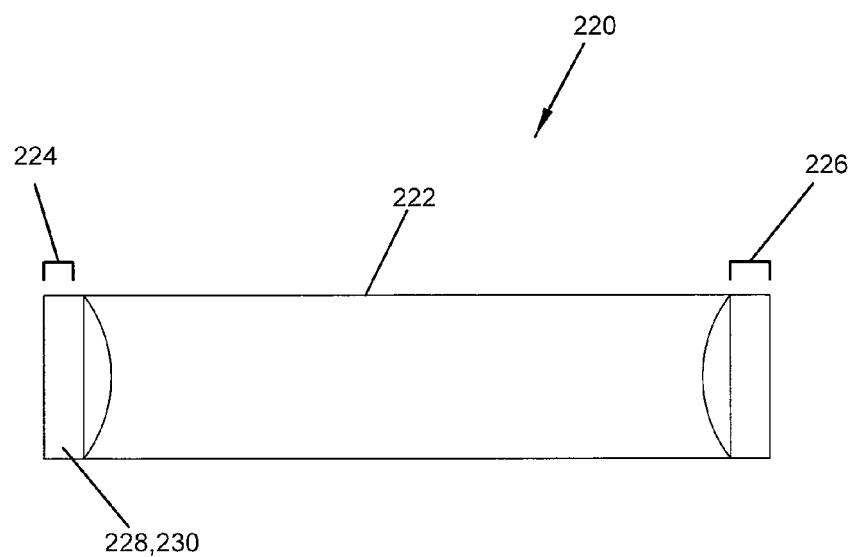
Figure 6C:
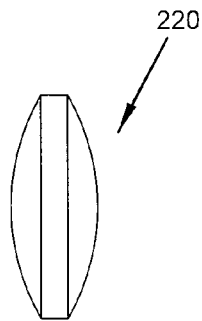

FIGS. 6a-6c illustrate an alternative embodiment of a covering 220 having an elongated containment portion 222 for housing a substance for delivery, and having first and second ends 224, 226. In the embodiment of FIGS. 6a-6c the containment portion 222 has a generally oval cross-sectional shape. In various embodiments, the covering 220 may have a width of approximately 2.5 cm, a containment portion 222 length of approximately 5 cm or approximately 10 cm, and a tab 228 length of approximately 0.5 cm. In the embodiment of FIGS. 6a-6c, a seal 230 is provided at the first end of the covering and extends over substantially the entire length of the tab 228 at the first end 224. While exemplary dimensions are provided with respect to FIGS. 6a-6c, these dimensions are intended for illustration only and are not limiting.

Figure 7A:
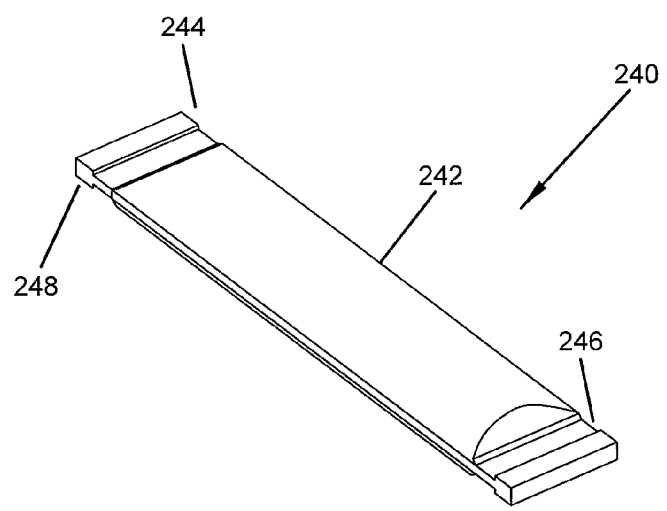
FIG. 7a illustrates a perspective view of yet an alternative embodiment of a covering having an elongated containment portion.
Figure 7B:
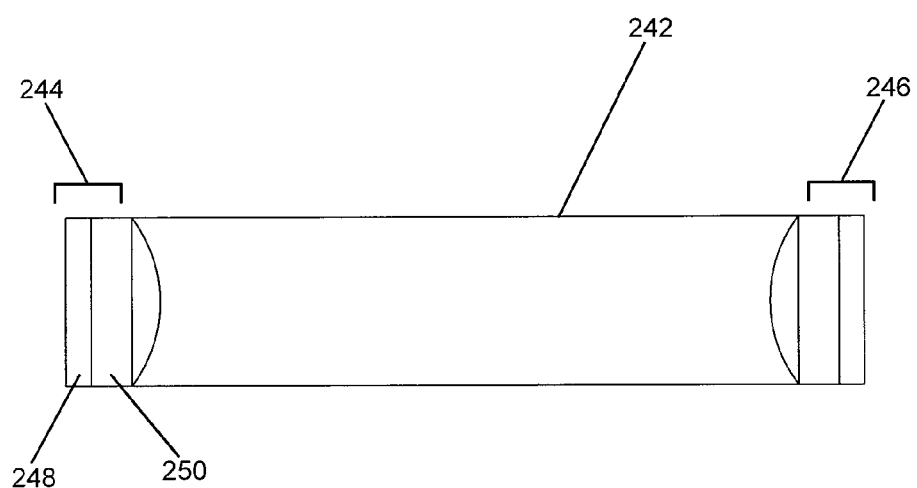
Figure 7C:
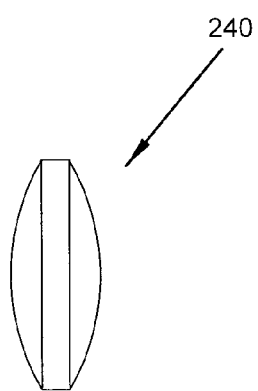

FIGS. 7a-7c illustrate an alternative embodiment of a covering 240 having an elongated containment portion 242 for housing a substance for delivery, and having first and second ends 244, 246. The embodiment of FIGS. 7a-7c is substantially similar to the embodiment of FIGS. 6a-6c except for the tabs 248 at the first and second ends 244, 246. In the embodiment of FIGS. 7a-7c, the tabs 248 have a length of approximately 1.0 cm and the associated seal 250 of the tab at the first end 244 has a length of approximately 0.6 cm. Accordingly, the tab 248 is coextensive with the seal 250 for approximately 0.6 cm and extends approximately 0.4 cm beyond an outer edge of the sea 250. While exemplary dimensions are provided with respect to FIGS. 7a-7c, these dimensions are intended for illustration only and are not limiting.

FIGS. 5a-5c, 6a-6c, and 7a-7c illustrate various alternative embodiments of a covering having an elongated containment portion for housing a substance for delivery, and having first and second ends. In each of the embodiments shown, the first and second ends include a tab attachment mechanism. In alternative embodiments, only one of the ends may have an attachment mechanism. Further, the attachment mechanism may have an alternative configuration, such as a bore for receiving a screw. FIGS. 5a-5c, 6a-6c, and 7a-7c illustrate generally circular and generally oval cross-sectional shapes. In alternative embodiments, any cross-sectional shape, such as a generally rectangular, generally square, generally star, or any other suitable shape may be used. The length, width, and length-to-width ratio may vary depending on the application for the covering.

In one embodiment of a single compartment covering, a plurality of substances may be provided within the covering based on characteristics of the substances. For example, where it is desirable to include a particulated first substance within a material having mesh openings larger than the substance, a second substance may be provided surrounding the particulated first substance to reduce the likelihood of release of particles of the first substance from the mesh. Thus, for example, a particulated first substance and a particulated second substance may be provided wherein the particles of the first substance have a smaller size than the particles of the second substance. A covering is provided comprising a mesh having mesh openings or pores larger than the particles of the first substance. For use, the first substance is provided generally centrally within the covering, the second substance is provided around the first substance and thus between the first substance and the second substance. In further embodiments, the second substance may be coated, for example via spray coating or solvent casting.

In yet a further embodiment, a single compartment covering may be used as a spacer for nonunion. For example, the covering may be placed in a canal of a long bone.

Multi Compartment

In alternative embodiments, and as briefly discussed with respect to FIG. 3, the covering may comprise a plurality of compartments. For example, the covering may comprise nested coverings, coverings coupled via a temporary barrier, coverings separated with a boundary, and others, described below. In embodiments comprising two compartments, a second compartment may be adjacent, apart from, inside, or surrounding a first compartment. Materials for the first compartment and the second compartment (which may be designated first and second substances) may be the same, partially the same, or different. The materials for the first compartment and the second compartment may have different release profiles, different porosities, and other different characteristics. Selection of materials, positioning of the compartments, and other factors relating to the first and second compartments may be chosen to achieve simultaneous or sequential delivery or release of a substance or substances. A first substance may be provided in the first compartment and a second substance may be provided in the second compartment. In some embodiments, an osteoinductive substance may be placed in a compartment generally adjacent tissue being treated as implanted and an osteoconductive substance may be placed in a compartment not adjacent tissue being treated. Release rates for the materials provided in the first compartment and the second compartment may be different. In some embodiments, at least one of the compartments may be unfilled at the time of surgery and autograft or other material may be provided therein in the operating room or at the surgical site. In some embodiments, the covering may form a 3D scaffold.

Figure 8:
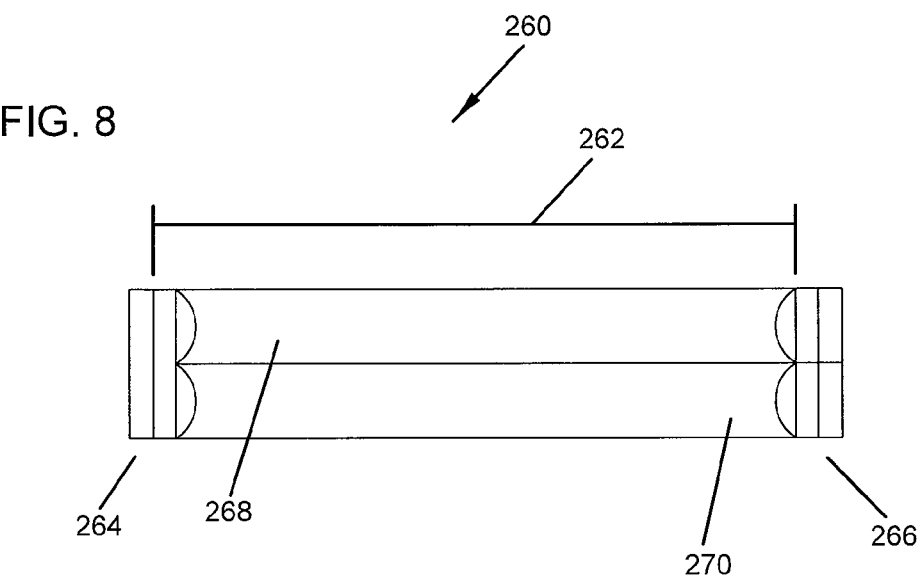
FIG. 8 illustrates a first embodiment of a multi-compartment covering having an elongated containment portion.

The embodiments of FIGS. 5a-5c, 6a-6c, and 7a-7c may further be configured as multi-compartment embodiments. FIG. 8 illustrates an exemplary multi-compartment embodiment of a covering 260 having an elongated containment portion 262 for housing a substance for delivery, and having first and second ends 264, 266. In the embodiment of FIG. 8, the elongated containment portion 262 comprises first and second compartments 268, 270 extending substantially the entire length of the elongated containment portion 262. As shown, the first and second compartments 268, 270 extend side-by-side with each of the first and second compartments 268, 270 extending from the first end 264 of the covering 260 to the second end 266 of the covering 260. Alternatively, the first and second compartments may extend one over the other, such as the first compartment arranged over the second compartment.

Figure 9:
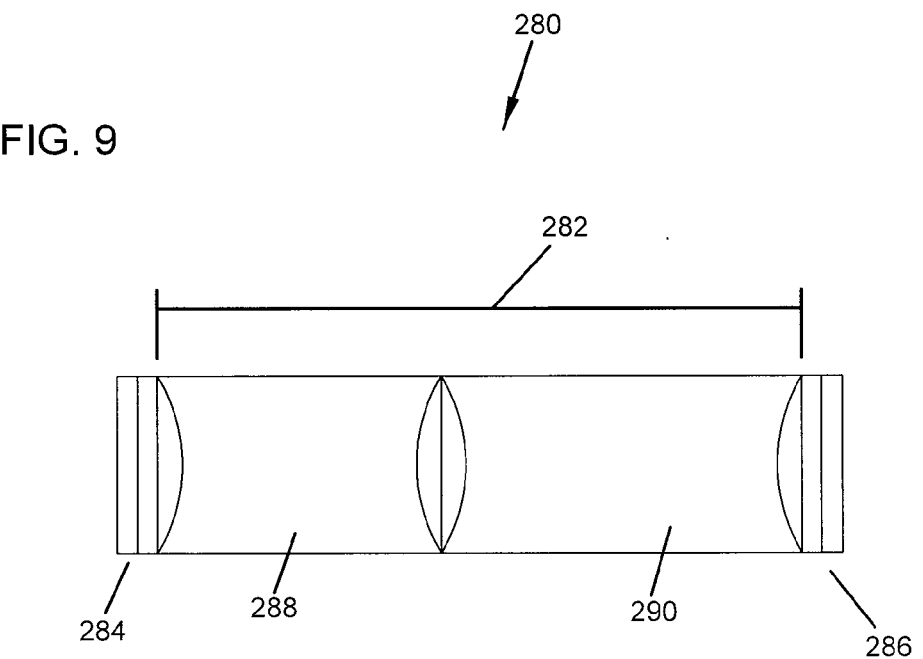
FIG. 9 illustrates a second embodiment of a multi-compartment covering having an elongated containment portion.

FIG. 9 illustrates an exemplary multi-compartment embodiment of a covering 280 having an elongated containment portion 282 for housing a substance for delivery, and having first and second ends 284, 286. In the embodiment of FIG. 9, the elongated containment portion 282 comprises first and second compartments 288, 290 with one compartment 288 provided adjacent the first end 284 and one compartment 290 provided adjacent the second end 286. The compartments 288, 290 may have substantially the same length, as shown, or may have different lengths.

With each of the embodiments of FIGS. 8 and 9, the compartments may be separated by a seal, may communicate therebetween, may be substantially separate, or may be otherwise divided with respect to other multi-compartment embodiments.

Figure 10:
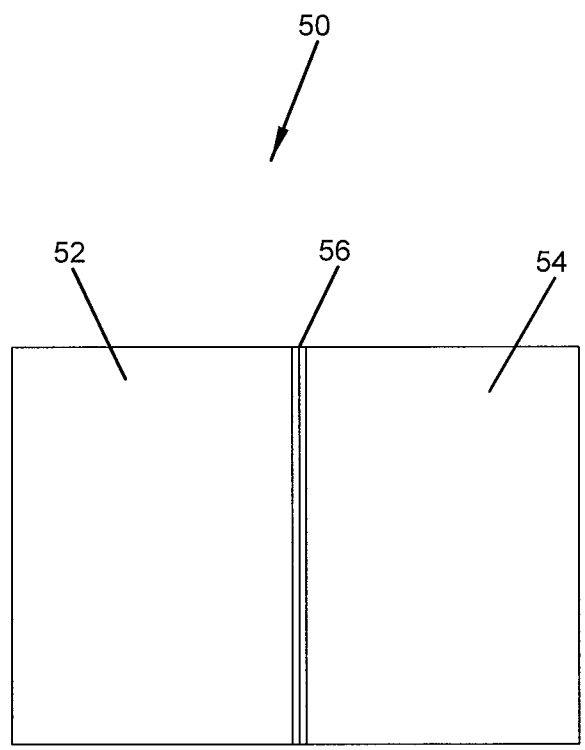
FIG. 10 illustrates a dual-compartment covering comprising first and second compartments situated side-by-side and separated by a barrier, in accordance with one embodiment.

In one multi-compartment embodiment, shown in FIG. 10, the covering 50 comprises first and second compartments 52, 54 situated side-by-side and separated by a barrier 56. The barrier 56 may be temporary or may be substantially permanent (remaining for the life of the covering 50). A temporary barrier may be a sheet or a masking agent. A boundary may be provided for dividing between two tissue types, for example between intervertebral disk and bone, between tendon and bone, between meniscus and bone, or between cartilage and bone. The barrier 56 may be integral with the covering 50, integral with one of the first and second compartments 52, 54, or may be coupled to the covering 50 or compartments 52, 54.

Figure 11:
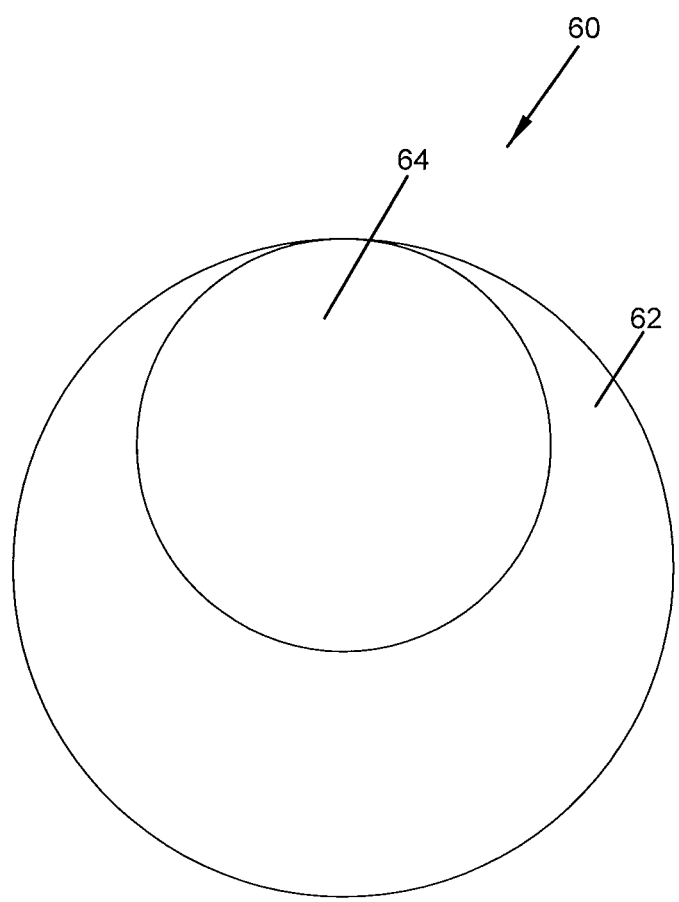
FIG. 11 illustrates a nested dual-compartment covering, in accordance with one embodiment.

FIG. 11 illustrates a nested dual-compartment embodiment 60. As shown, a second compartment 64 is provided within a first compartment 62. Selection of materials for provision in each of the first and second compartments may be based on release kinetics from the first compartment and from the second compartment (provided within the first compartment and thus also within the material provided in the first compartment). In one embodiment, smaller particles of a substance are provided within the first compartment and the first compartment accordingly comprises a tighter mesh while larger particles of a substance are provided within the second compartment and the second compartment comprises a looser mesh. Either or both of the first compartment 62 and the second compartment 64 may be preloaded. Alternatively, either or both of the first compartment 62 and the second compartment 64 may be left empty at manufacture for loading in the operating room or at the surgical site. In one embodiment, the first compartment may be preloaded and a port provided to access the second compartment in the operating room or at the surgical site. In some embodiments, a nesting configuration may comprise a wrapped configuration.

In some embodiments, at least one but not all of the compartments may be weight-bearing. In other embodiments, all of the compartments may be weight-bearing.

Figure 12A:
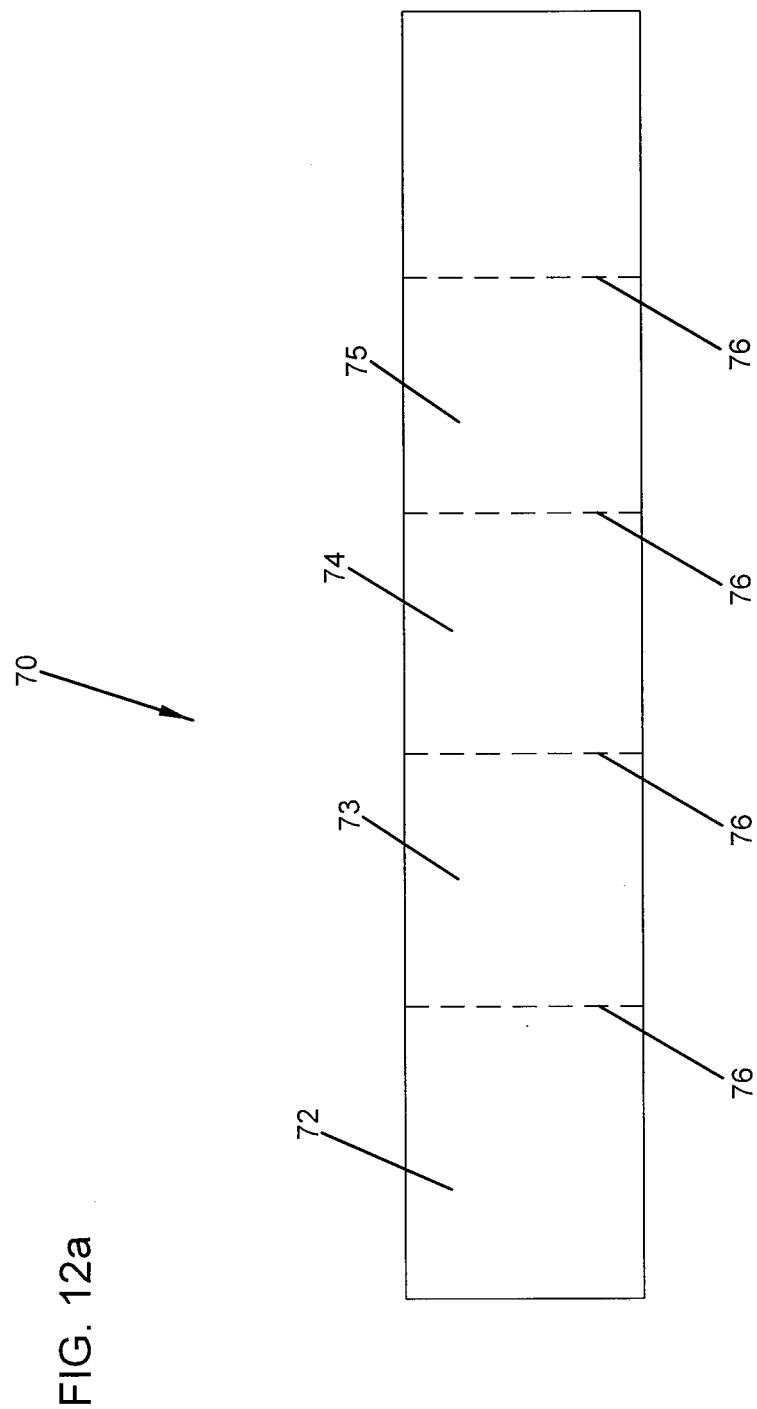
FIG. 12a illustrates a covering comprising as a plurality of compartments separated by perforations, in accordance with one embodiment.

In some embodiments, the covering may be perforated between compartments for separation. For example, FIG. 12a illustrates a covering 70 comprising a plurality of compartments 72, 73, 74, and 75 separated by perforations 76. The surgeon may select the number of compartments desired for placement and cut or pull/tear along a perforation 76 providing that number of compartments. If the covering is made of a material that is brittle or strain hardens, the surgeon may separate the compartments by bending the selected portion back upon itself and reversing until the segments separate. In such embodiment, every other compartment, for example, may be preloaded or filled with a substance for delivery. Alternatively, only some of the compartments may be preloaded, for example, every other compartment may be preloaded such that alternating compartments may be filled in the operating room or at the surgical site.

In one embodiment, the covering may comprise a penetrable material at a first compartment configured for placement adjacent bone and a substantially impenetrable material at a second compartment configured for placement adjacent soft tissue. Alternatively, the material of the compartments may have substantially identical characteristics. The covering then can be positioned in any desirable manner. By way of example only, a covering may have a porous surface that is positioned adjacent bone, and a separate or opposite surface that has a generally impenetrable surface that is positioned adjacent soft tissue. Alternatively, a covering may have one compartment that comprises a porous material, and a second compartment that comprises a substantially impenetrable material.

In another embodiment, the covering may comprise a continuous tube wherein the tube may be twisted to divide portions of the tube. The tube thus may be divided into a series of implants, each having ends that may be twisted or heat treated. Any suitable manner of dividing the tube into a plurality of compartments may be used. For example, the tube may be crimped, heat treated, twisted, knotted, stapled, sewn, or otherwise divided. Any suitable tool may be used for dividing the tube into such compartments including, for example, a crimper, a heat tool, or other.

Figure 12B:
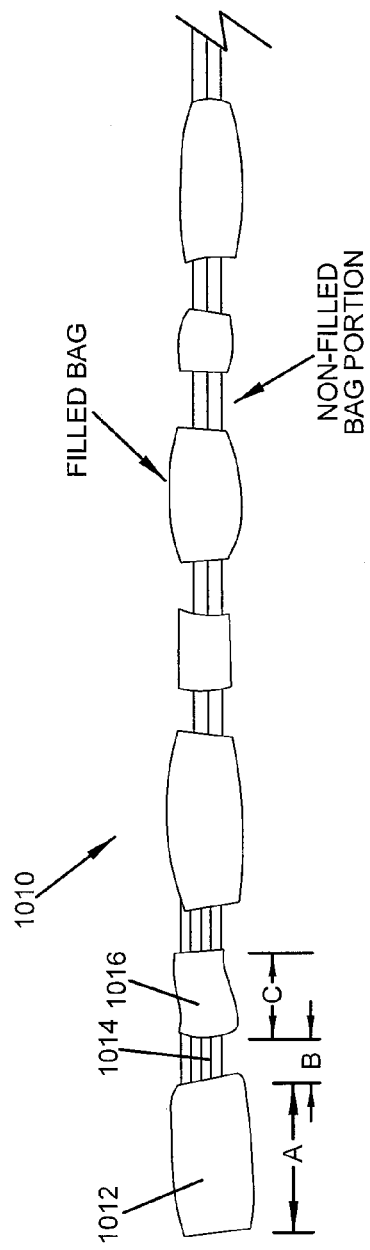
FIG. 12b illustrates a top view of a multi-compartment covering configured to be foldable and stackable, in accordance with one embodiment.
Figure 12C:
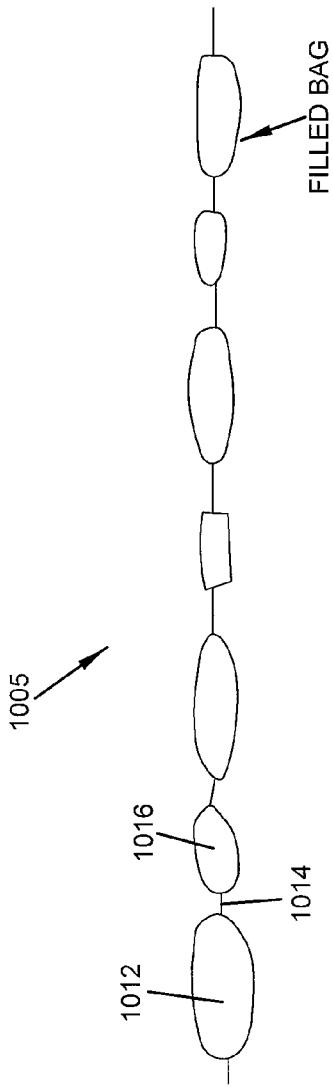
FIG. 12c illustrates a side view of a multi-compartment covering configured to be foldable and stackable, in accordance with one embodiment.
Figure 12D:
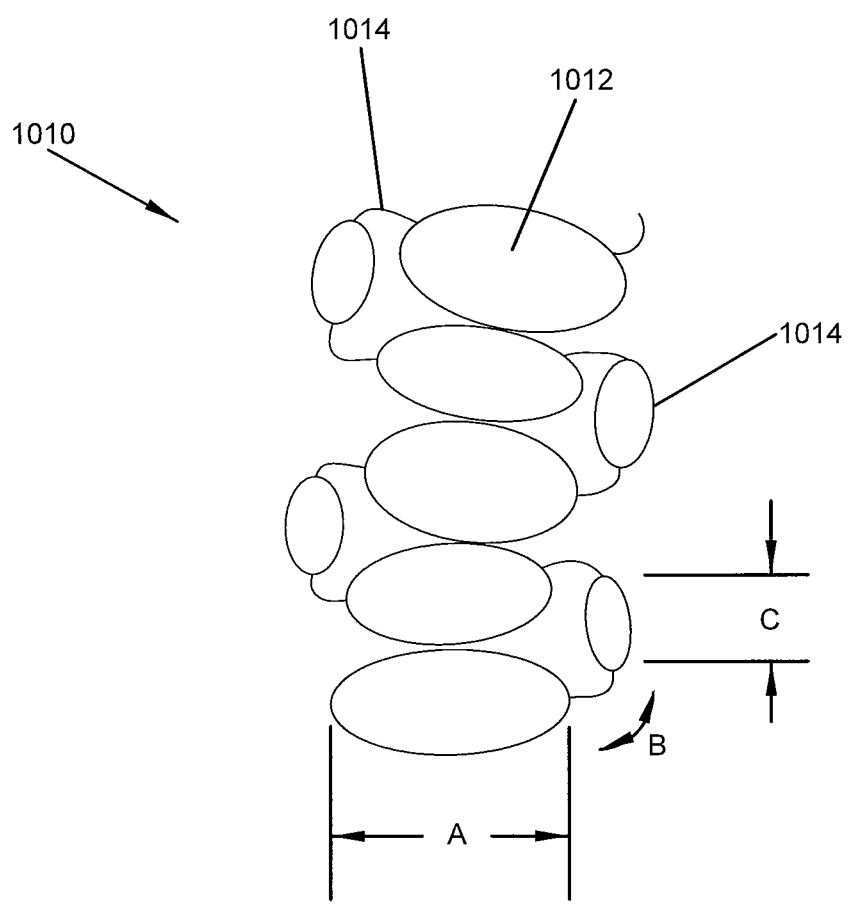
FIG. 12d illustrates a stacking sequence of a multi-compartment covering configured to be foldable and stackable, in accordance with one embodiment.

In some embodiments, a multi-compartment covering may be configured to be foldable and stackable. A first embodiment of a foldable and stackable covering is shown in FIGS. 12b-12d. FIG. 12b illustrates a top view and FIG. 12c illustrates a side view. As shown, the covering 1010 comprises a series of individual segments including segments of a first type 1012, segments of a second type 1014, and segments of a third type 1016. The segments of a first type 1012 are generally longer lengths of covering that may be filled with a substance for delivery. The segments of a second type 1014 extend between the segments of the first type 1012 and the segments of the third type 1016. The segments of the second type 1014 may be generally short lengths of covering and may be left unfilled. In some embodiments, the segments of the second type 1014 may not be formed as a covering and may simply be a material spanning the segments of a first type 1012 and the segments of a third type 1016. The segments of the third type 1016 are generally shorter lengths of covering. The length of the segments of a third type 1016 generally correlates to a length less than a stacked height of two segments of the first type 1012. FIG. 12d thus illustrates a stacking sequence of the covering of FIGS. 12b and 12c. As shown, segments of the first type 1012 are generally stacked on top of one another, segments of the third type 1016 extend along a side of the stacked segments of the first type 1012, and segments of the second type 1014 span between the segments of the first type 1012 and the segments of the third type 1016. It will be understood that the number of types of segments and their length can be varied depending upon the requirements of the surgical site.

Figure 12E:
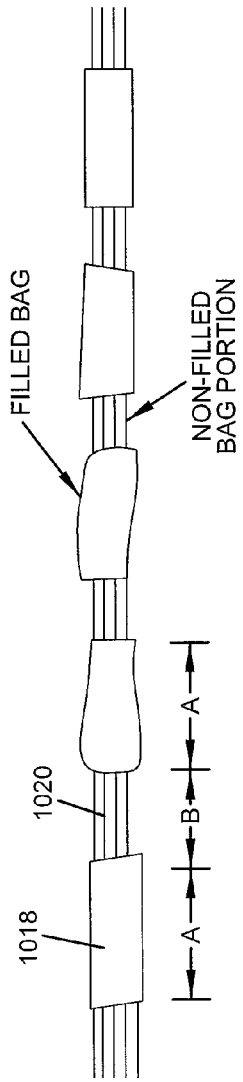
FIG. 12e illustrates a top view of another embodiment of a foldable and stackable covering where there may be a segment of a first type and a segment of a second type.
Figure 12F:
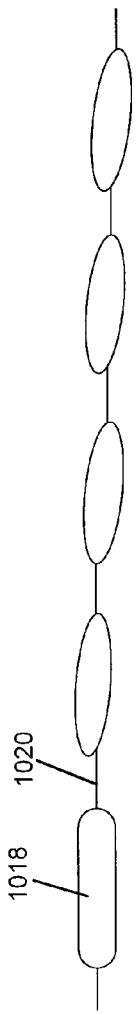
FIG. 12f illustrates a side view of another embodiment of a foldable and stackable covering where there may be a segment of a first type and a segment of a second type.
Figure 12G:
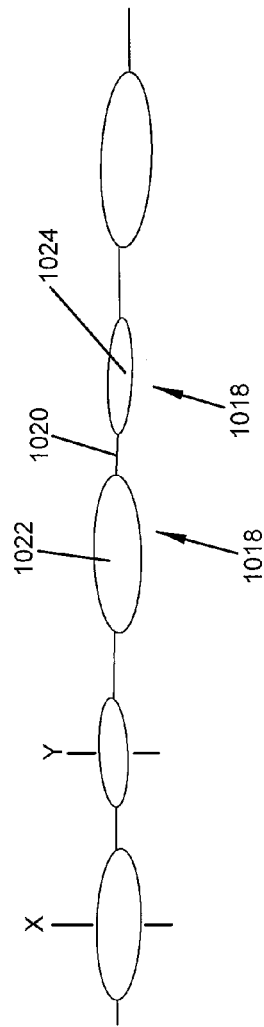
FIG. 12g illustrates another side view of another embodiment of a foldable and stackable covering where there may be a segment of a first type and a segment of a second type.

Second and third embodiments of a foldable and stackable covering are shown in FIGS. 12e-12g. FIG. 12e illustrates a top view and FIGS. 12f and 12g illustrate side views. As shown, the foldable and stackable coverings may comprise a segment of a first type 1018 and a segment of a second type 1020. The segments of the first type 1018 may be filled with a substance for delivery. The segments of a second type 1020 extend between the segments of the first type 1018. The segments of the second type 1020 may be unfilled coverings or may be provided as, for example, a material spanning segments of the first type 1018. In the embodiment of FIG. 12f, each of the segments of the first type 1018 are approximately equally filled. Thus, when stacked, each of the segments of the first type provide approximately equal height. In the embodiment of FIG. 12g, the segments of the first type 1018 alternate between first 1022 and second fill levels 1024. Thus, when stacked, the segments of the first type 1018 provide different heights. In the embodiment shown, every other segment of the first type 1018 has like fill levels. In alternative embodiments, every third, every fourth, or other segment of the first type may have like fill levels.

Any other suitable conformation or shape or combination of these also may be used.

For both single and multi-compartment coverings, the covering may be closed after filling substances. Accordingly, the covering may be provided in an unfilled, unsealed state. After a substance for delivery is placed in the covering, the covering may be permanently or temporarily closed. Permanent closure may be, for example, by heat sealing, stitching, adhesion, or other methods. Temporary closure may be by tying, fold lock, cinching, and etc. A temporarily closed covering can be opened without damaging the covering during surgical implantation to add or remove substances in the covering.

Attachment Mechanisms

The covering may be configured with structures to permit attachment at the surgical site, such as to skeletal tissue or to soft tissue structures, or for attachment to other coverings, or for attachment to adjacent implantable medical devices or products (such as a rod or screw or cross-brace of a pedicle screw fixation system, a hip prosthesis, a bone plate, and the like). Generally, the attachment mechanism may be used to retain the covering at the surgical site and any mechanisms capable of doing so may be used. The attachment may be to bone or to adjacent tissues such as muscle, tendon, or ligament. Where the covering retains a bone graft substance, the covering may be held in a relatively stable position relative to bone (or relative to the surgical site or surgical defect) to promote bone growth. Accordingly, in some embodiments, the delivery system may be suitable for assisting in attaching tendons, artificial tendons, or ligaments to bone or other structure.

The bone or soft tissue to which the covering is attached may be prepared for receiving the attachment mechanism(s). For example, in spinal applications, slots or perforations may be provided in posterior elements such as transverse processes, spinous processes, or other bone or tissue to receive the attachment mechanism.

Any suitable attachment mechanism may be used, including mechanical, physical, chemical, and biological attachment mechanisms. The attachment mechanism may be provided at an end of the covering, centrally in or on the covering, generally in or on the body of the covering, or any combinations of these. U.S. Pat. No. 5,899,939 describes attachment mechanisms that may be adapted for use with a covering as provided herein, and is herein incorporated by reference. When an attachment mechanism is used to couple first and second coverings to one another, such attachment or coupling may be done pre-implantation or post-implantation. In post-implantation embodiments, the coupling may be done by inserting first and second coverings through an opening into a space and coupling the coverings within the space. In some embodiments, the covering may be provided with attachment mechanisms to facilitate suturing or other attachment of the covering in vivo.

In some embodiments, a covering may include an area for receipt of an attachment mechanism. For example, a covering may include a tab for receipt of a screw. In other embodiments, an attachment mechanism may interface with any portion of the covering. For example, a screw attachment mechanism may be threaded through a covering at any location, including central to a containment area of the covering. In some embodiments, a screw attachment mechanism may be threaded through the covering and the substance provided in the containment area of the covering.

A further method of attachment may comprise suturing or otherwise attaching the covering to a tether, anchor, or screw embedded in a bony structure, e.g. a pedicle screw of a spinal stabilization system. Such screw, anchor, or tether may pass through the covering and its contained contents to provide fixation, or through a tab at a margin of the covering, or through other structure of the covering.

Figure 13A:
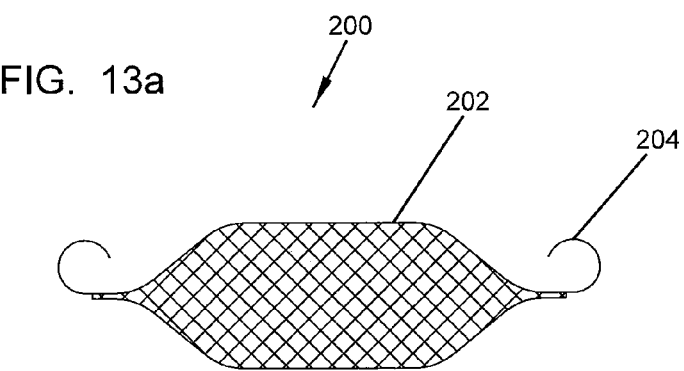
FIG. 13a illustrates a covering having a hook attachment mechanism, in accordance with one embodiment.
Figure 13B:
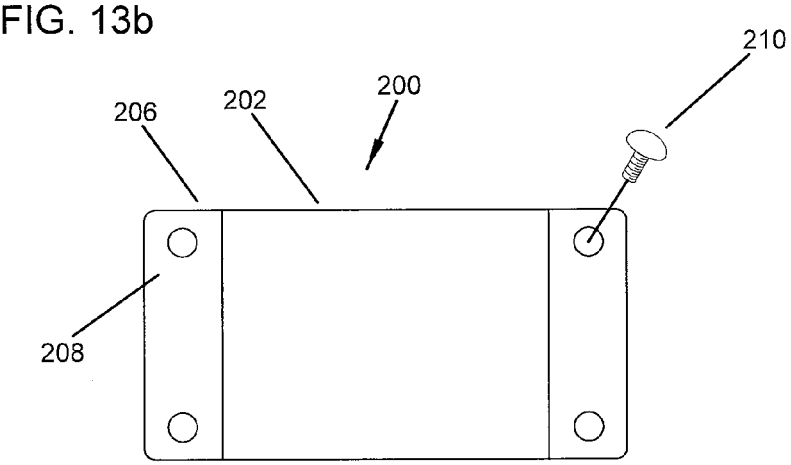
FIG. 13b illustrates a covering having a screw attachment mechanism, in accordance with one embodiment.
Figure 13C:
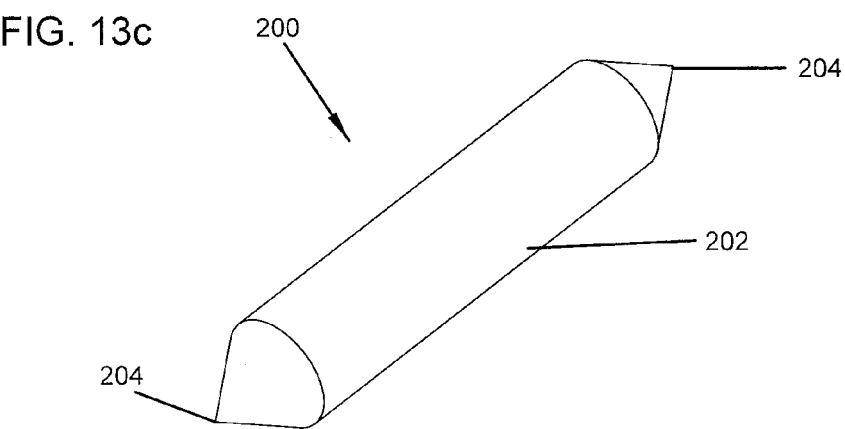
FIG. 13c illustrates a covering having a mechanical attachment mechanism, in accordance with one embodiment.

FIGS. 13a-13c illustrate a covering with a mechanical attachment mechanism. FIG. 13a illustrates a covering 200 comprising a compartment 202 with a mechanical attachment mechanism 204, such as a hook, as shown, at an end thereof. FIG. 13b illustrates a covering 200 comprising a compartment 202 and ends 206 with a mechanical attachment mechanism 204 comprising openings 208 at each end 206 of the covering 200 and a screw 210 for placement through the opening 208. FIG. 13c illustrates a covering 200 with a mechanical attachment 204 provided at an end thereof. In various embodiments, the mechanical attachment mechanism 204 of FIG. 13c may be a hook, barb, staple, screw, cap screw, nail or tack, bolt, button, tab, flap, hook-and-eye material, loop, rivet, stud, or cam lock (or other conformant fastener), clamp (or cramp), clasp, grommet, pin, retaining ring, rivet, snap, staple, tack, toggle, zipper, or other configuration. In some embodiments, hinges, springs, or like mechanisms may be used as attachment mechanisms. Any of these fasteners may be made of any suitable material, including metal, ceramic, tissue such as allograft, xenograft, autograft, collagen, any of the materials listed above in the section entitled Exemplary Covering Materials, or combinations of these. In a further embodiment, the attachment mechanism may comprise a press-fit system. In a specific screw attachment mechanism, attachment may be done via interference screw fixation. For example, attachment may be via biodegradable interference screw fixation. Combinations of these also may be used.

Figure 13D:
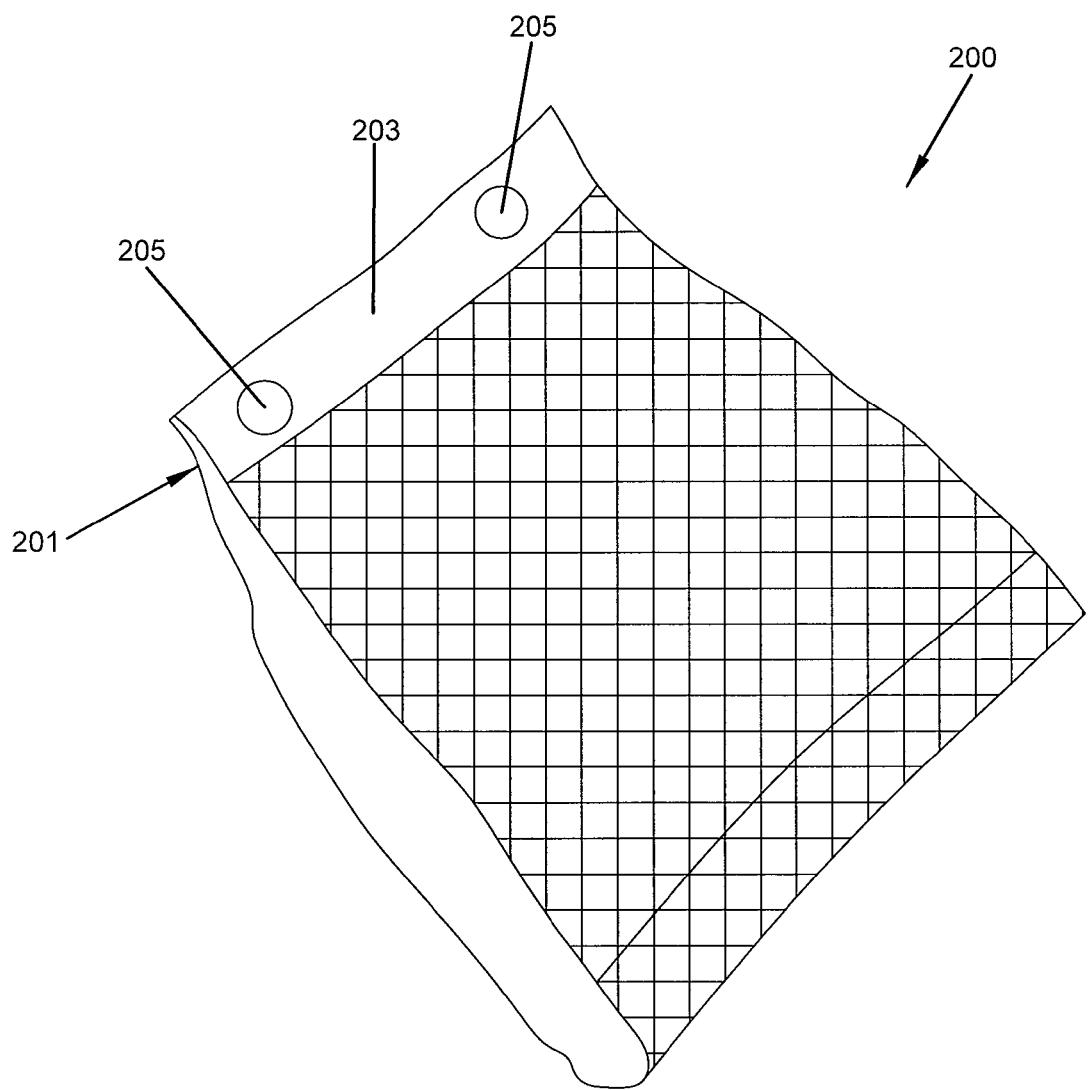
FIG. 13d illustrates a covering having a tab attachment mechanism, in accordance with one embodiment.

FIG. 13d illustrates a covering having a tab attachment mechanism. As shown, the covering 200 is generally square shaped with a thinner portion 201 at one end thereof. The thinner portion 201 includes a tab 203 with thru holes 205 for receiving screws. In the embodiment shown, two thru holes 205 are provided. The tab 203 may be integrally formed with the material of the covering 200 or may be separately formed and coupled with the covering 200. The tab 203 thus may be formed of the same material as the covering 200 or may be formed of a different material as the covering 200. In some embodiments, the tab may be formed of a reinforced material relative the material of the covering. In some embodiments, more or fewer thru holes may be provided. Further, while FIG. 13d illustrates a tab at one end of the covering, it is to be appreciated that such a tab may be provided at more than one end, margin, edge, or other of the covering.

Figure 13E:
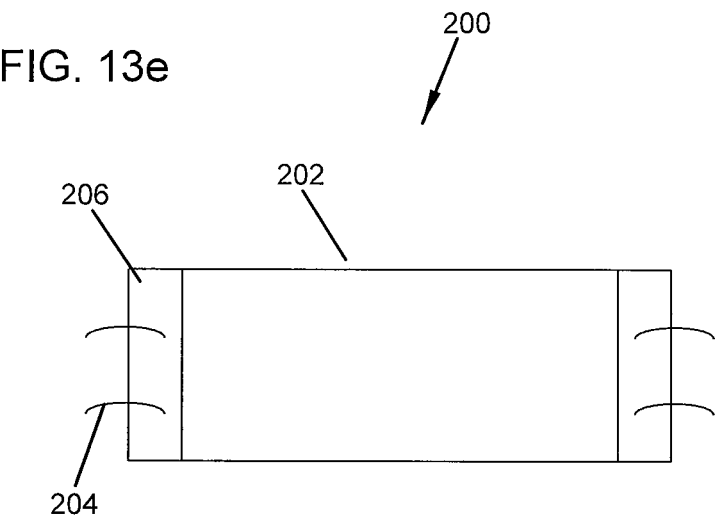
FIG. 13e illustrates a covering having a suture attachment mechanism, in accordance with one embodiment.
Figure 13F:
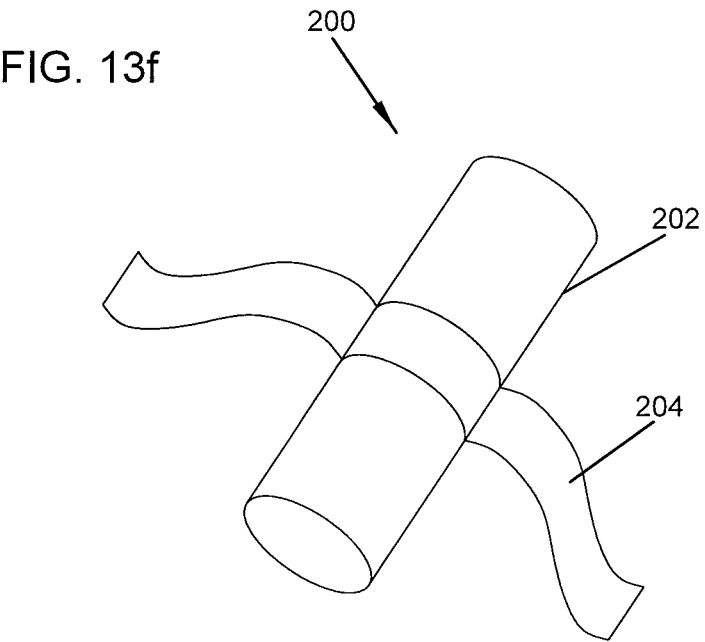
FIG. 13f illustrates a covering having a wrap attachment mechanism, in accordance with one embodiment.

FIGS. 13e and 13f illustrate embodiments of physical attachment mechanisms, e.g., wherein the attachment mechanisms comprise a band-like structure. FIG. 13e illustrates a covering 200 comprising a compartment 202 and ends 206. Sutures 204 are provided through the ends 206 of the covering 200. In alternative embodiments, sutures 204 may be provided through the compartment 202. FIG. 13f illustrates a covering 200 comprising a compartment 202 and a wrap attachment mechanism 204. The wrap is provided around the compartment 202 and is generally centrally placed. Further physical attachment mechanisms suitable for use, for example in the embodiment of FIG. 13f, may comprise wraps, sutures, wires, strings, elastic bands, cables, ropes, chains, plastic wrap, strap, tie, cable tie, or other mechanisms. These mechanisms may be coated, such as with plastic. In some embodiments, a plurality of mechanisms, such as a multiple parallel wires, may be joined together, for example with a plastic strip coating. Suitable techniques for using such attachment mechanisms may include suturing, stitching, knotting, twisting, cinching, knot tying, and similar techniques. Any of these physical fastening materials may be made of any suitable material, including metal, tissue such as allograft, xenograft, autograft, collagen, any of the materials listed above in the section entitled Exemplary Covering Materials, or combinations of these.

Figure 13G:
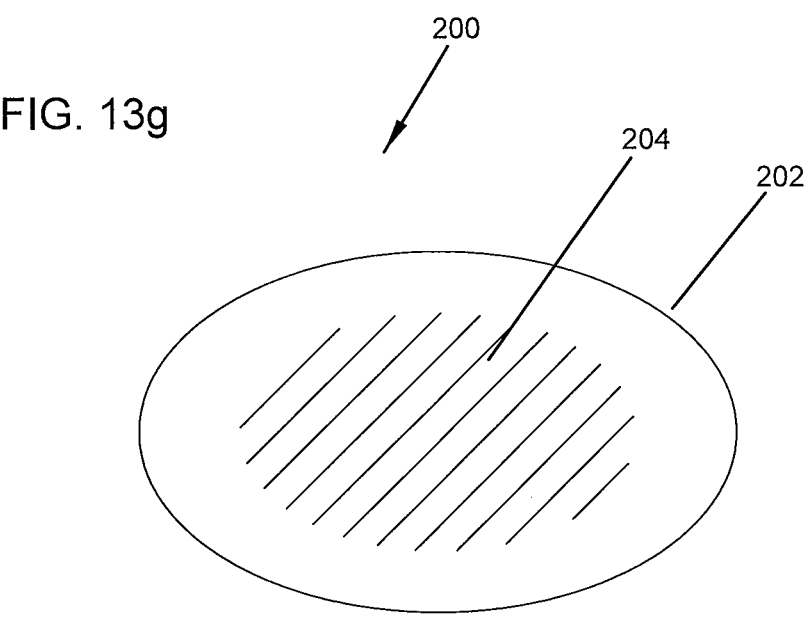
FIG. 13g illustrates a covering having an adhesive attachment mechanism, in accordance with one embodiment.
Figure 13H:
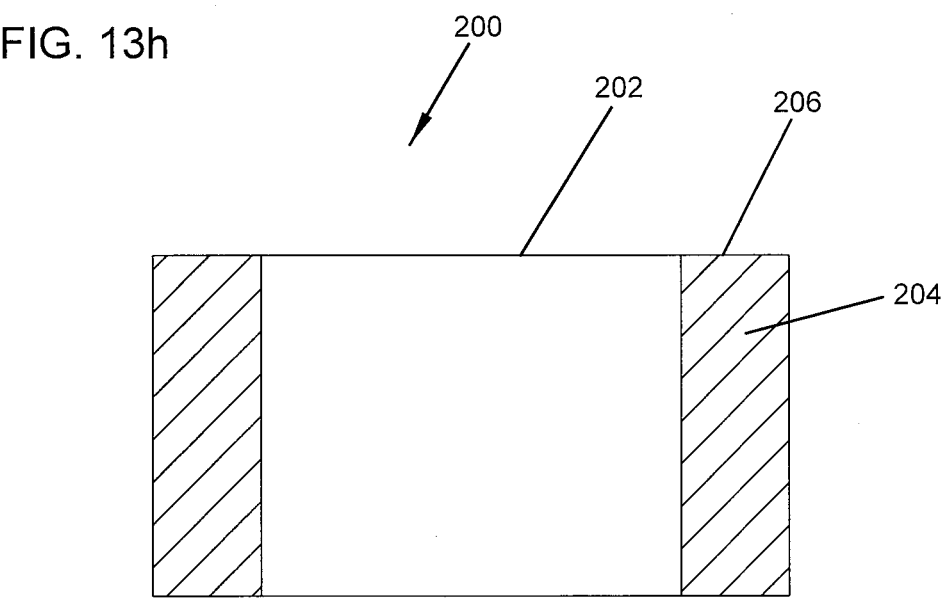
FIG. 13h illustrates a covering having an adhesive attachment mechanism, in accordance with a further embodiment.

Chemical attachment mechanisms may comprise, for example, a bioadhesive or glue, cement, tape, tissue adhesives, or similar mechanism. Chemical attachment mechanisms may further comprise mechanisms that facilitate cross-linking. In further embodiments, attachment mechanisms such as crimping, welding, soldering, or brazing may be used. For example, tissue welding may be used (see, for example, http://www.lasertissuewelding.com/laser_mediated_tissue_soldering and http://www.csmgtechinternational.com/presentation.html). Further, attachment may be achieved via friction. FIGS. 13g and 13h illustrate coverings with chemical attachment mechanisms. FIG. 13g illustrates a covering 200 with a compartment 202. An adhesive is placed over a surface of the compartment 202. FIG. 13h illustrates a covering 200 with a compartment 202 and ends 206. An adhesive 204 is placed over the ends 206. Suitable adhesives for use with the embodiments of FIGS. 13g and 13h include, for example, cyanoacrylates (such as histoacryl, B Braun, which is n-Butyl-2 Cyanoacrylate; or Dermabond, which is 2-octylcyanoacrylate); epoxy-based compounds, dental resin sealants, dental resin cements, glass ionomer cements, polymethyl methacrylate, gelatin-resorcinol-formaldehyde glues, collagen-based glues, inorganic bonding agents such as zinc phosphate, magnesium phosphate or other phosphate-based cements, zinc carboxylate, L-DOPA (3,4-dihydroxy-L-phenylalanine), proteins, carbohydrates, glycoproteins, mucopolysaccharides, other polysaccharides, hydrogels, protein-based binders such as fibrin glues and mussel-derived adhesive proteins, and any other suitable substance. Adhesives may be selected for use based on their bonding time; e.g., in some circumstances, a temporary adhesive may be desirable, e.g., for fixation during the surgical procedure and for a limited time thereafter, while in other circumstances a permanent adhesive may be desired. Where the compartment 202 is made of a material that is resorbable, the adhesive can be selected that would adhere for about as long as the material is present in the body. In some embodiments, the covering material may be treated to form chemical linkages between the covering and adjacent tissue, whether bone or soft tissue.

In some embodiments, biological attachment may be via mechanisms that promote tissue ingrowth such as by a porous coating or a hydroxyapatite-tricalcium phosphate (HA/TCP) coating. Generally, hydroxyapatite bonds by biological effects of new tissue formation. Porous ingrowth surfaces, such as titanium alloy materials in a beaded coating or tantalum porous metal or trabecular metal may be used and facilitate attachment at least by encouraging bone to grow through the porous implant surface. These mechanisms may be referred to as biological attachment mechanisms.

Generally, any combination of mechanical, physical, chemical, or biological attachment mechanisms may be used.

Any of the various attachment mechanisms may be provided as part of the covering or may be supplied separately. In various embodiments, the attachment mechanisms may be integral to the covering. Alternatively, the attachment mechanisms may be secured to the covering, for example, by stitching, welding, crimping, or other. The attachment mechanisms may have any suitable geometric configuration and may optionally include apertures for receiving other components for coupling in vivo, such as an aperture for receiving a screw. Thus, for example, an attachment mechanism may be provided configured for receiving an anchor for fixation to bone. Generally, any number of attachment mechanisms may be provided at any suitable location on the covering.

The attachment mechanisms may be manufactured of the same material as the portion of the covering to which it is coupled or may be manufactured of a different material from the portion of the covering to which it is coupled. The attachment mechanism may be resorbable or nonresorbable. The material of the attachment mechanism may be selected to allow anchoring the covering to an adjacent covering having a complementary attachment mechanism or to another structure. In various embodiments, the attachment mechanism may comprise, allograft, synthetic materials, demineralized bone, nondemineralized bone, other material, or combinations of these. The shape and size of the attachment mechanism may be selected based on application.

In some embodiments, the covering may be tubular and have threaded ends such that the ends may be threaded with a reciprocal thread of a further device or implant. For example, the covering may be used with interference screws. In some embodiments, the covering may include extensions or tabs that may be used for wrapping around or suturing to the surgical site. Alternatively, the covering may be sutured directly to the surgical site. The ends of the covering may be presealed or may be sealed after introduction of contents. Sealing may be done by using adhesives, heating, solvent treatment, suturing, knotting, or any other means.

Spinal Tension Band

Figure 14A:
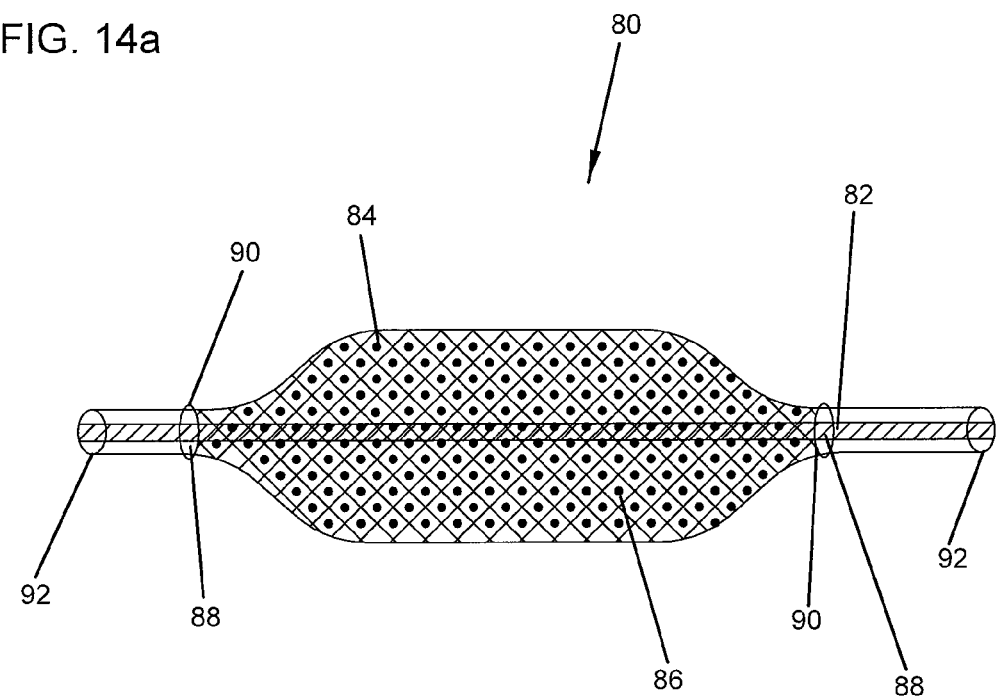
FIG. 14a illustrates a tension band and covering embodiment, in accordance with one embodiment.
Figure 14B:
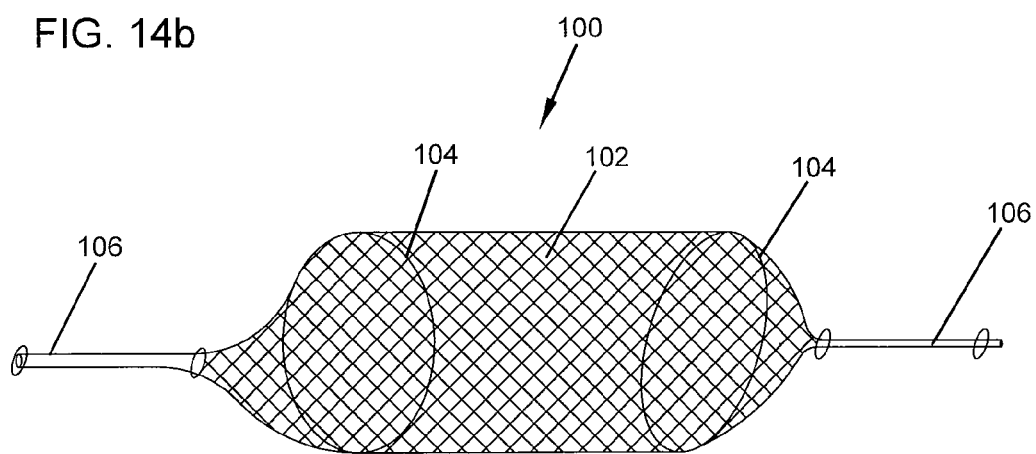
FIG. 14b illustrates tension band comprising covering including spreaders, in accordance with one embodiment.

A further embodiment is shown in FIGS. 14a and 14b. Those figures illustrate an embodiment comprising a tension band including a covering for delivering a substance or material. In accordance with the embodiments shown in FIGS. 14a and 14b, the covering may comprise any of the materials described herein with respect to other embodiments.

Spinal fusion is frequently used as a treatment for various spinal disorders and is achieved by formation of a bony bridge between adjacent vertebral bodies eliminating the intervertebral joint. Spinal fusion can be accomplished within the disc space, anteriorly between adjacent vertebral bodies and/or posteriorly between consecutive processes, e.g., transverse processes, laminae or other posterior elements of the vertebrae.

One frequently used spinal fusion technique involves removal of the intervertebral disc and insertion of an anterior supporting structure, e.g., bone grafts, bone substitutes, plugs, bone dowels, cages, and the like, into the intervertebral disc space to prevent collapse of the disc space and promote fusion of the adjacent vertebrae. To ensure proper growth and fusion between the affected adjacent vertebrae, the posterior side of the spine may be stabilized by utilizing a rigid metallic implant, e.g., a plate, rod, wire or strip, which spans the adjacent vertebrae to re-create a load distribution similar to that of the intact spine. These metallic implants are commonly referred to throughout the relevant scientific and medical literature as "tension bands." U.S. Pat. No. 6,752,831 teaches a biocompatible osteogenic band to stabilize the spine and is herein incorporated by reference in its entirety. As taught therein, the osteogenic band may be fabricated in whole or in part from various materials, particularly connective type biological material obtained from human and animal tissues, plants, and insects which include, but are not limited to, e.g., bone, tendon, ligament, silk, collagen, elastin, reticulin, cellulose, alginic acid, chitosan, small intestine submucosa or combinations thereof. The biological material can be autogenic, allogenic, transgenic, or xenogenic in origin.

FIG. 14a illustrates a tension band and covering embodiment 80 comprising a tension band or cable 82 and covering 84. As shown, the covering structure 84 is provided over the tension band or cable 82. The tension band 82 may comprise an osteogenic material, as described above, or may comprise other suitable material such as synthetic polymer, titanium, stainless steel, or other. The covering structure 84 may be filled with a substance 86, as described herein. In some embodiments, the substance 86 may comprise an osteogenic particulate material. The overall dimensions of the tension band and covering delivery system 80 can vary widely depending on the distance between affected vertebrae, the site, and the method of affixation. In some embodiments, the dimensions of the tension band and covering delivery system 80 may range from about 1 cm to about 1 meter in length, or from about 3 cm to about 8 cm in length, from about 2 mm to about 30 mm in thickness, or from about 2 mm to about 10 mm in thickness, and from about 2 mm to about 30 mm in width, or from about 2 mm to about 10 mm in width.

The tension cable or band 82 includes first and second end portions 88 for coupling with first and second end portions 90 of the covering structure 84. Coupling may be achieved in any suitable manner such as by adhesive, by mechanical coupling, or other. The tension cable or band 82 further comprises first and second ends 92 affixing or coupling to the vertebrae. The ends 92 may be cut or machined to include threads, grooves, driver head, fasteners, rivets, screws, bolts, pins, etc., to aid in affixing each end portion of the elongated section to the vertebrae. The tension cable or band and covering structure delivery system 80, including material, may have dimensions such that, as formed, the system 80 extends between and cover the spinal processes at each end of the system 80. The tension cable or band 82 may be affixed to the spinal processes by any of the mans disclosed in U.S. Pat. No. 6,752, 831.

FIG. 14b illustrates a tension band and covering embodiment 100 wherein the covering 102 includes spreaders 104 such that the covering 102 forms the tension band. In the embodiment shown in FIG. 14a, the covering structure 100 has sufficient strength to support the spine. The spreaders 104 substantially prevent the covering 102 from compressing under load. The covering structure 100 includes first and second ends 106, the ends 106 being formed for affixation to the spinal processes. As shown, the ends 106 may be formed into cable structures. First and second spreaders 104 may be provided proximate first and second ends of the covering structure. The spreaders 104 may have any suitable configuration. In some embodiments, the spreaders may comprise discs. In other embodiments, as shown, the spreaders may comprise rings. The spreaders 104 may be formed of any biocompatible material including, for example, a polymer, a metal, or a natural material such as bone. Generally, flexible spreaders may exhibit less strength under loads.

The tension band and covering embodiments shown in FIGS. 14a and 14b may further comprise a substance or material provided in the covering structure. The substance or material may be osteogenic, such as demineralized bone, provided in fiber, liquefied, particulate, chunk, or monolithic form. The substance or material may be an osteogenic protein or extract in a suitable carrier. Generally, the substance or material may be osteoinductive and/or osteoconductive. The substance or material may be any material described herein for provision in a covering.

Cartridge

Figure 15A:
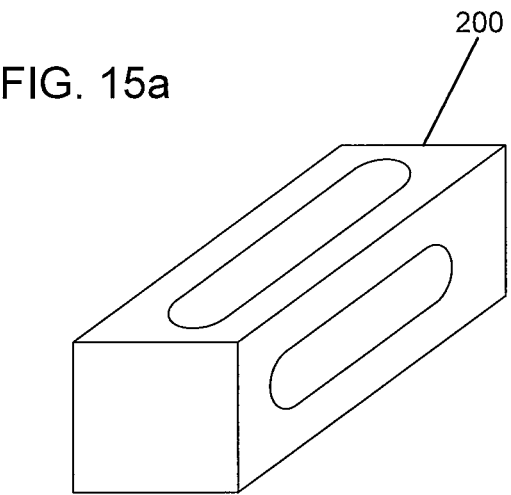
FIG. 15a illustrates a cage for use with a cartridge covering, in accordance with one embodiment.
Figure 15B:
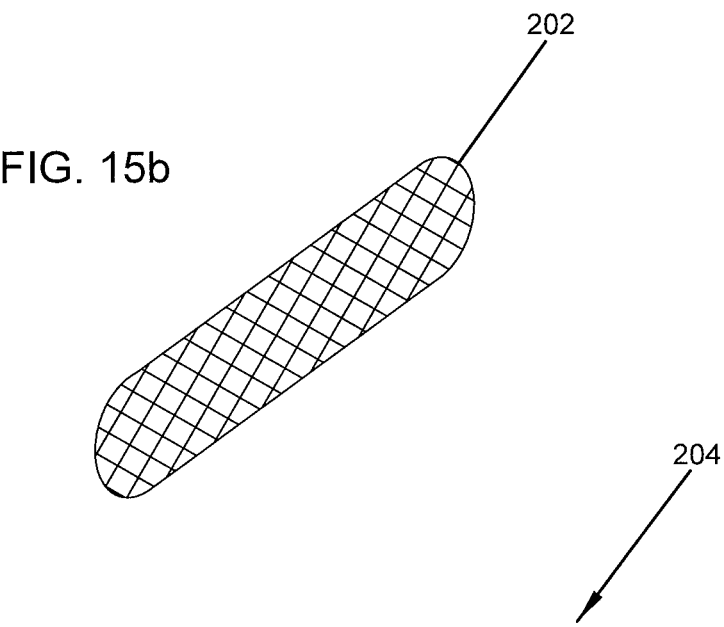
FIG. 15b illustrates a cartridge covering, in accordance with one embodiment.
Figure 15C:
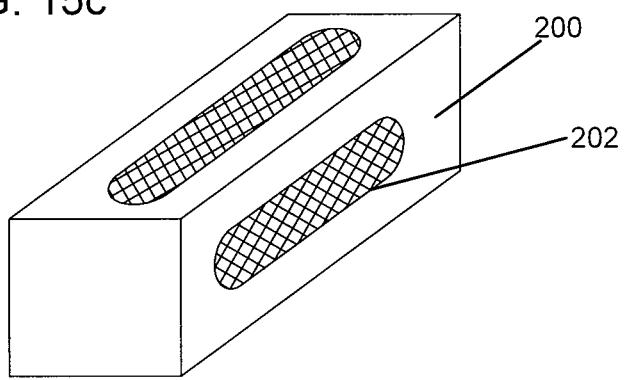
FIG. 15c illustrates a delivery system comprising a cage and a cartridge covering, in accordance with one embodiment.

In various embodiments, a compartment may be configured for placement in a device for use as a delivery system. For example, a cartridge covering may be configured for placement in an interbody fusion cage, in a hip stem, or in other implant devices for delivering a substance. Thus, in some embodiments, the compartment may encourage ingrowth through the implant device. FIGS. 15a-15c illustrate a cage 200, a cartridge covering 202, and a delivery system 204 comprising the cartridge covering 202 in the cage 200, respectively.

In other embodiments, a cartridge covering may form an insert and a second covering may form the implant device for receiving the cartridge covering. The second covering may, in some embodiments, have a structural or mechanical component configured for supporting loads such that the second covering may function as a cage. The cartridge covering may have a biologically active material provided therein.

Figure 16:
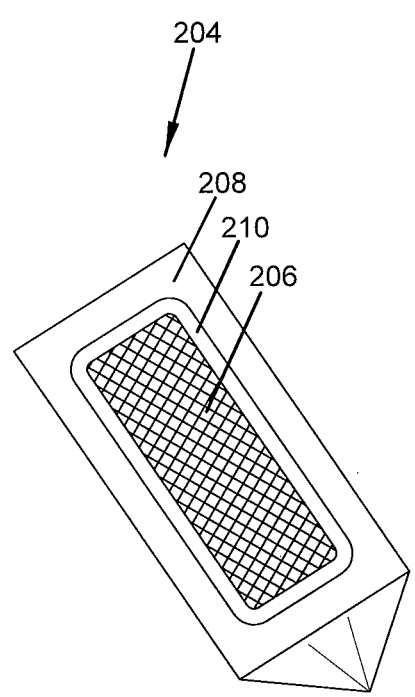
FIG. 16 illustrates a delivery system comprising a cage and a cartridge covering, in accordance with another embodiment.

FIG. 16 illustrates an embodiment of a delivery system 204 wherein the covering comprises a cartridge covering 206 for placement in an interbody fusion cage 208. The interbody fusion cage 208 may be any suitable cage, such as one suitable for anterior lumbar interbody fusion (ALIF), posterior lumbar interbody fusion (PLIF), or other procedure, or may be other suitable implant device. The cage 208 may be formed of metal, polymer, PEEK, biocomposite, allograft, xenograft, other materials, or combinations of these. The cage 208 may have any suitable dimensions. The cage may have substantially solid sides, may have mesh sides, may have slotted sides, may have some open sides and some solid sides, or any combination thereof.

In some embodiments, such as shown in FIG. 16, the cage 208 may be provided with an opening 210 for receiving the cartridge covering 206. The opening 210 may be positioned and sized for receiving the cartridge covering 206 before or after cage placement. Accordingly, the opening 210 may be positioned based on direction of insertion of the cage 208 such that the opening 210 faces the surgeon after insertion of the cage 208. The cartridge covering 206 may be sized and shaped with particularity for the interbody fusion cage 208 or may be selected merely such that it is accommodated by the cage 208, for example by being smaller than the cage 208. A tool may be provided with the cartridge covering for holding the cartridge covering 206 in a position for insertion through the opening 210 of the cage 208 after placement of the cage 208 in vivo.

Figure 17:
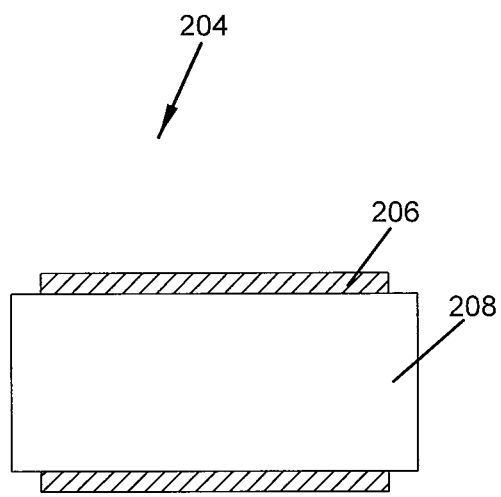
FIG. 17 illustrates a delivery system comprising a cage and a cartridge covering wherein the cartridge covering is oversized with respect to the cage, in accordance with yet another embodiment.

In alternative embodiments, the cartridge covering may be placed in the cage prior to insertion of the cage in vivo. As shown in FIG. 17, the cage 208 may be sized such that the cartridge covering 206 is oversized with respect to the cage 208. In such embodiments, the cartridge covering 206 thus may contact vertebrae when the cage 208 is inserted in vivo.

Figure 18A:
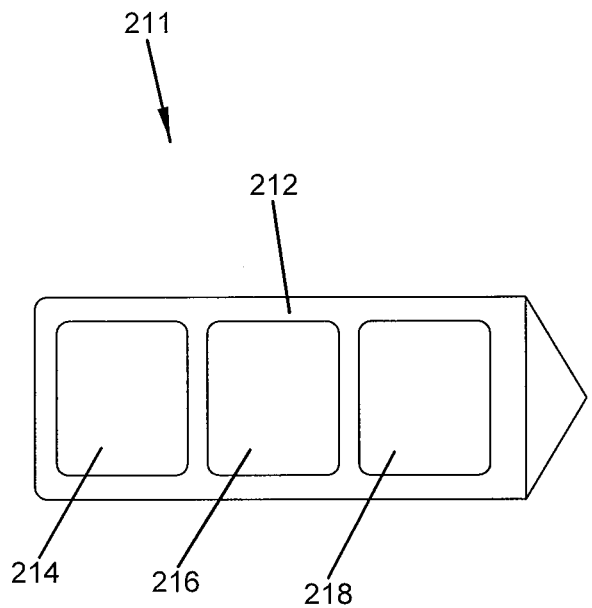
FIG. 18a illustrates a cage with three containment areas for receiving cartridge coverings, in accordance with one embodiment.

In some embodiments, a cage may be provided with containment areas for receiving more than one cartridge covering. In the embodiment of FIG. 18a, the delivery system 211 comprises a cage 212, including three containment areas 214, 216, and 218, and corollary cartridge coverings for placement in each containment area. As shown, the containment areas 214, 216, and 218 may be generally uniformly sized and shaped. Alternatively, the containment areas 214, 216, and 218 may have varying sizes or shapes and/or varying materials characteristics. The materials provided in the cartridge coverings provided in each containment area may vary depending on the general position of the cartridge covering as placed in vivo. Thus, for example, a different material may be provided in a cartridge covering for placement in containment area 214 than in a cartridge covering for placement in containment area 216. Further, in some embodiments, a plurality of cartridge coverings may be provided in a single containment area.

Figure 18B:
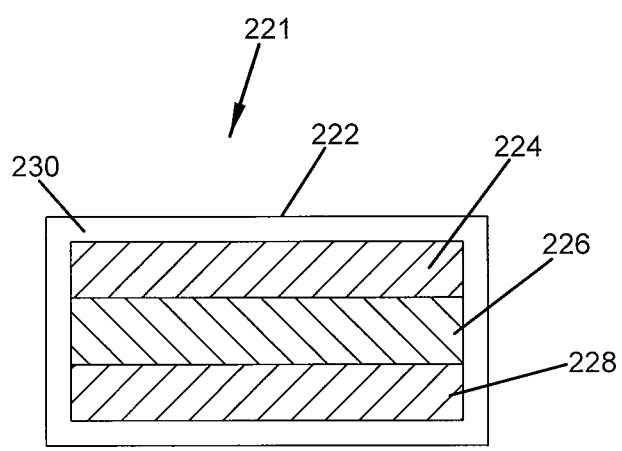
FIG. 18b illustrates a delivery system comprising a cage and three cartridge coverings, in accordance with one embodiment.

FIG. 18b illustrates an alternative embodiment of a cage delivery system 221 comprising a cage 222 having a plurality of cartridge coverings 224, 226, 228 provided therein. In the embodiment of FIG. 18b, a single containment area 230 is provided with three cartridge coverings 224, 226, 228 provided therein. The cartridge coverings 224, 226, 228 are provided generally vertically stacked. The coverings may be provided in any desired configuration. Thus, as placed in vivo, the top and bottom cartridge coverings 224 and 228 are closest to host bone. Thus, the top and bottom cartridge coverings 224 and 228 may have osteoconductive materials provided therein. In contrast, the middle cartridge covering 226 is separated from host bone by the top and bottom cartridges 224 and 228. Thus, for example, osteoinductive materials may be provided in the middle cartridge covering 226. In alternative embodiments, separate containment areas may be provided for each of the cartridge coverings 224, 226, 228.

In some embodiment, it may be useful to provide a cage having specific characteristics. For example, the cage may be provided with openings, via mesh structure, slots, or other, on surfaces generally adjacent vertebrae to encourage ingrowth through the cage to the covering cartridge within the cage. Further, the cage may be specifically configured for accommodating a cartridge covering, for enhancing specific characteristics of a material delivered by the cartridge covering, or other. In some embodiments, the cage may be formed to increase exposure area to the interior of the cage such that exposure of the cartridge covering within the cage is enhanced. Thus, exposure of the cartridge covering to the vertebral body may be enhanced.

Figure 19:
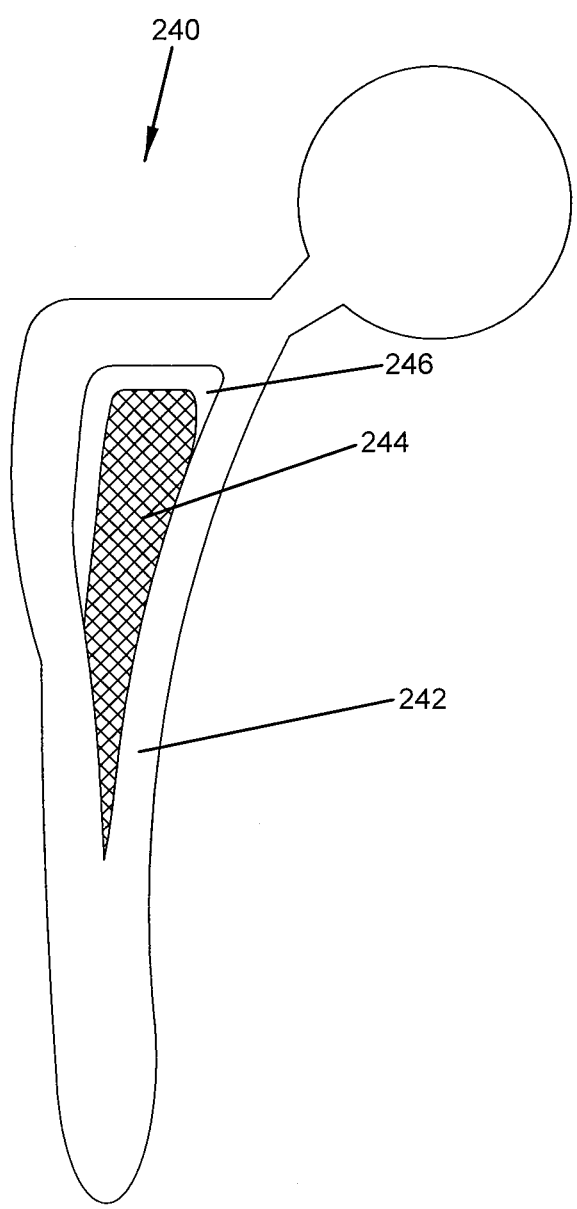
FIG. 19 illustrates a delivery system comprising a hip stem and a cartridge covering, in accordance with one embodiment.

It is to be appreciated that such cartridge coverings may be provided for placement in any suitable implant device for delivering a material in vivo or for enhancing healing of the body, such as via bone ingrowth through the implant. Thus, as shown in FIG. 19, in yet a further embodiment, a delivery system 240 may comprise a hip stem 242 and a cartridge covering 244 for delivery of material in the hip stem 242 to encourage ingrowth to the stem. Accordingly, the hip stem 242 may include a window 246 for receiving the cartridge covering 244. Osteoinductive and/or osteoconductive materials may be provided within the cartridge covering. For example, in one embodiment, DBM may be provided within the cartridge covering 244.

Coverings such as disclosed herein may further be useful in osteonecrosis. In osteonecrosis of the femoral head, one treatment method comprises drilling a hole through the trochanter and through the femoral neck, into the femoral head. This drill hole may be grafted, for example using graft material in a tube implant device. In certain embodiments, coverings may be filled (pre-filled or filled by the surgeon) with graft materials for insertion in the drill tract directly or for insertion into a tube implant device for placement in the drill tract. The covering may be dimensioned for delivery into the tube implant device or through the drill tract, for example generally long and thin. In further embodiments, a thread may be provided on an end of the covering to assist in loading of the covering into, for example, a tube for placement in the drill tract. Alternatively, the covering may be provided as a series of small coverings and these coverings iteratively placed into the tube or drill tract. Using a covering such as provided herein, the procedure for placing the covering in osteonecrosis may be minimally invasive or open.

In some embodiments, cartridge coverings may be used with an implant such as a mechanical or structural support device to deliver materials in weight-bearing applications. The cartridge covering facilitates spatially controlled delivery of materials.

Cartridge coverings may be provided singly or in series. For example, a series of cartridge coverings may be provided in a manner similar to the embodiment of tubular covering 120 of FIG. 20, described further below. Generally, the wrapping covering may be formed of any materials discussed with respect to other covering embodiments described herein.

Any of the materials described herein may be provided in the cartridge covering. In specific embodiments, a collagen sponge may be provided in a cartridge covering and the cartridge covering delivered in the cage or implant. Materials such as BMP-2 may be added to the material, may be injected into the material, or may be the primary material for delivery by the cartridge covering. Other bioactive agents and bioactive compounds may be used, as desired.

Wrapping

Figure 21A:
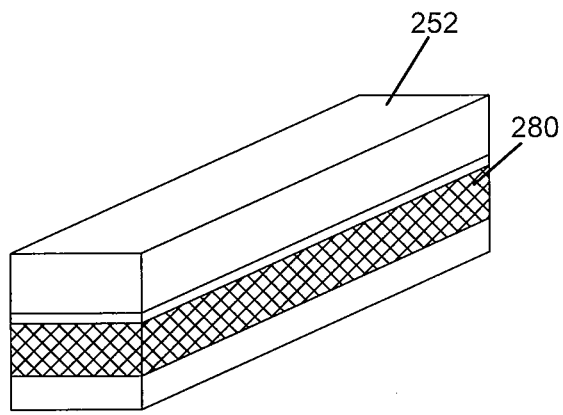
FIG. 21a illustrates a delivery system comprising a cage and a wrapping covering, in accordance with one embodiment.
Figure 21B:
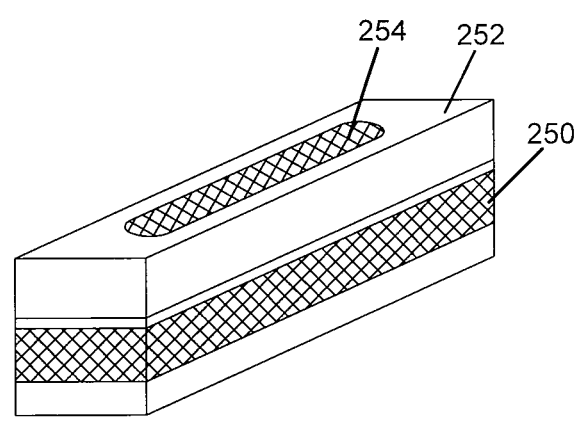
FIG. 21b illustrates a delivery system comprising a cage, a cartridge covering, and a wrapping covering, in accordance with one embodiment.

In accordance with further embodiments, a covering may be provided for wrapping around an implant, such as a cage. Thus, for example, as shown in FIG. 21*a*, a wrapping covering 250 may be wrapped around a cage 252. Further, as shown in FIG. 21*b*, a cartridge covering 254 may be placed within the cage 252, as described above, and a wrapping covering 250 wrapped around the cage 252. In some embodiments, the wrapping covering 250 may comprise an elastic mesh containment ring. In alternative embodiments, the wrapping covering 250 may be formed of any materials discussed with respect to other covering embodiments described herein. The wrapping covering may be wrapped around the cage before or after insertion of the cage in vivo. Wrapping of the covering 250 may comprise extension (and subsequent retraction) of an elastic wrapping covering around the cage, may comprise tying of a wrapping covering around the cage, may comprise hooking of a wrapping covering on hooks or other coupling mechanisms on the cage, or other. Further, the wrapping covering 250 may extend around the entire cage 252 or over only a portion of the cage 252. While specific reference is made herein to a wrapping covering wrapped around a cage such as an interbody fusion cage, it is to be appreciated that such wrapping covering may be used with any suitable implant.

In further embodiments, an implant may be fit within a covering. For example, in joint revision surgeries, a covering may be provided in a defect created by removal of an original implant and cement from the implant and a revision implant may be placed centrally of the covering.

In yet further embodiments, a covering may be provided surrounding another structure. For example a covering may be provided around a cylinder configured for receipt in a long bone segmental defect, such as in trauma or tumor situations. The covering may hold a graft and maintain the graft in the defect, excluding soft tissue, to provide apposition to the segment ends.

Curved

In some embodiments, a delivery system such as provided herein may comprise a curved covering. In some embodiments, the curved covering may have a shaping or reinforcing structure. In some embodiments, the shaping or reinforcing structure may be resorbable. Such shaping or reinforcing structure may be, for example, a rod or wire. The shaping or reinforcing structure may be formed out of metal or other radiographic material such that it may act as a radiographic marker. The shaping or reinforcing structure may be removed after delivery device placement or may be kept in place. In some embodiments, the shaping or reinforcing structure may add rigidity to the covering device and thus facilitate impaction into a defect. In some embodiments, a substantially straight shaping or reinforcing structure may be provided in a covering to act as a radiographic marker or as an instrument interface. In some embodiments, the curved covering may be preassembled or formed with a resorbable shaping or reinforcing structure.

FIG. 21*c* illustrates an embodiment of a curved covering with a shaping or reinforcing structure. As shown, the curved covering 1030 may have a central containment portion 1032 and first 1036 and second end portions 1038. The central containment portion 1032 may be filled with a substance for delivery. The end portions 1036, 1038 may be unfilled. A shaping or reinforcing structure 1034 such as a rod, bar, or wire is provided along the containment portion 1032, for example centrally on the containment portion 1032 and running from a first end portion 1036 to a second end portion 1038, for forming the covering into the curved shape.

Figure 21D:
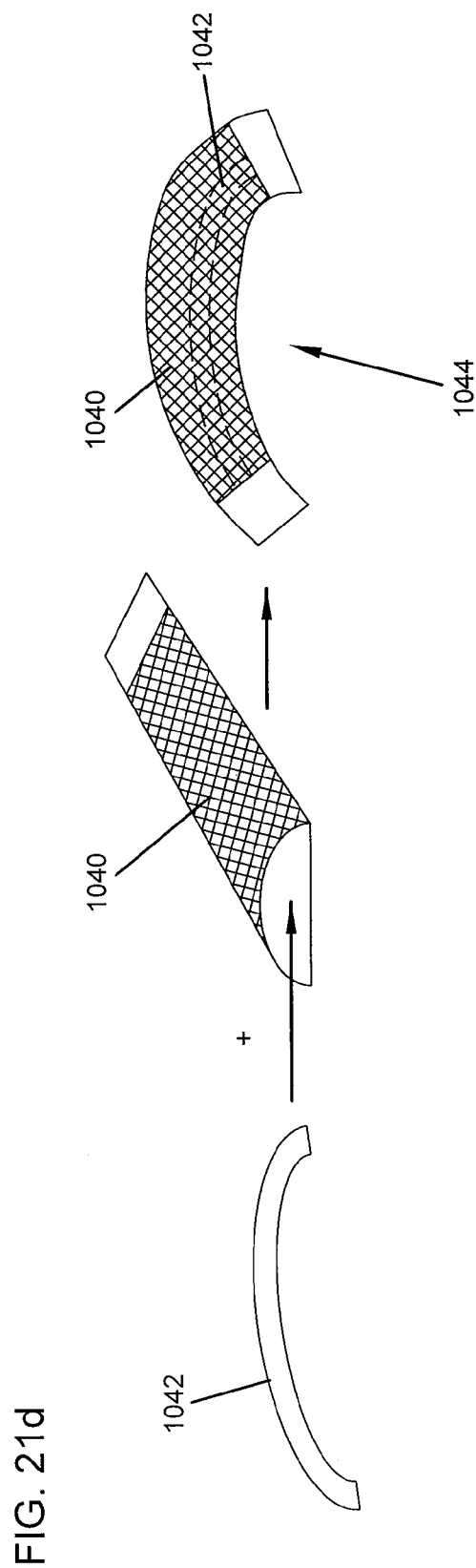
FIG. 21d illustrates a top view of assembly of the curved covering of FIG. 21c.
Figure 21E:
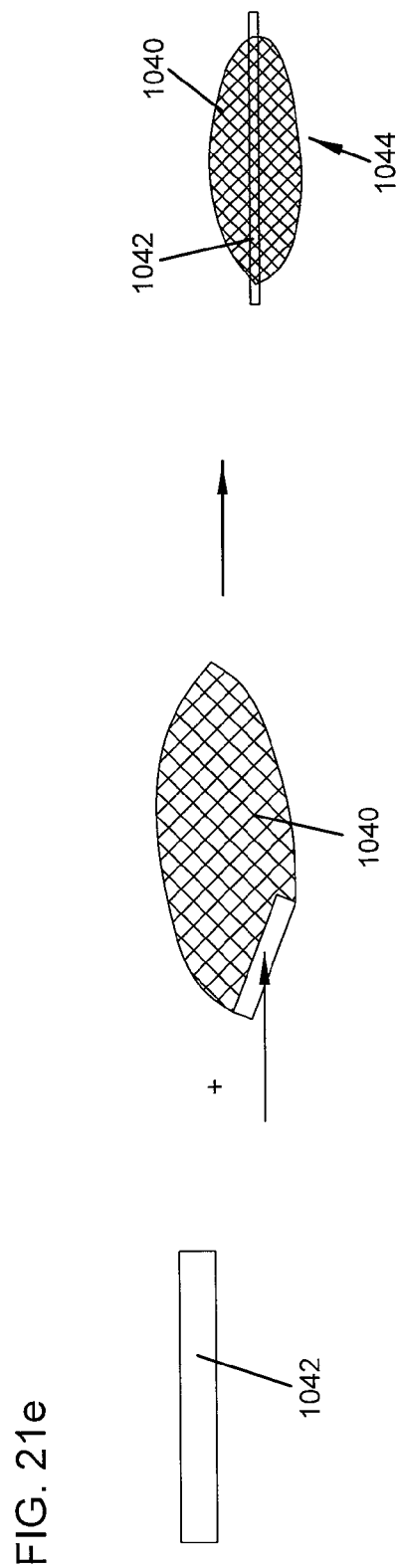
FIG. 21e illustrates a side view of assembly of the curved covering of FIG. 21c.

FIG. 21*d* illustrates a top view of assembly of the curved covering of FIG. 21*c*. FIG. 21*e* illustrates a side view of assembly of the curved covering of FIG. 21*c*. As may be appreciated, a covering 1040 is provided and a shaping or reinforcing structure 1042 is provided. The covering 1040 may be provided in a filled or unfilled condition. Generally, the covering 1040 and the shaping or reinforcing structure 1042 may have complementary lengths. In the embodiments shown, the covering 1040 and reinforcing structures 1042 have approximately equal lengths. In other embodiments, the shaping or reinforcing structure may be longer than the covering such that, after assembly, the shaping or reinforcing structure extends beyond at least one end of the covering. As shown, the shaping or reinforcing structure 1042 is combined with the covering 1040 to form a curved covering 1044. Such combination 1044 may be in any suitable manner including placement of the shaping or reinforcing structure 1042 in the covering 1040, threading of the shaping or reinforcing structure 1042 through the covering 1040, adherence of the shaping or reinforcing structure 1042 on the covering 1040, or other.

Cup Shape

Figure 22A:
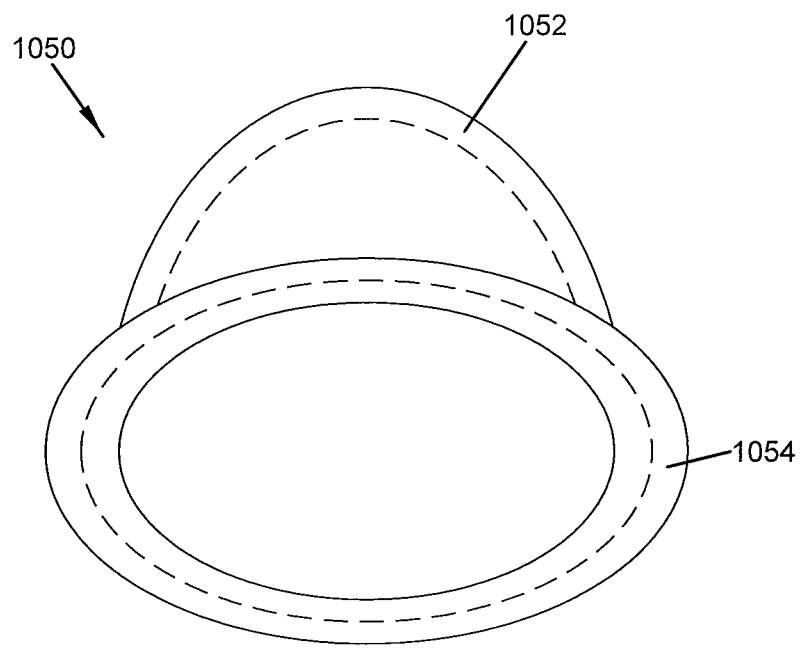
FIG. 22a illustrates a cup-shaped embodiment of a covering, in accordance with one embodiment.
Figure 22B:
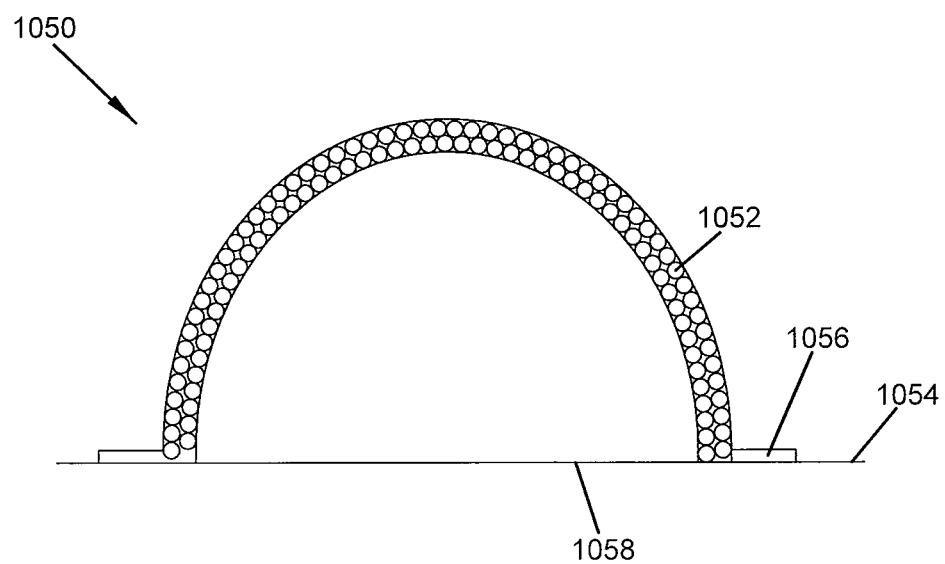
FIG. 22b illustrates another view of a cup-shaped embodiment of a covering with a flange extending at least partially around the rim of the covering, in accordance with one embodiment.

FIGS. 22*a* and 22*b* illustrate a cup-shaped embodiment. As shown, the covering 1050 may have a substantially cup-shaped configuration comprising a first layer 1052 and a second layer 1054. The first layer 1052 and the second layer 1054 may be coupled together along a rim 1058 of the covering 1050. Such coupling may be done, for example, by suturing the first layer 1052 and the second layer 1054 together. The covering may further include a flange 1056 extending at least partially around the rim 1058 of the covering 1050 and formed by the coupled first layer 1052 and second layer 1054. Graft material or other substance may be provided between the first layer 1052 and the second layer 1054.

Pad

In accordance with further embodiments, a delivery system such as provided herein may be used to deliver a layer of osteoinductive and/or osteoconductive material to encourage ingrowth of bone. For example, a compartment may be configured for delivering a mat of DBM underneath a tibial tray in a total knee replacement to encourage ingrowth. In accordance with such an embodiment, the covering may deliver DBM or other graft material. In some configurations, the covering may capture fibers of DBM but allow protrusion of some of the fibers. Alternatively, a compartment may be configured as a pad for applications such as building up a cheekbone for plastic surgery, as a cranioplasty covering, or other.

Figure 23:
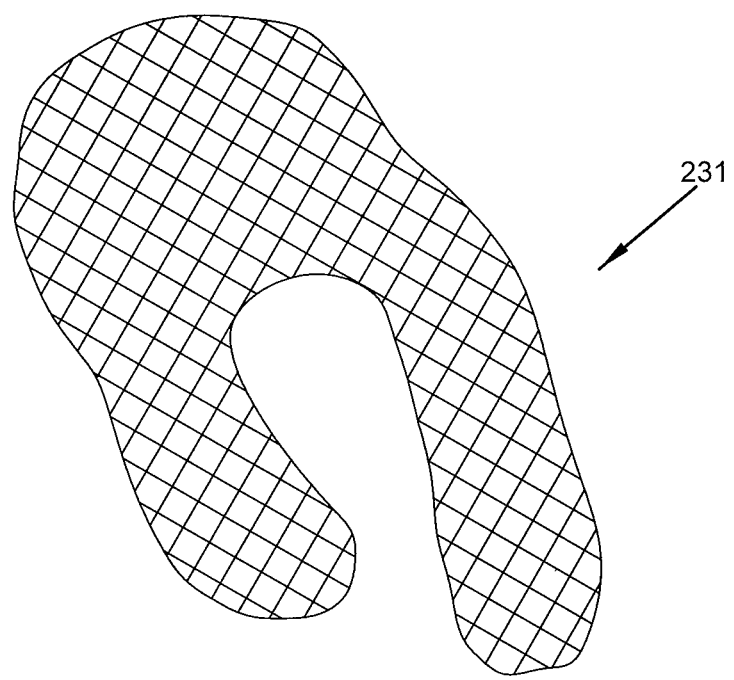
FIG. 23 illustrates a U-shaped covering, in accordance with one embodiment.

In a further pad or mat embodiment, a delivery system such as provided herein may be formed as a mat for use in the occipital/cervical region of the spine. A covering for such delivery system may be substantially U-shaped and generally configured to fit the cranio-cervical junction. In certain embodiments, the covering may be filled with BMP or similar material. Such covering may be useful for fusion from C1-C2. FIG. 23 illustrates a U-shaped pad 231.

In accordance with some embodiments, a covering may be used in a cemented total joint arthroplasty. The covering, with material provided therein, may be used to create a lining between a cement mantle and the host tissue.

Solid Covering

Figure 24A:
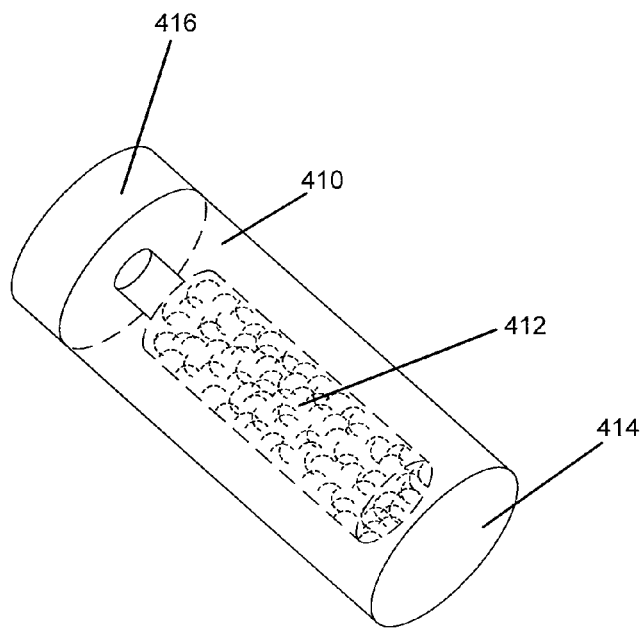
FIG. 24a illustrates a substantially solid delivery container covering, in accordance with one embodiment.
Figure 24B:
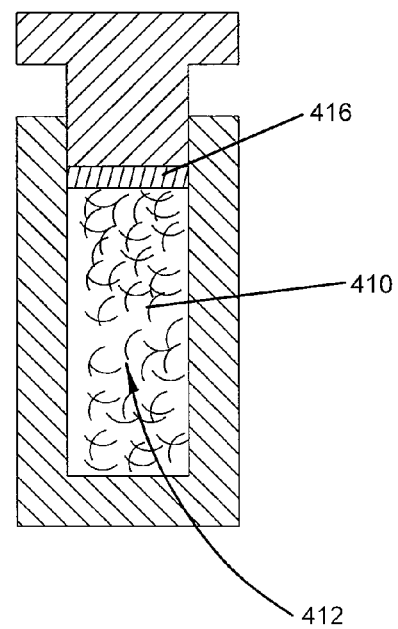
FIG. 24b illustrates a cap interlocking with a tube of a substantially solid delivery container covering via press fitting.

In some embodiments, the covering may be a substantially solid delivery container. FIG. 24*a* illustrates such a covering. The graft material may be, for example, a mixture of demineralized bone particles and pressed bone fibers. In some embodiments, the graft material may further include an antibiotic, drug powder, or other material(s) such as disclosed herein. The covering 410 may be a generally tubular body formed of, for example, a polymer such as disclosed in U.S. Pat. No. 6,696,073 and U.S. patent application Ser. No. 11/625,086 (published as US2008/0069852), herein in incorporated by reference in their entireties. Alternatively, other polymers or other materials may be used. The graft material 412 may be placed in the covering 410. A first end 414 of the covering 410 may be sealed in a non-removable fashion (such as by forming the tube with a closed end) and a second end of the covering may have a removable cap 416. The cap 416 may interlock with the tube 410 via threading, a press fit, or other. FIG. 24*b* illustrates the cap 416 being press fit on a covering 410 holding graft material 412. The covering may be factory assembled with the graft material therein or may be intraoperatively assembled.

Figure 24C:
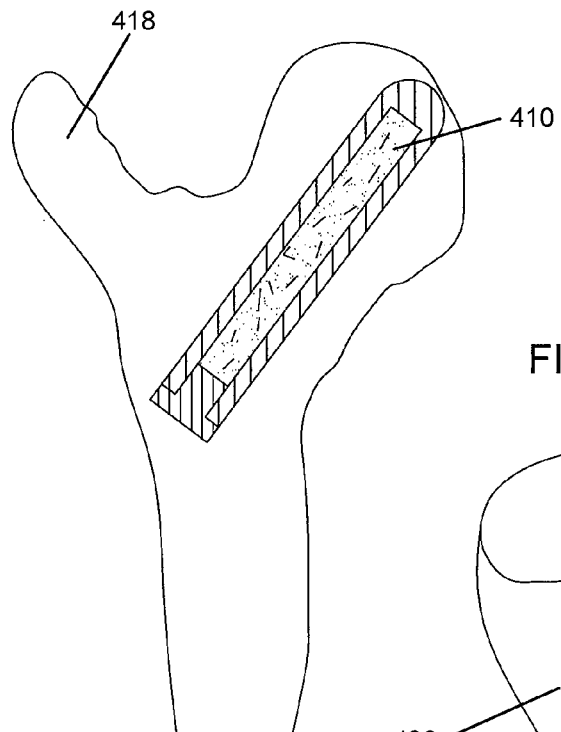
FIG. 24c illustrates a solid delivery container covering used in femoral head AVN, in accordance with one embodiment.
Figure 24D:
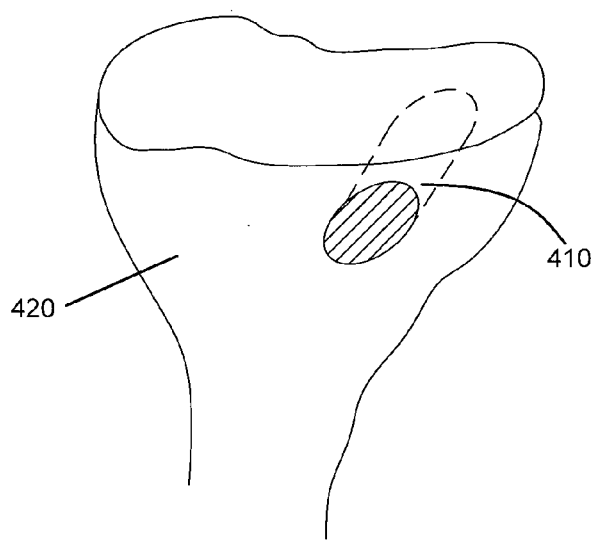
FIG. 24d illustrates a solid delivery container covering used in treatment of a tibial compression fracture, in accordance with one embodiment.
Figure 24E:
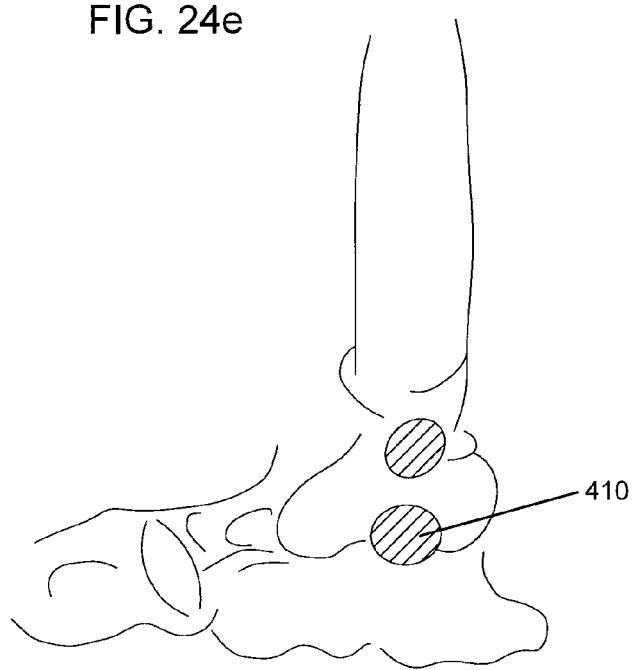
FIG. 24e illustrates a solid delivery container covering used in ankle fusion, in accordance with one embodiment.

FIGS. 24*c*-24*e* illustrate example applications of such a covering. As shown in FIG. 24*c*, the substantially solid covering 410 may be used in femoral head avascular necrosis 418. As shown in FIG. 24*d*, the substantially solid covering 410 may be used in treatment of a tibial 420 compression fracture. As shown in FIG. 24*e*, the substantially solid covering 410 may be used in joint fusion, such as ankle fusion. Joint fusion, including ankle fusion, generally comprises decorticating the articular surface of the joint to be fused and drilling a hole that encompasses faces of each of the two adjacent bones to be fused. A delivery system, including covering and graft material for example, such as disclosed herein may be placed into the drilled hole, such that both bones are contacted.

Shapes and Configurations

As discussed herein, coverings may be provided in a plurality of shapes and generally may be configured for desired applications. Coverings may be configured for receipt directly in vivo or for placement in an implant device. The size and shape, as well as material from which it is manufactured, may be selected for a desired application. Generally, a covering may be provided as a plug (such as a cylinder with a tapered or blunt end), as a generally flat mat (with captured particles or woven to surround a generally flat plane of material), as a tube, a snake (generally long tube, such as may be subdivided), as a block, as a sphere, as an ovoid, as a molded shape (geometric, such as based on an atomic CT or other scan), as a U-shape, as an L-shape, as a tape, as a film, or shaped to substantially mimic a skeletal bone. In further embodiments, a covering may be provided in other configurations such as a sealed, perforated film, as a twin compressing fibers or other materials, as a resorbable container or capsule, or as a cage or container such as providing mechanical support.

Packing

The substance may be packed in the covering at any suitable density. For some applications, the substance may be loosely packed in the covering to enhance manipulability. In some embodiments, the material may be packed in the covering such that the covering retains flexibility and may be folded over itself. In other applications, the substance may be tightly packed in the covering to provide a relatively stiff delivery system, and it may be weight bearing.

Figure 24F:
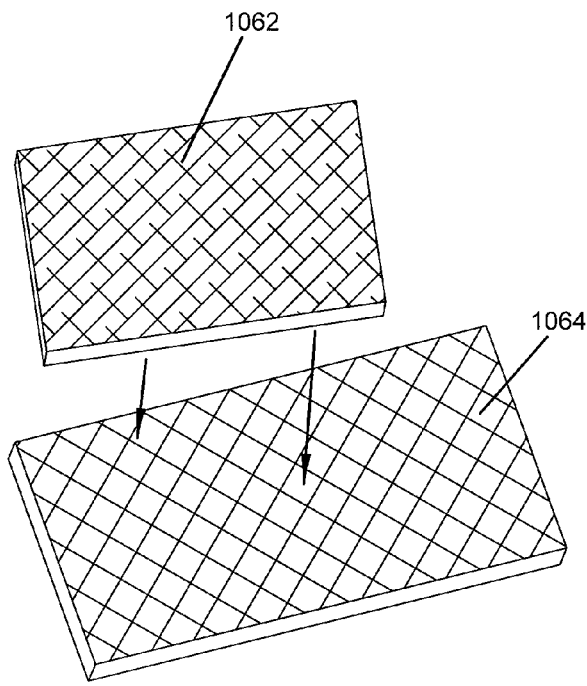
FIG. 24f illustrates the assembly of a covering comprising two layers of material, in accordance with one embodiment.
Figure 24G:
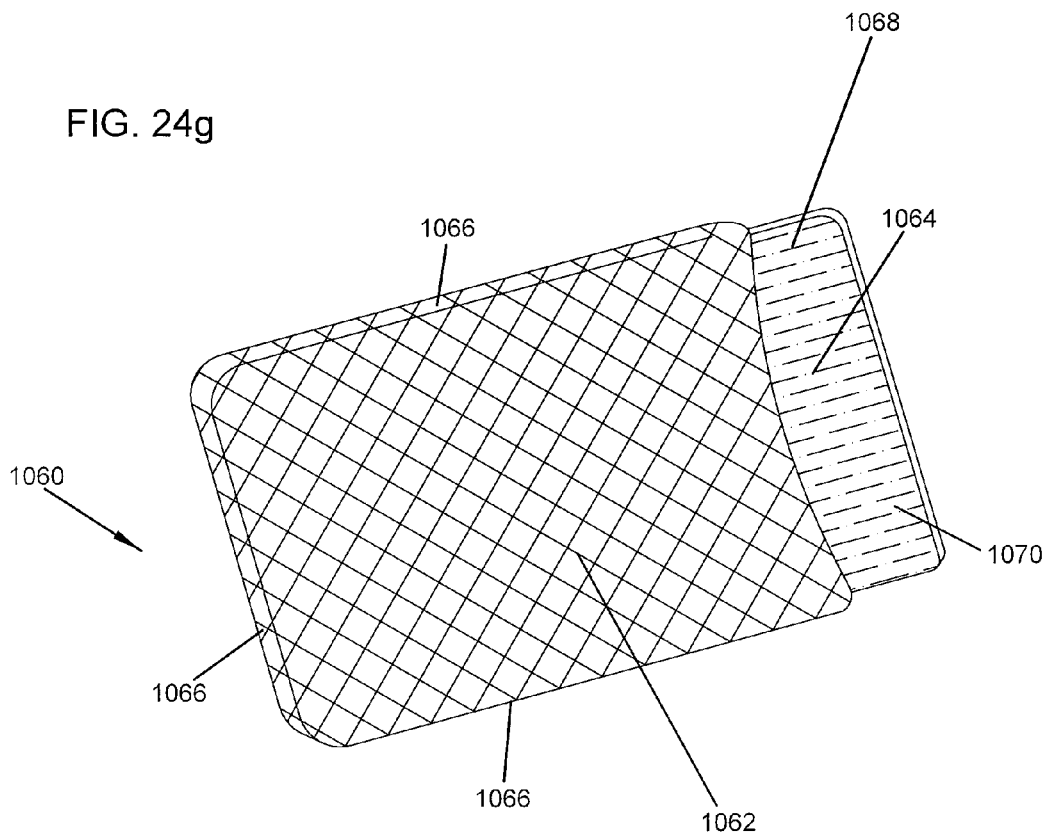
FIG. 24g illustrates a coving comprising two layers of material that is open at one end, in accordance with one embodiment.

In some embodiments, the covering may be configured to facilitate placement of graft material in the covering. Thus, for example, FIGS. 24*f* and 24*g* illustrate a covering 1060 comprising two layers 1062, 1064 of material. The two layers 1062, 1064 of material meet one another to form four sides of the covering. Three of the sides are sealed 1066. The fourth side 1068 is unsealed. At the fourth side 1068, one layer of material 1064 has a length more than the other layer of material 1062. Thus, a fold-over tab 1070 is formed. The covering 1060 may be opened to add or remove materials from the covering 1060. In some embodiments, the fold-over tab 1070 may be sutured, crimped, or otherwise manipulated to fixedly close the covering 1060. It is to be appreciated that the fold-over tab 1070 also facilitates adjustability of the size of the bag. Thus, for example, the fold-over tab 1070 may be used to fold a portion of the covering 1060 including both layers of material 1062, 1064 to reduce the size of the covering 1060. Accordingly, the embodiment of FIGS. 24*f* and 24*g* may be used to manipulate the size of the covering 1060 or volume of materials inside of the covering 1060.

IV. Substance for Delivery by Covering

A substance is provided in the covering, before or during surgery (as described below), for delivery in vivo. Generally, the substance or material may be homogenous or heterogeneous. The substance or material may be selected to exhibit certain gradients. For example, the substance or material may be selected to exhibit a gradient to guide, lure, or attract cells along a pathway. Such gradient may comprise a cell gradient, a cell type gradient (for example transitioning from bone cells to cartilage cells or transitioning from bone cells to tendon cells), a gradient of conductivity, or a gradient of density/porosity. In some embodiments, the substance or material may comprise a sequence of ingredients.

The covering may be used to deliver a substance comprising any suitable biocompatible material. In specific embodiments, the covering may be used to deliver surface demineralized bone chips (cortical or cancellous), optionally of a predetermined particle size, demineralized bone fibers, optionally pressed, and/or allograft. For embodiments wherein the substance is biologic, the substance may be autogenic, allogenic, xenogenic, transgenic, or combinations of these. Each of these tissue types includes any tissue of bone origin, connective tissue origin, or any collagen containing material including organ tissues. Other suitable materials that may be positioned in the covering include, for example, protein, hormones, nucleic acid, carbohydrate, lipids, collagen (autograft, allograft, or xenograft from musculoskeletal or organ systems), allograft bone, autograft bone, cartilage stimulating substances, allograft cartilage, TCP, TCP/calcium sulfate, calcium carbonate, calcium phosphates, bioactive glasses, glass ceramics, magnesium phosphates, phosphates containing any biocompatible metal ion, porous implants of all types including trabecular metal, biocompatible metals including stainless steel, cobalt-chrome, titanium, titanium alloys, polymers such as polylactic acid, polyglycolic acid, polycaprolactone, polyglycolide-co-caprolactone, polyethylene oxide, polypropylene oxide, polyglycolide-co-trimethylene carbonate, poly(lactic-co-glycolic acid), poly-L-lactide, polyethylene glycol, polyetheretherketones, polyurethanes, polyethers of all types, poly ethylene terephthalte, polyethylene, polypropylene, Teflon, chondroitin sulfate, hyaluronic acid and its salts, chitosan and derivatives, natural polymers such as silk, collagen, polysaccharides, polyhydroxyalkanoates, polymers combined with bone or collagen or both from any source (allograft, xenograft, transgenic, autograft), hydroxyapatite, calcium sulfate, polymer, nanofibrous polymers, growth factors, carriers for growth factors, growth factor extracts of tissues, demineralized bone matrix, dentine, bone marrow aspirate, bone marrow aspirate combined with various osteoinductive or osteoconductive carriers, concentrates of lipid derived or marrow derived adult stem cells, umbilical cord derived stem cells, adult or embryonic stem cells combined with various osteoinductive or osteoconductive carriers, transfected cell lines, bone forming cells derived from periosteum, combinations of bone stimulating and cartilage stimulating materials, committed or partially committed cells from the osteogenic or chondrogenic lineage, platelets, activated platelets, antibiotics, substances with antimicrobial properties, or combinations of any of the above. In accordance with one embodiment, the substance is a bone matrix compositions such as described in U.S. patent application Ser. No. 12/140,044 and U.S. Patent Publications Nos. 2007/0098756 and 2007/0110820 all for Bone Matrix Compositions and Methods, herein incorporated by reference in their entireties. Suitable materials for preparing biocomposites for placement in the covering are disclosed in U.S. Patent Publication Nos. 2007/0191963, 2006/0216323, and 2005/0251267, U.S. Pat. Nos. 6,696,073, 6,478,825, 6,440,444, and 6,294,187, all herein incorporated by reference in their entireties for all purposes.

In some embodiments, the substance or material for delivery may comprise a biodegradable polyester such as poly (lactic acid) (PLA), poly(glycolic acid) (PGA), poly(lactic-co-glycolic acid) (PLGA), or polyhydroxyalkanoates (polyhydroxybutyrates and polyhydroxyvalerates and copolymers), polysaccharides, polyhydroxyalkanoates, polyglycolide-co-caprolactone, polyethylene oxide, polypropylene oxide, and polyglycolide-co-trimethylene carbonate. In some embodiments, poly(ethylene glycol) (PEG) may be incorporated into the biodegradable polyester to add hydrophilic and other physico-chemical properties to enhance drug delivery. In some embodiments, composites of allograft bone and biodegradable polymers (for example, PLEXUR® products available from Osteotech) may be delivered by the covering.

In some embodiments, the substance may be pressed before placement in the covering. A substance provided within the covering may be homogenous, or generally a single substance, or may be heterogeneous, or a mixture of substances. In some embodiments, the substance may be designed to expand in vivo. U.S. Patent Publications No. 2008/0091270 describes an osteoimplant that expands in vivo and is herein incorporated by reference in its entirety. Such an embodiment may be used to fill a space and create contact with congruent surfaces as it expands in vivo, for example for interbody fusion. Thus, in some embodiments, the delivery system may be used in the disc space, between implants, or inside a cage.

The covering retains the substance in place by pressure against the covering. The covering thus may, in some embodiments, maintain particles of substance in close proximity (for example, where the covering retains a substance comprising bone particles). Generally, the ratio of covering material to substance for placement within the covering may be low. For example, in some embodiments, the ratio of covering material to substance, by weight, may be approximately 1:1,000, 1:100, 1:50, 1:25, 1:1, or any suitable ratio that may be higher or lower than these.

In some embodiments the substance delivered by the covering may include or comprise an additive such as an angiogenesis promoting material or a bioactive agent. It will be appreciated that the amount of additive used may vary depending upon the type of additive, the specific activity of the particular additive preparation employed, and the intended use of the composition. The desired amount is readily determinable by one skilled in the art. Angiogenesis may be an important contributing factor for the replacement of new bone and cartilage tissues. In certain embodiments, angiogenesis is promoted so that blood vessels are formed at an implant site to allow efficient transport of oxygen and other nutrients and growth factors to the developing bone or cartilage tissue. Thus, angiogenesis promoting factors may be added to the substance to increase angiogenesis. For example, class 3 semaphorins, e.g., SEMA3, controls vascular morphogenesis by inhibiting integrin function in the vascular system, Serini et al., *Nature*, (July 2003) 424:391-397, incorporated by reference herein, and may be included in the recovered hydroxyapatite.

In accordance with some embodiments, the substance may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; demineralized bone powder as described in U.S. Pat. No. 5,073,373; collagen, insoluble collagen derivatives, etc., and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin; bacteriaphages; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; antispasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases, etc.; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other means; tissue transplants; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immunosuppressants; permeation enhancers, e.g., fatty acid esters such as laureate, myristate and stearate monoesters of polyethylene glycol, enamine derivatives, alpha-keto aldehydes, etc.; and nucleic acids.

In certain embodiments, the bioactive agent may be a drug. In some embodiments, the bioactive agent may be a growth factor, cytokine, extracellular matrix molecule, or a fragment or derivative thereof, for example, a protein or peptide sequence such as RGD. A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996; and the United States Pharmacopeia-25/National Formulary-20, published by the United States Phannacopeial Convention, Inc., Rockville Md., 2001.

In one embodiment of a covering comprising two compartments, a first growth factor may be provided for delivery by the first compartment and a second growth factor may be provided for delivery by the second compartment. The first and second growth factors may be provided with other substances. The first and second growth factors may be selected (and placed in respective compartment for positioning in vivo) based on desired characteristics of the growth factor. For example, an angiogenic growth factor may be provided in the first compartment and an osteoinductive growth factor may be provided in the second compartment.

Similarly, the substance delivered by the first compartment and the substance delivered by the second compartment may be selected based on desired characteristics of the compartment according to its placement in vivo. Thus, for example, one compartment may have a substance that is substantially osteoclast stimulating while another compartment may have a substance that is substantially osteoblast stimulating.

In one embodiment, demineralized bone fibers may be provided in the first compartment and surface demineralized bone chips may be provided in the second compartment. In this embodiment, the demineralized bone fibers may generally provide osteoinductive characteristics and the surface demineralized chips may generally provide osteoinductive and/or osteoconductive characteristics. In use, the covering may be laid flat on the transverse process and positioned such that the first compartment, holding the demineralized bone fibers, is nearest the vertebral body and the second compartment, holding the surface demineralized bone chips, is farther from the vertebral body, or the compartments may be positioned in any other desired configuration. In another embodiment, a covering may comprise first and second compartments wherein autograft may be placed in one of the compartments prior to placement of the covering in vivo, described more fully below. In other embodiments, three or more compartments may be used, as appropriate for the materials being delivered and the application of the compartmented implant. More than one substance may be provided in a compartment. For example, surface demineralized bone chips and demineralized bone fibers may be mixed and provided within a single compartment. Such mixture of substances within a single compartment may be a substantially uniform mix or may be a plurality of substances placed in the compartment separately such that they are substantially unmixed. When multiple compartments are used, each compartment may contain one or more substances. Exemplary substances that may be provided in one or more compartments of the delivery system include cells from the osteogenic precursors, growth factors, angiogenic factors and other active proteins including bone morphogenic proteins, and cellular scaffolding materials of natural or synthetic origin, antibiotics, and other substances described below.

In some embodiments, other medical devices may be provided within the covering. For example, one or more electrical stimulator electrodes may be provided within the covering.

Generally speaking, any suitable substance or material may be delivered using coverings as provided herein. Such substances may include bone, cartilage, tendon, ligament, muscle, skin, nerve, collagen, calcium sulfate ($CaSO_4$), calcium phosphate ($CaPO_4$), betaTCP, hydroxyapatite, bioglass, silicon-containing calcium phosphates, cells, autograft, or other.

Particulate Substance

In some embodiments, a particulate substance may be delivered by the covering. For example, the covering may be used to delivery a particulate bone graft.

Growth Factors or Other Active Substances

Figure 24H:
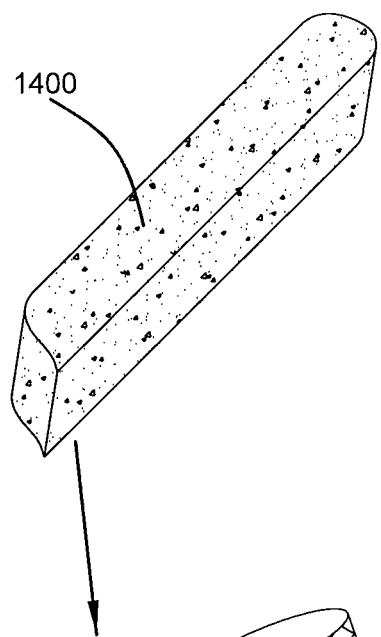
FIG. 24h illustrates a carrier that may be inserted into a covering, in accordance with one embodiment.

Growth factors or other active substances may be delivered by the covering. Active substances may include, for example, growth factors such as BMP-2 (Infuse) and/or other growth proteins, as well as drugs, antibiotics, etc. In some embodiments, a carrier for the growth factors or other active substances may be incorporated into the delivery system. Thus, for example, as shown in FIG. 24*h*, a carrier 1400 such as a collagen sponge or collagen fibers may be provided. The carrier 1400 may be loaded with growth factors or other active substances. The loaded carrier 1400 then may be placed in the covering.

Figure 24I:
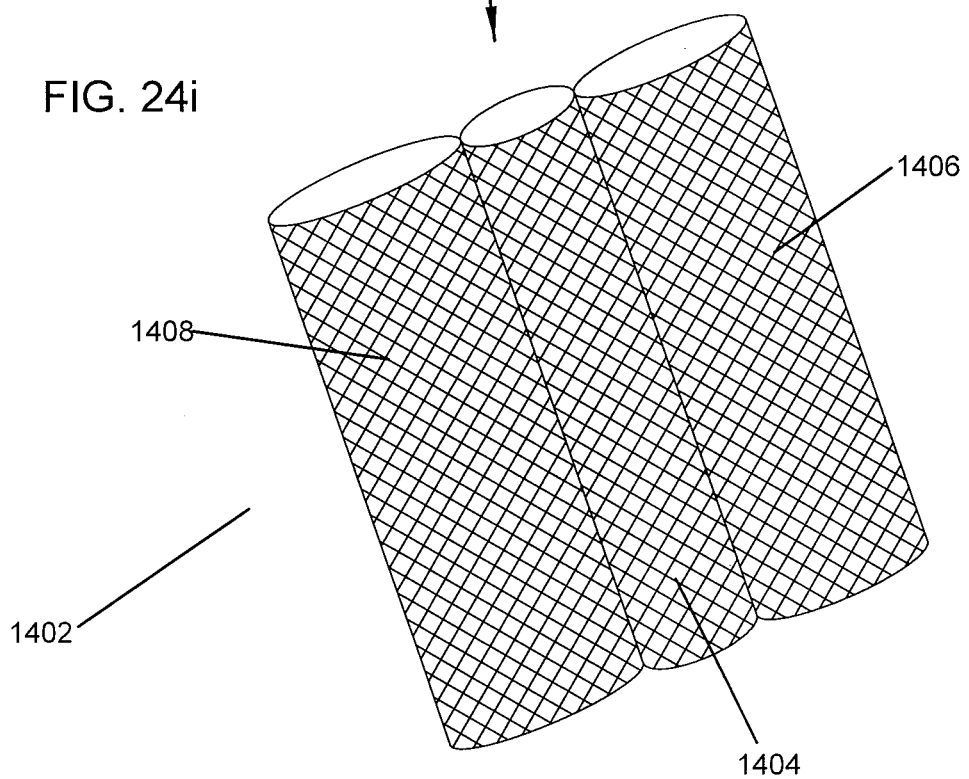
FIG. 24i illustrates a multi-compartment covering that may house a carrier, in accordance with one embodiment.

FIG. 24*i* illustrates an example embodiment of a covering 1402 with such carrier 1400. As shown, a covering 1402 is provided comprising three compartments: a central covering 1404 and first 1406 and second lateral coverings 1408. In one embodiment, the central covering 1404 receives a carrier 1400 such as shown in FIG. 24*h* and the lateral coverings 1406, 1408 include a material such a osteoconductive and/or osteoinductive material such as DBM. Such embodiment may be used for, for example, spinal fusion. In further embodiments, additional coverings may be included. Such additional coverings may be filled with, for example, DBM, a calcium phosphate, a polymer, a combination material, an osteoconductive material, and/or an osteoinductive material. While a multi-compartment covering is shown, it is to be appreciated that a carrier may alternatively be used in a single compartment embodiment.

V. Sterilization

The delivery system, including covering and substances for delivery, may be terminally sterilized. Sterilization may be done using any technique now or later known including, for example, gamma radiation, electron beam radiation, UV, cobalt source radiation; autoclaving, dry heat, and by supercritical fluids.

Further, in various embodiments, a portion of the delivery system, such as the covering of the substance for delivery by the covering may be separately sterilized prior to assembly of the delivery device. Different sterilization methods can be used for different parts of the delivery system. Thus, the sterilization method used may be customized for the materials of the portion of the system being sterilized. For example, a synthetic calcium phosphate filler may be sterilized using radiation while a resorbable polymer covering may be sterilized with EtO. Further, only some portions of the delivery system maybe sterilized.

Generally, in some embodiments, the delivery system (assembled and filled covering; placed in final packaging) may be processed under aseptic conditions from sterile components. Such processing results in a sterile delivery system without a terminal sterilization step.

VI. Kit and Tools

In some embodiments, kits may be provided with a plurality of differently sized or differently shaped coverings. In a further embodiment, a kit may include one or more tools for placing the covering. These may include, for example, a cutter, a caulker or insertion tool, or other tool.

VII. Method of Use

The covering delivers the substance or substances in vivo. Such delivery may be active, passive, by diffusion, or other. Active delivery may include the degradation or decomposition of the covering with the interaction of body fluids, extracellular matrix molecules, enzymes or cells. It may also include the cleavage of physical and/or chemical interactions of substance from covering with the presence of body fluids, extracellular matrix molecules, enzymes or cells. Further, it may comprise formation change of substances (growth factors, proteins, polypeptides) by body fluids, extracellular matrix molecules, enzymes or cells.

The covering is loaded with the substance for placement in vivo. The covering may be pre-loaded, thus loaded at manufacture, or may be loaded in the operating room or at the surgical site. Preloading may be done with any of the substances previously discussed including, for example, DBM, synthetic calcium phosphates, synthetic calcium sulfates, enhanced DBM, collagen, carrier for stem cells, and expanded cells (stem cells or transgenic cells). Loading in the operating room or at the surgical site may be done with any of these materials and further with autograft and/or bone marrow aspirate.

Figure 25:
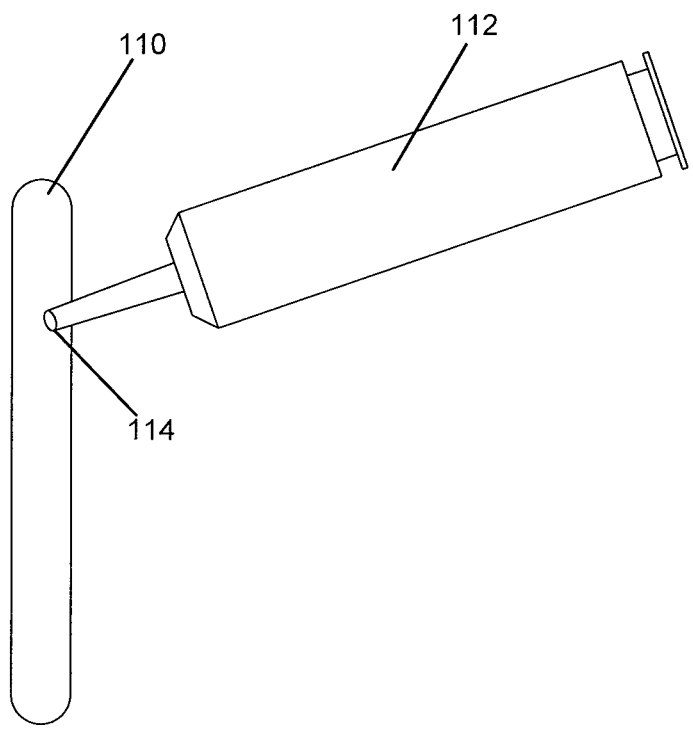
FIG. 25 illustrates a covering being loaded with a substance using a syringe, in accordance with one embodiment.

Any suitable method may be used for loading a substance in the covering in the operating room or at the surgical site. For example, the substance may be spooned into the covering, the substance may be placed in the covering using forceps, the substance may be loaded into the covering using a syringe (with or without a needle), or the substance may be inserted into the covering in any other suitable manner. FIG. 25 illustrates loading the covering 110 with a syringe 112. As shown, in some embodiments, the covering 110 may include a port 114 or other structure for receiving the syringe 112 or similar instrument. Specific embodiments for loading at the surgical site include for vertebroplasty or for interbody space filler.

For placement, the substance or substances may be provided in the covering and the covering placed in vivo. The covering may be delivered using any of the insertion tools provided herein or may be otherwise delivered. In one embodiment, the covering is placed in vivo by placing the covering in a catheter or tubular inserter and delivering the covering with the catheter or tubular inserter. The covering, with a substance provided therein, may be steerable such that it can be used with flexible introducer instruments for, for example, minimally invasive spinal procedures. For example, the osteoimplant may be introduced down a tubular retractor or scope, during XLIF, TLIF, or other procedures. In other embodiments, the covering (with or without substance loaded) may be placed in a cage, for example for interbody fusion. In some embodiments, the covering may be wet prior to placement. Wetting of the covering may enhance manipulability and/or flexibility of the covering. Wetting may be done using, for example, water, blood, marrow, saline, or other fluid. The covering may be delivered using any of the insertion tools provided herein or may be otherwise delivered.

Figure 20:
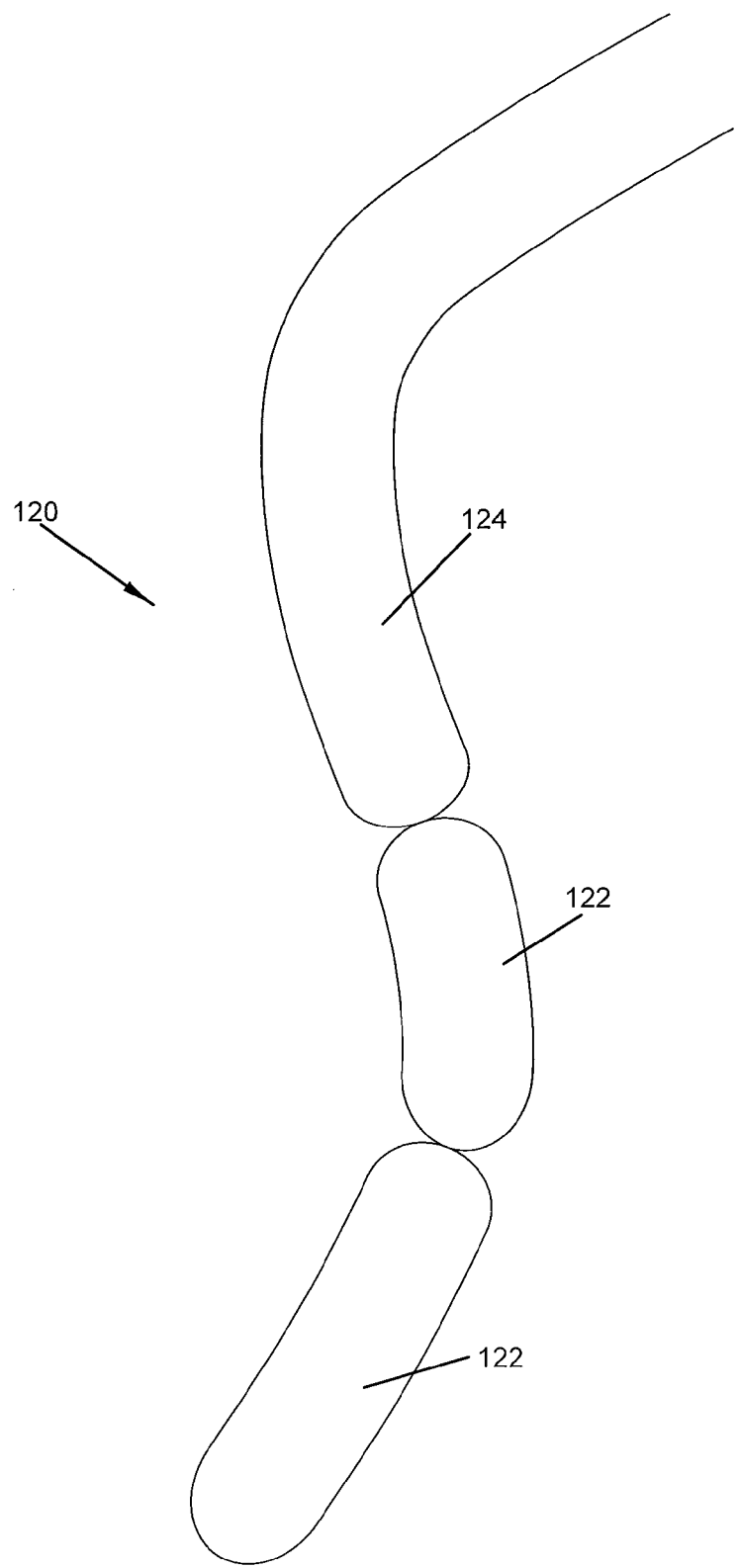
FIG. 20 illustrates a tubular covering partially divided into compartments, in accordance with one embodiment.

In continuous tube embodiments, the surgeon may divide the tube into the desired number of compartments, using a crimper, heat tool, or other. FIG. 20, previously discussed, illustrates an embodiment of a tubular covering 120 partially divided into compartments 122. As shown, the tubular covering 120 includes a further portion 124 that may be divided into compartments. After subdivision into compartments 122, one or more compartments 122 may be removed from the tube 120 for implantation. Alternatively, in an embodiment wherein the tube is perforated into a plurality of compartments, the surgeon may select the number of compartments desired and cut along the applicable perforation. In some embodiments, some of the compartments may be prefilled with a substance for delivery and other compartments may be empty for filling by the surgeon. For example, ever other compartment between perforations may be preloaded or filled. The osteoimplant thus may be customized by filling the empty compartments with a desired substance.

For example, in some embodiments, a portion of the covering for example, one compartment of a multi-compartment covering, may be filled with autograft. Thus, the covering may be substantially empty prior to surgery. During surgery, a surgeon may remove autograft from the patient and place the autograft in the substantially empty compartment. Such placement may be done in any suitable manner. In one embodiment, the covering may be provided with a port for receiving an opening of an injection device and the autograft may be injected into the covering. Alternatively, the autograft may be mixed with allograft, synthetics, or any other desired substances or combination of substances.

Attachment mechanisms provided on the covering may be used to couple the covering to a site in vivo.

VIII. Applications

Coverings and delivery systems as provided herein may be used in any suitable application. In some embodiments, the covering and associated delivery system may be used in spinal interbody fusion, posterolateral fusion, healing of vertebral compression fractures, minimally invasive procedures, correction of adult or pediatric scoliosis, treatment of long bone defects, treatment of osteochondral defects, ridge augmentation (dental/craniomaxillofacial, e.g. edentulous patients), beneath trauma plates, treatment of tibial plateau defects, filling of bone cysts, wound healing, around trauma, contouring (cosmetic/plastic/reconstructive surgery), and others. Generally, delivery systems such as provided herein may be used in bone or hard tissue applications as well as soft tissue applications including plastic and reconstructive surgery. The delivery system may be used in a minimally invasive procedure via placement through a small incision, via delivery through a tube, or other. The size and shape of the covering and associated delivery system may be designed with restrictions on delivery conditions.

Spinal Fusion

One application for using a delivery system as disclosed is fusion of the spine. Spinal fusion is a surgical procedure used to combine two or more vertebrae. It involves adding bone graft or bone graft substitute to an area of the spine to set up a biological response, which causes the bone to grow between the two vertebral elements and thereby stop motion at that segment. Spinal fusion may be used to eliminate pain caused by motion of the vertebrae, or compression of the disc space, by immobilizing the vertebrae themselves.

Spinal fusion may generally be done in, for example, the lumbar, cervical, or thoracic areas of the spine. Patients with the following conditions, for example, may require spinal fusion: degenerative disc disease, spinal disc herniation, discogenic pain, spinal tumor, vertebral fracture, scoliosis, kyphosis, spondylolisthesis, spondylosis, posterior rami syndrome, other degenerative spinal conditions, or any other condition that causes instability of the spine.

Generally there are two main types of lumbar spinal fusion that may be used together or separately: posterolateral fusion and interbody fusion. Posterolateral fusion inserts the bone graft between the transverse processes in the back of the spine. Generally, the vertebrae may then be fixed in place with screws and/or wire through the pedicles of each vertebra, for example, that attach to a fixation device on each side of the vertebrae. In some embodiments, a covering such as provided herein may form such fixation device or may attach to such fixation device. Interbody fusion comprises inserting the bone graft in the intervertebral space. Prior to spinal fusion, the disc is removed to open the disc space for such bone graft. A delivery system as provided herein may be placed between the vertebra to maintain spine alignment and disc height and to help the fusion process. The fusion occurs between the endplates of the vertebrae. If both types of fusion are used together, it is known as a 360-degree fusion.

In clinical use, a delivery system comprising a covering and delivered substance may be used in any type of spinal fusion procedure including, for example, posterolateral fusion, interbody fusion (of any type), facet fusion, spinous process fusion, anterior only fusion, or other fusion procedure. The covering and delivered substance may be used, for example, to bridge the gap between the transverse processes of adjacent vertebral bodies. The delivery system may also be used to bridge two or more spinal motion segments. Generally, the delivery system may be used in other fusion procedures. For all fusion procedures, the covering may surround the substance to be implanted, and contain the substance to provide a focus for healing activity in the body. The covering generally retains the substance in appropriate position and substantially prevents migration of the substance from the fusion site (referred to as graft migration).

All spinal fusion techniques described below may be conducted using fixed protective tubes to protect surrounding neurological and vascular structures, known as minimally invasive procedures, or through an unprotected open procedure. The discussed techniques and procedures may be done using mini-open, endoscopic, or minimally invasive techniques using different parameters including, for example, incision size, location, and instruments. Variation of such parameters is within the skill of someone skilled in the art. Discussion of any non-minimally invasive techniques for such procedures thus is not intended to be limiting.

Posterior Lumbar Interbody Fusion (PLIF)

In one application, the covering and delivery system may be used in posterior lumbar interbody fusion (PLIF). According to this technique, the vertebrae are reached through an incision in the patient's middle back, which allows direct access to the area being treated. In this procedure, prior to surgery visualization may be performed to determine the size of the area to be treated. A 3-6 inch incision is made in the back of the patient and the spinal muscles are retracted, or separated, in order to access the vertebral disc. A laminectomy is performed to provide visual and physical access to the nerve roots. In some cases, the facet joints that lie directly over the nerve roots may be trimmed to create more room for the nerve roots. The affected disc and surrounding tissue is removed. The bone surfaces of the adjacent vertebrae are prepared for fusion. After preparation of the disc space, the delivery system may be implanted.

The delivery system of the present invention in one embodiment may include a covering with a cartridge covering for placement in an interbody fusion cage for a PLIF procedure. The interbody fusion cage may be any suitable cage, such as one suitable for PLIF, may have any suitable dimensions, and may be made of any suitable material. The containment area(s) of the cage may be filled with a covering and substance as provided herein and may also be filled with bone graft, allograft, BMP or other suitable material to promote fusion between the vertebrae. Additional instrumentation may be used, such as rods, screws, wires or the like to further stabilize the spine. For a standard PLIF procedure, the bone graft and/or instrumentation is performed on both sides.

Transforaminal Lumbar Interbody Fusion (TLIF)

In another application, the covering and delivery system may be used with transforaminal lumbar interbody fusion (TLIF), which is a refinement of PLIF. TLIF fuses the anterior and posterior columns of the spine through a single posterior approach. The anterior portion of the spine may be stabilized by a bone graft and an interbody spacer, whereas the posterior column may be locked in place with a cage and/or pedicle screws, and/or rods, and bone graft. Only one side of the back is accessed and affected in TLIF. Accordingly, TLIF involves approaching the spine through a midline incision in the back of the patient using a transforaminal approach that is both posterior and lateral.

Using this approach may reduce the amount of surgical muscle dissection needed and may also minimize the nerve manipulation required to access the vertebrae, discs and nerves. As with PLIF, disc material is removed from the spine and may be replaced with the delivery system of the present disclosure.

A portal opening for a TLIF procedure generally ranges from approximately 10 mm to approximately 20 mm, with 16 mm being an acceptable average.

To place the covering, the covering may be provided in a tubular insertion tool. Such insertion tool may have a diameter approximately matching a diameter of the covering. The insertion tool may be placed into a minimally invasive portal for accessing the disc space. A plunger mechanism may be used to expel the covering from the insertion tool. In some embodiments, a single covering may be placed using the insertion tool. In other embodiments, a plurality of coverings, for example, generally smaller coverings, may be placed in a single procedure using the insertion tool.

In another embodiment, as shown in FIGS. 32a-32e, the site to be treated comprises two vertebral bodies 620 and an intervening disc 622, and an annulus covering. A partial or complete discectomy is performed to prepare the site 628, and the lip of the vertebra 624 is removed. The covering containing graft material 626 is placed into the site 628 against the opposing surface 630. The opposing surface 630 may be remaining disc material, annulus, or other graft. The covering 626 may be packed with graft material at a relatively low density to facilitate manipulation and shape changing without significant deformation of the covering. The graft-containing covering (or delivery system) 626 may be placed manually or with an instrument, such as a bone tamp, or other suitable instrument, and adjusted until it conforms to the surgical site.

As discussed previously, the interbody fusion cage may be any suitable cage, such as one suitable for TLIF, may have any suitable dimensions, and may be made of any suitable material.

Figure 26A:
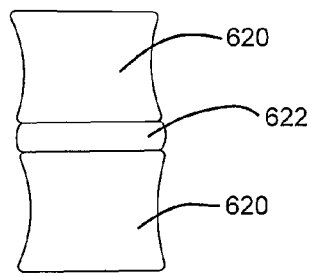
FIG. 26a illustrates two vertebra bodies and a disc to be prepared for discectomy, in accordance with one embodiment.
Figure 26B:
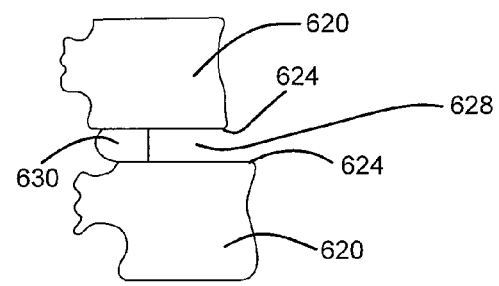
FIG. 26b illustrates preparation of the site whereby the lip of the vertebra are removed, in accordance with one embodiment.
Figure 26C:
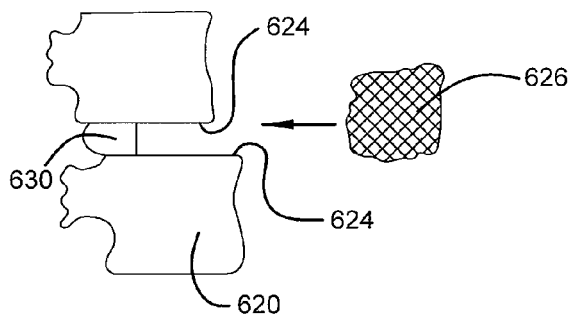
FIG. 26c illustrates where a covering containing graft will be placed in the site, in accordance with one embodiment.
Figure 26D:
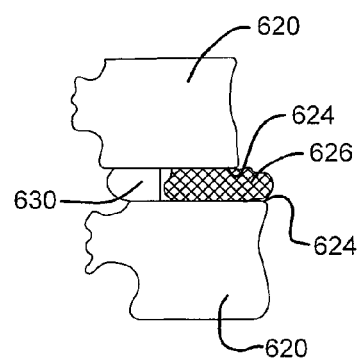
FIG. 26d illustrates insertion of the covering containing graft in the site, in accordance with one embodiment.
Figure 26E:
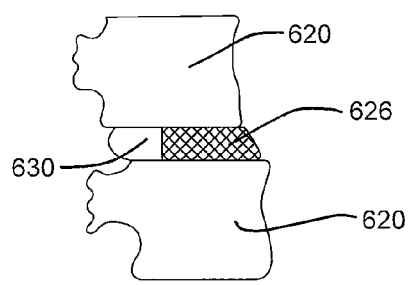
FIG. 26e illustrates the complete placement of the covering containing graft in the site, in accordance with one embodiment.
Figure 26F:
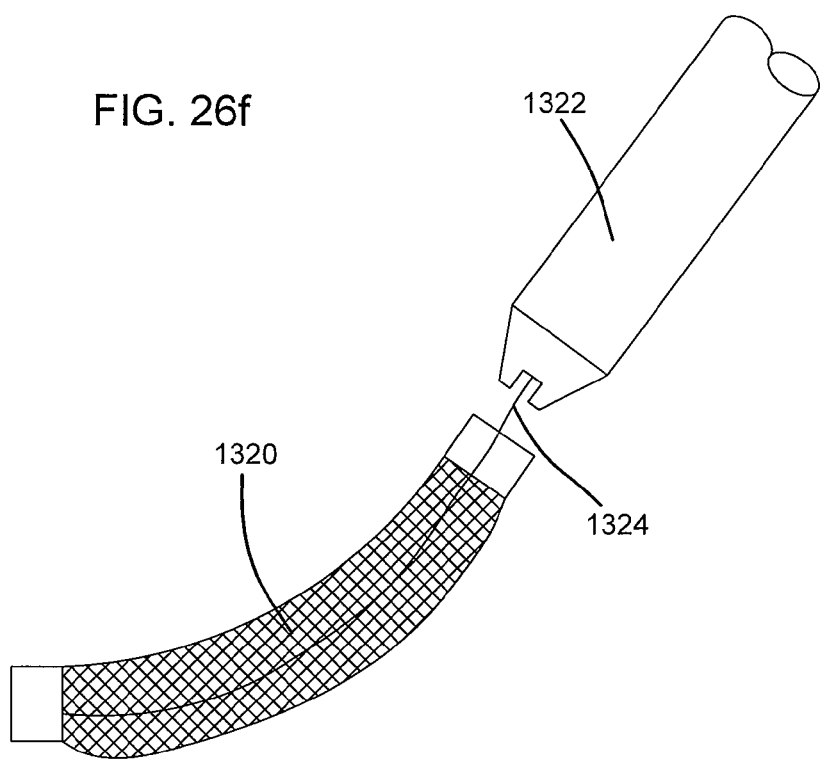
FIG. 26f illustrates a curved covering in an insertion tool or device, in accordance with one embodiment.
Figure 26G:
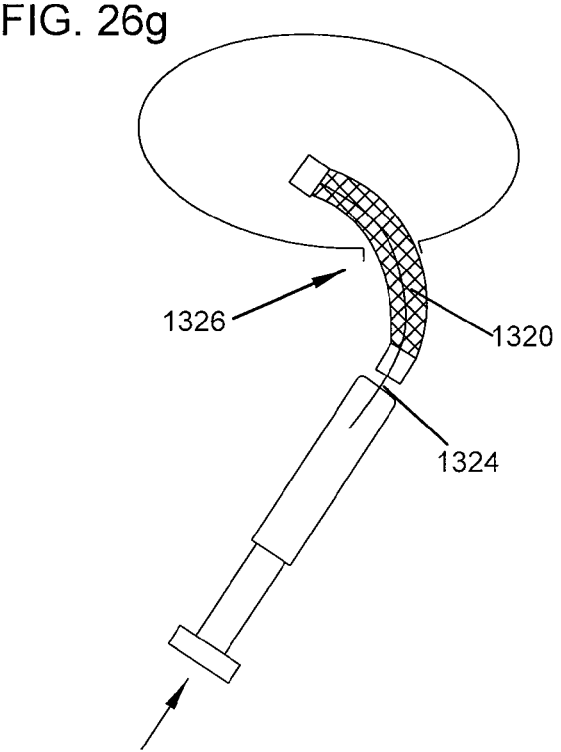
FIG. 26g illustrates a curved covering inserted through a TLIF entrance with the reinforcing extending proximally therefrom, in accordance with one embodiment.

FIGS. 26f and 26g illustrate a curved covering 1320 used in a TLIF procedure. FIG. 26f illustrates a curved covering 1320 in an insertion tool or device 1322. As shown, in a TLIF procedure, a shaping or reinforcing structure 1324 of the curved covering 1320 may extend out of and interface with an insertion tool or device 1322. FIG. 26g illustrates a curved covering 1320 inserted through a TLIF entrance 1326 with the reinforcing 1324 extending proximally therefrom. The shaping or reinforcing structure 1324 facilitates positioning of the covering 1320 maintaining the covering 1320 in a curved configuration. After placement of the covering 1320, the shaping or reinforcing structure 1324 may be removed with the covering 1320 or left in place.

Anterior Lumbar Fusion (ALIF)

In another application, the covering and delivery system may be used with an anterior lumbar fusion (ALIF) procedure. Whereas PLIF and TLIF access the spine via the patient's back, ALIF approaches the spine from the front of the patient's body. Generally, a 3-5 inch incision is made in the lower abdomen, or the side of the patient. In some cases it may be necessary to cut through the muscles of the lower abdomen, which would require later repair. The abdominal muscles and blood vessels may be retracted in order to access the vertebrae. The disc and disc material may then be removed. As with PLIF and TLIF, an embodiment of the present disclosure may be inserted in the space where the disc and disc material were.

Figure 26H:
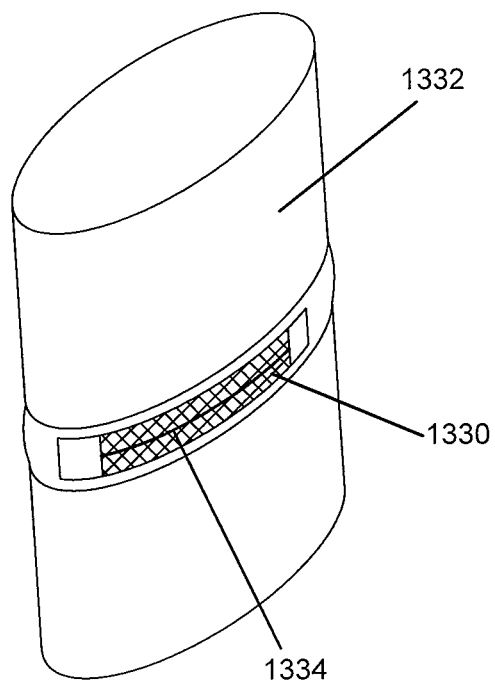
FIG. 26h illustrates a curved covering inserted via an ALIF procedure, in accordance with one embodiment.
Figure 26I:
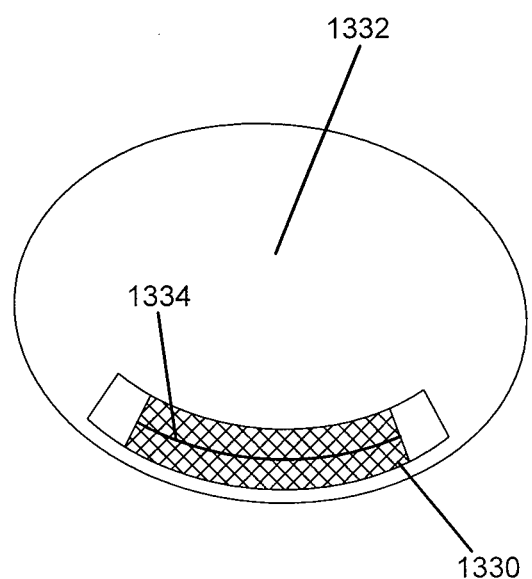
FIG. 26i illustrates a top view of a curved covering inserted via an ALIF procedure, in accordance with one embodiment.

In one embodiment, a curved covering may be used for an ALIF procedure. FIGS. 26h and 26i illustrate a curved covering 1330 inserted via an ALIF procedure. As shown, the curved covering 1330 has the form of a curve and thus complements the curve of the anterior endplate 1332. The curved covering 1330 may be in a curved configuration by provision of a shaping or reinforcing structure 1334.

Antero-Lateral IBF Approach (XLIF Approach)

In another embodiment, the covering and delivery device may be used in an extreme lateral interbody fusion (XLIF). XLIF involves a minimally invasive approach to the anterior spine that avoids an incision that traverses the abdomen and also avoids cutting or disrupting the muscles of the back. In XLIF, the disc space is accessed from a very small incision, for example approximately 1-3 inches, on the side or flank of the patient. Another small incision, for example approximately 1 inch long, may be made just behind the first incision. Retractors and a fluoroscopy machine may be used to provide real-time visualization of the spine. Special monitoring equipment may also be used to determine the proximity of the working instruments to the nerves of the spine. The disc material is removed from the spine. An embodiment of the present disclosure may be inserted in the space where the disc and disc material were.

AxiaLIF

In yet other embodiments, the delivery system may be used in AXIALIF, using a Trans 1 system. Such procedure is described, for example, at http://www.trans1.com/axiaLif_axiaLif_technology.html and enters near the top of the coccyx for an L5-S1 fusion. The technique involves accessing the lumbar spine through a percutaneous opening adjacent to the sacral bone, alleviating the need for the surgeon to cut through soft tissues like muscles and ligaments.

Minimally Invasive Posterolateral Fusion

In a further embodiment, the delivery system may be used with a posterolateral fusion operation. In contrast to PLIF, a posterolateral fusion operation keeps the disc space intact and the bone graft or cage is placed between the transverse processes in the back of the spine. In the posterolateral fusion operation the bone may heal and stabilize the spine from the transverse process of one vertebra to the transverse process of the next vertebra. A smaller incision may be used to make the posterolateral fusion minimally invasive. After the small incision, for example approximately 3 cm, is made in the patient's lower back, the muscles surrounding the spine may be dilated in order to permit access to the section of the spine to be stabilized. The lamina is facilitate visualization of the nerve roots to be seen. The facet joints may be trimmed to give the nerve roots more room. A covering and associated delivery system as provided herein may be laid between the transverse processes in the back of the spine.

In one embodiment the tension band and covering illustrated in FIG. 14a or 14b may be used for posterior lateral fusion procedures.

A further embodiment may comprise a covering that may be fixed in place using a facet screw to bridge a facet joint for fusion.

Posterior Cervical Approach

In another embodiment, a covering and associated delivery system may be used with a posterior cervical fusion procedure. This procedure approaches the spine through the back of a patient's neck. The procedure involves joining two or more neck vertebrae into one solid section of bone. The procedure is generally performed to remedy neck fractures and dislocations and to remedy deformities in the curve of the neck. The patient lies face down during the procedure. An incision may be made down the middle of the back of the neck. Retractors are used to separate and hold the neck muscles and soft tissues apart to provide a space for the surgeon to work. A layer of bone may be shaved from the surface of the lamina of each vertebra that will be fused in order to stimulate healing. A covering as provided herein may be laid over the back of the spinal column.

Posterior Lumbar Fusion

In another embodiment, the covering and associated delivery system may be used with a posterior lumbar fusion procedure. Posterior lumbar fusion is a general term referring to a surgical procedure where two or more lumbar spine bones are fused together along the sides of the bone. Bone graft is placed along the side of the spine bones, as opposed to between the disc spaces as with interbody fusion. This procedure is performed through an incision in the lower middle of the back, which reaches to the spinous processes (the bony projections off the back of the vertebrae). The incision may be, for example, approximately 4-8 cm. The tissues and small muscles along the side of the low back are separated and lifted off of the vertebrae in order to expose the target area. A laminectomy may be performed. Prior to fusion, a layer of bone from the back surfaces of the spinal column may be shaved. A covering and associated delivery system may be placed over the back of the spinal column. Additional instrumentation, such as plates, rods, screws, or other, may also be used to fix the bones in place and prevent the vertebrae from moving. Coverings such as provided herein may be used in traditional posterior lumbar fusion procedures or in minimally invasive posterior lumbar fusion procedures.

In various embodiments, coverings for use in posterior lumbar fusion may be generally tubular and may have dimensions of approximately 2.5 cm wide and approximately 5 cm to approximately 10 cm in length. Generally, wider coverings may be used in the lumbar region and narrower coverings may be used in the thoracic region. A covering with graft material contained therein substantially retains the graft material in the disc space. In some embodiments, the covering may be fixed in place, such as by suturing the covering to or through the transverse process.

Cervical Interbody Fusion

In another application the covering and delivery system may be used with an anterior or posterior cervical interbody fusion procedure. An incision may be made in either the anterior or the posterior of the patient. The procedure is similar to the posterior cervical fusion, except that in the cervical interbody fusion an entire disc may be removed and a covering and associated delivery system may be placed in the disc space. The covering may be provided as a cartridge for placement in an interbody fusion cage. As discussed previously, the interbody fusion cage may be any suitable cage, such as one suitable for cervical interbody fusion, may have any suitable dimensions, and may be made of any suitable material. Coverings may be useful, for example, for fusion of 2 or more levels. Radiopaque markers may be provided to facilitate imaging and to confirm final seating location. In some embodiments, a covering such as provided herein may be used in a Harms cage for corpectomy procedures. Additional instrumentation may be used, such as rods, screws, wires or the like to further stabilize the spine.

Occipital Cervical Fusion

In another embodiment, the covering and associated delivery system may be used with an occipital cervical fusion procedure. Occipital cervical fusion involves fusion of the occiput to the cervical spine with possible instrumental fixation. Following placement of Mayfield tongs on the skull, a patient may be turned prone onto bolsters. The head and neck may be immobilized, in a Mayfield extension frame, for example. Visualization may be performed to confirm reduction of the occipital-cervical junction. Following prepping and draping of the posterior occipital-cervical region, as well as the iliac crest, a midline incision may be performed and exposure of the occiput, inion, arch of C1 and posterior elements of C2 and C3, for example may be performed. The covering may comprise a cartridge for placement in a cervical fusion cage. Such a cage may have any suitable dimensions and may be made of any suitable material. The containment area(s) of the cage may be filled with the covering/delivery system and may further be filled with bone graft, allograft, BMP or any other suitable material to promote fusion between the vertebrae. Additional instrumentation may be used, such as rods, screws, wires, or the like, to further stabilize the spine.

Small Joint Fusion

In other applications, the delivery system may be used in small joint fusion. For example, the delivery system may be placed between wrist or ankle bones, metatarsals, phalanges, metacarpals, or other to create fusion. For example, in one embodiment, a hole may be drilled that encompasses a portion of each articular surface and the covering may be placed into the hole, thus spanning the spacing between the articular surfaces. In another embodiment, endplates of the bones may be rasped or otherwise prepared and a covering placed therebetween.

Revision of a Failed Temperomandibular Joint (TMJ)

Figure 27A:
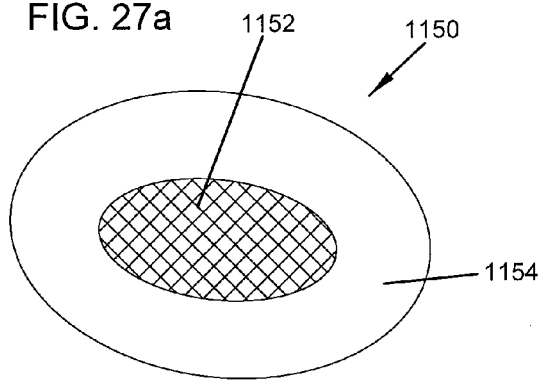
FIG. 27a illustrates a top view of a covering with a generally spherical central containment portion, in accordance with one embodiment.
Figure 27B:
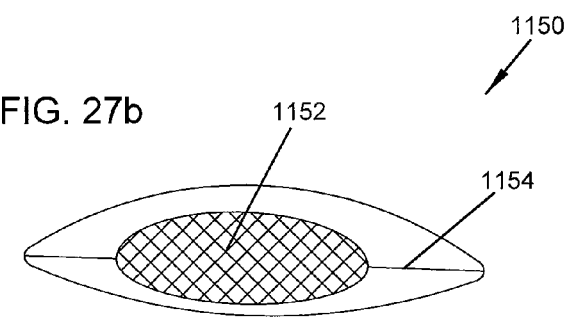
FIG. 27b illustrates a perspective view of a covering with a generally spherical central containment portion, in accordance with one embodiment.

FIGS. 27a-27d illustrate an embodiment wherein the covering is configured as a defect bridge and restrictor. The covering may be used to treat eroded fossa from disease, trauma, or failed implant. In one embodiment, the covering may be used to treat a failed temperomandibular joint (TMJ). FIG. 27a illustrates a top view and FIG. 27b illustrates a perspective view of the covering 1150. As shown, the covering 1150 includes a generally spherical central containment portion 1152. A flange portion 1154 extends from the containment portion 1152. The containment portion 1152 may be configured to receive a substance for retention or delivery at a surgical site such as to bridge a defect. The flange portion 1154 may be used to fix the covering at the surgical site.

Figure 27C:
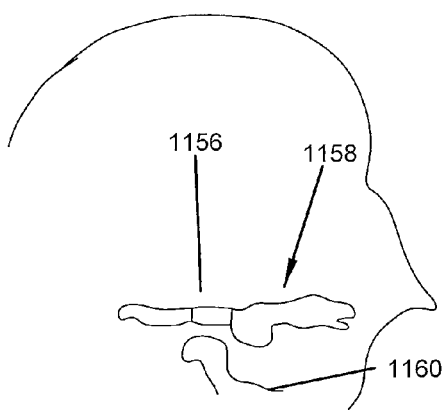
FIG. 27c illustrates the implant site where the covering of D1 and D2 will be used, in accordance with one embodiment.
Figure 27D:
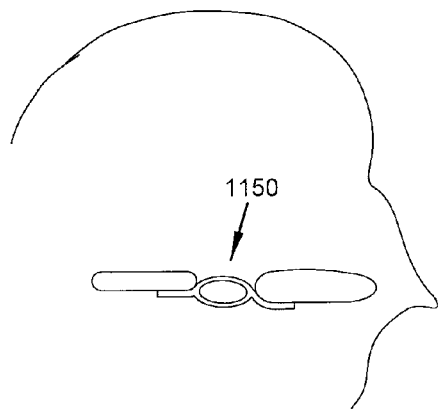
FIG. 27d illustrates a covering of D1 and D2 placed in, covering, and bridging the defect, in accordance with one embodiment.

FIG. 27c illustrates the implant site. As shown, eroded fossa 1156 presents in temporal bone 1158 near the mandible 1160. FIG. 27d illustrates a covering 1150 placed in the defect. As shown, the covering 150 bridges and fills the defect. The covering 1150 may be fixed at the surgical site using an attachment mechanism. For example, the covering may be tacked or micro-screwed. Soft tissue flaps may be used to cover the covering. After healing, the site may be prepared for an implant.

Repairing the Floor of the Orbit

In a further embodiment, a covering and associated delivery system may be used to repair the floor of the orbit. Orbit and orbital floor fractures are common midface fractures. When only the orbital floor is fractured, this is known as a blowout fracture. When orbital floor fractures are also associated with orbital rim and lateral buttress fractures, they are known as tripod fractures. The orbital floor is concave inferolaterally and is typically more convex medially and becomes substantially convex posteriorly behind the equator of the globe. When repairing the floor of the orbit, it may also be necessary to repair the orbital walls and recreate the orbital volume, in order to allow repositioning of the globe into its normal anatomical position.

Several surgical approaches exist to gain access to the orbital floor, for example, transconjunctival, subciliary, and subtarsal being among the most common. It will be recognized by those skilled in the art, however, that any suitable approach may be used to gain access to the orbital floor. Regardless of the approach used, the repair procedures are substantially the same. The area is dissected. The globe or optic nerve must not be retracted too forcefully or blindness may result. The contents of the floor are removed from the maxillary sinus. A covering may be placed in the defect to keep the maxillary sinus contents from regressing. In some embodiments; the covering may have a plate-like configuration.

Cranioplasty or Burr Hole Defects

In further embodiments, a covering and associated delivery system may be used for cranioplasty or to treat burr hole defects. Cranioplasty is reconstructive surgery to repair large defects in the frontal and neurocranial areas of the skull caused by, for instance, trauma or intercranial surgery. The main purpose in performing cranioplasty is to protect the brain because when the protective bones of the cranium are missing, the brain is only covered by skin, scar tissue and the meninges. Reconstruction will also attempt to create harmonic contours with an aesthetic appearance. The covering generally fits against all the borders of the bone defect and also resembles the aesthetic, harmonic, and symmetric contour of a normal skull. Generally, a cranioplasty procedure may involve exposing the bony margins of a patient's defects by separating the covering skin from the meninges. The covering may then be placed and fixed with appropriate attachment mechanisms, such as with titanium microscrews.

Similarly, burr hole defects resulting, for example, from cranial trepanation, can be very noticeable when they occur in areas that are not covered by hair. A covering as provided herein may be placed in the burr hole defect. In one embodiment of the present invention the covering and delivery system may be used to either "tent-over" the defect, or be directly placed into the defect with the edges reaching into the margins.

Osteonecrosis

In yet a further embodiment, a covering and associated delivery system may be used to treat osteonecrosis. Osteonecrosis, also known as avascular necrosis, aseptic necrosis and ischemic necrosis, is a disease resulting from the temporary or permanent loss of blood supply to the bones. The bone tissue dies and causes the bone to collapse without blood. If this process occurs near a joint, it may lead to collapse of the joint surface. Though most commonly this disease affects the ends of the femur, it may affect any bone, including but not limited to the tibia, upper extremity, foot, ankle, knee, shoulder, and jaw. The disease may affect only one bone, more than one bone at the same time, or more than one bone at different times.

Several treatments are available depending on the stage and location of the disease. Core decompression involves surgically removing the inner cylinder of bone to reduce the pressure within the bone allowing more blood to flow there. A covering and associated delivery system may be implanted into the cored space to stimulate new vascular growth. Osteotomy involves reshaping the bone to reduce the amount of stress on the affected area. The substance within the covering may be a bone graft and, in some embodiments, a vascular graft. In other embodiments, a vascular graft may be added around the delivery system. Such vascular graft may increase the blood supply to the affected area. Finally, arthroplasty, or total joint replacement may be used. This procedure involves replacing the diseased joint with artificial parts.

Iliac Crest Defects

In another embodiment, a covering and associated delivery system may be used to treat an iliac crest defect. Iliac crest defects may result from trauma or from surgery, particularly donor site surgery. Reconstructing the iliac crest may be associated with significantly lower intensity and incidence of pain than in those with unreconstructed iliac crest defects. Additionally, reconstructing the iliac crest defect may be substantially superior cosmetically. A covering thus may be configured to conform to the space of the iliac crest defect.

Segmental Bone Defects

In a further embodiment, the covering may be used in a variation of the Masquelet technique. The Masquelet technique is used in long bone trauma applications where there is a large intercalary defect, such as where a segment of a long bone is missing. The Masquelet technique typically comprises two stages, a first stage wherein a spacer is placed and soft tissue forms around the spacer, and a second stage wherein the spacer is removed and a bone graft is placed in the space left by the spacer. The formed soft tissue (a kind of periosteum) forms vascularized fibrous sheath. This sheath acts as a prepared environment for bone graft and is used to cover the bone graft. The spacer may be, for example, PMMA cement with an antibiotic. The spacer thus helps clear the infection and causes inflammation at the site, which in turn leads to formation of the soft tissue. After removal of the spacer, the soft tissue (or periosteum like layer) facilitates new bone growth around the to-be-placed graft material.

In some embodiments, a covering such as provided herein may be similarly used for trauma repair in a long bone segmental defect. For example, a covering may be provided with a substance (such as a graft material) provided therein suitable for trauma repair. The covering may be formed as a temporary covering where, for example, the covering is designed to be resorbed in a relatively short time frame. The covering thus is used to hold the space (excluding soft tissue) in the long bone and have soft tissue form therearound. The covering may be resorbable and may have materials such as antibiotics provided therein (in the material of the covering or in the substance within the covering). Like the spacer of the Masquelet technique, the covering can assist in reducing infection and may also stimulate inflammation to cause formation of a periosteum-like layer. The covering acts as a temporary covering and is resorbed by the body. After resorption of the covering, the graft material is exposed and facilitates new bone growth. Unlike the Masquelet technique, which requires a second surgery step to remove the spacer and place the graft material, the entire process is stimulated with a single surgical step.

Figure 38A:
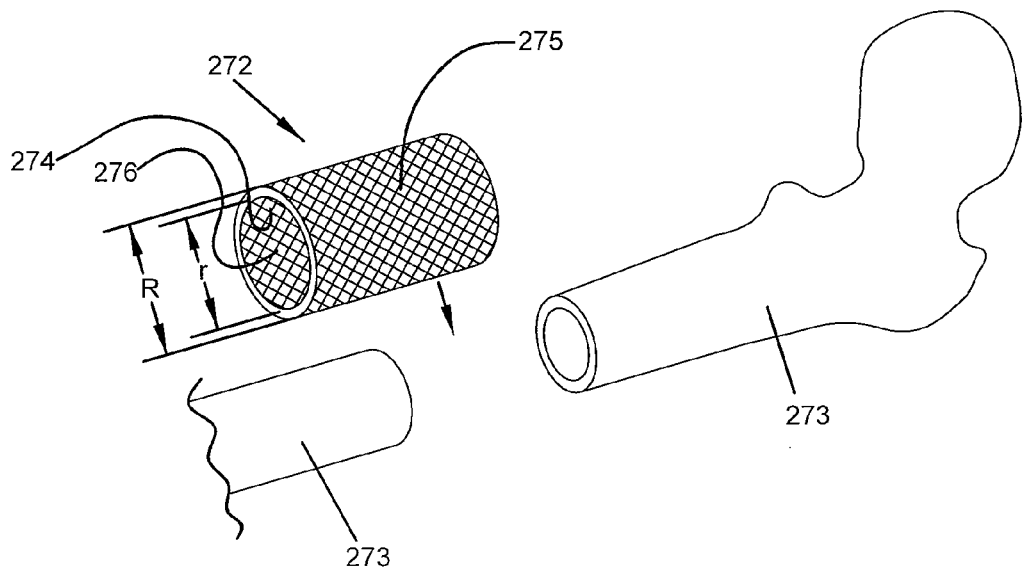
FIG. 38a illustrates a tubular covering having a hollow central core for use in repairing a segmental defect.
Figure 38B:
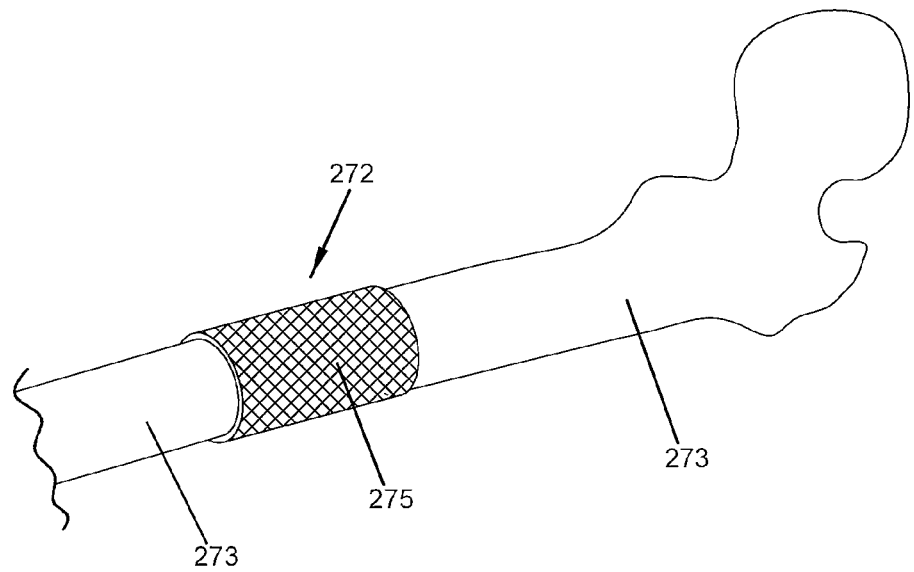
FIG. 38b illustrates a tubular covering having a hollow central core used in segmental reconstruction.

In alternative embodiments, as depicted in FIG. 38, a covering material may be provided as a cylinder 272 defining a hollow core 276 or tube. The cylinder may have an outer covering material 275 defining an outer radius R of the cylinder 272. The hollow core may be defined by an inner covering material 274 further defining an inner radius r of the cylinder. The cylinder shaped covering material may be used to deliver graft materials for segmental reconstruction of a bone 272, in revision implants for the proximal femur, or for other sites.

Acetabular Defect

Pelvic discontinuity may be encountered during acetabular revision in patients with severe acetabular bone loss or defects. Recognition of the discontinuity and appropriate intraoperative treatment contribute to a successful clinical outcome. The treatment for the discontinuity depends on how much host bone remains, the potential for healing of the discontinuity, and the potential for biologic ingrowth of acetabular components. If healing potential of the discontinuity exists, the discontinuity may be treated in compression with a posterior column plate and structural allograft or with an internal plate. If healing potential for the discontinuity does not exist, the discontinuity may be bridged and treated in distraction with an acetabular transplant supported with a cage. In various embodiments, a covering such as provided herein may be configured as a structural implant for healing the discontinuity. In other embodiments, a covering such as provided herein may be configured to bridge the defect. Large acetabular defects can be reconstructed with various methods depending on size and location of the defect.

Figure 27E:
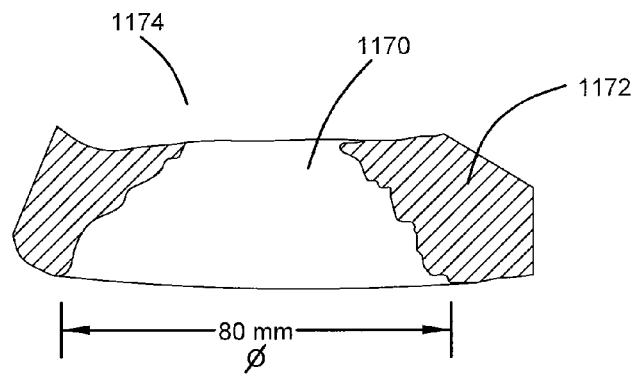
FIG. 27e illustrates the defect where a covering will be placed, in accordance with one embodiment.
Figure 27F:
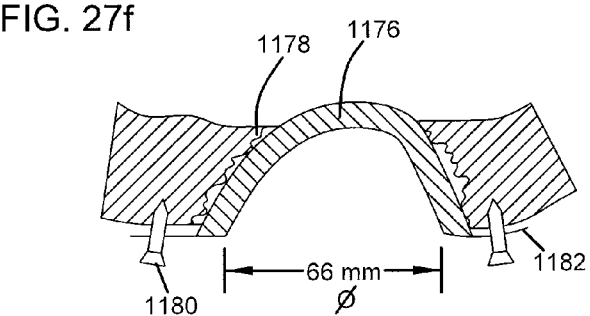
FIG. 27f illustrates a cup shaped covering placed in the defect with the flange resting on the acetabular/pelvic rim, in accordance with one embodiment.
Figure 27G:
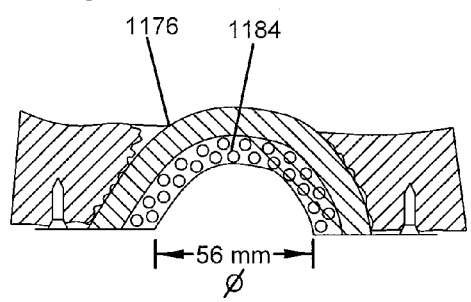
FIG. 27g illustrates a covering that may have cancellous chips or other graft material placed on it and formed to a generally spherical diameter for receipt of an implant, in accordance with one embodiment.
Figure 27H:
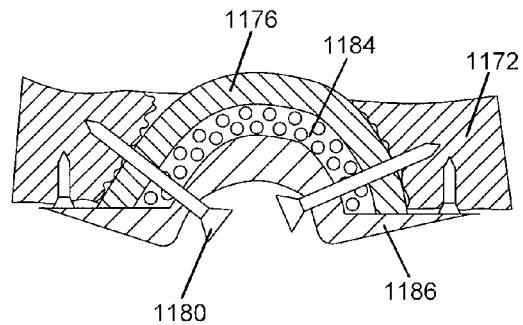
FIG. 27h illustrates an acetabular implant shell placed over the graft material, in accordance with one embodiment.

A cup-shaped acetabular covering may be used to treat, for example, a pelvic-acetabular defect. FIGS. 27e-27h illustrate an embodiment for treatment of a large acetabular defect through the medial wall. FIG. 27e illustrates the defect. Remnant acetabulum 1170 is shown in the pelvic bone 1172 and terminating at the medial wall 1174. An example width of such remnant acetabulum 1170 is approximately 80 mm. FIG. 27f illustrates a cup shaped covering 1176 placed in the defect with the flange resting on the acetabular/pelvic rim 1178. Once positioned, the covering is secured at the site. In the embodiment shown, the covering 1176 is secured using screw attachment mechanisms 1180. The screws 1180 may be threaded through the flange 1182 of covering 1176. The width of the open acetabular region 1170 may then reduced to approximately 66 mm. In some embodiments, a graft material may be placed over the covering. For example, as shown in FIG. 27g, cancellous chips or other graft material 1184 may be placed on the covering 1176 and formed to a generally spherical diameter for receipt of an implant. FIG. 27h thus illustrates an acetabular implant shell 1186 placed over the graft material 1184. In alternative embodiments, the acetabular implant shell 1186 may be placed directly over the covering 1176. The acetabular implant shell 1186 may be fixed using attachment means such as screws 1180. The screws 1180 may extend through the implant shell 1186, the graft material 1184, and the covering 1176.

Figure 27I:
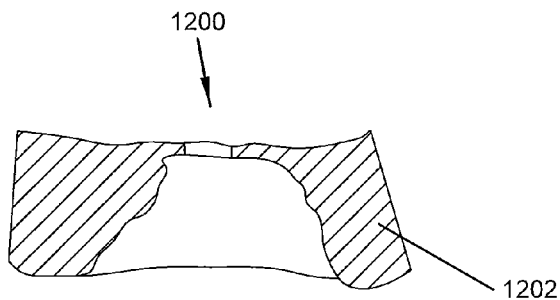
FIG. 27i illustrates a thru-hole defect in an acetabular medial wall where a covering may be placed, in accordance with one embodiment.
Figure 27J:
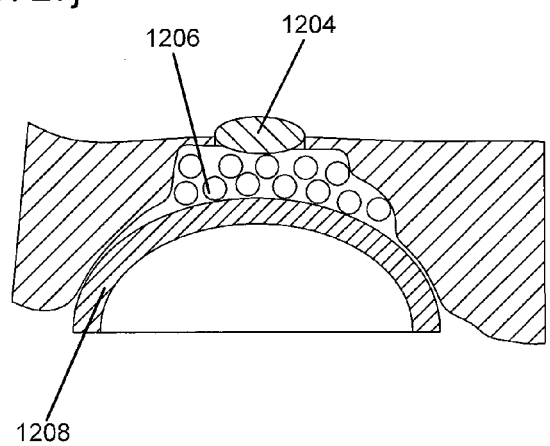
FIG. 27j illustrates a bridge/restrictor covering placed in the thru hole, in accordance with one embodiment.
Figure 27K:
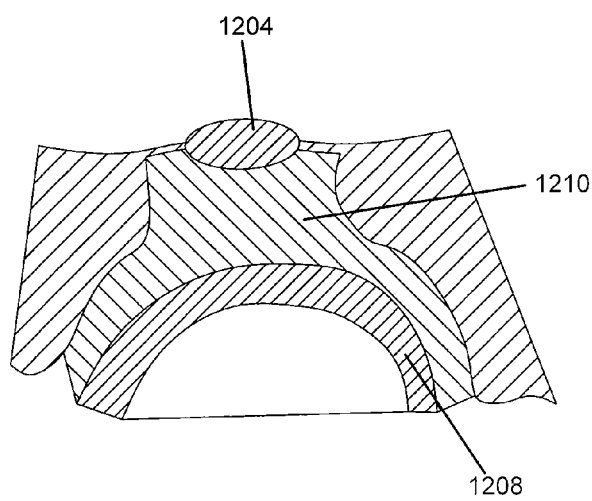
FIG. 27k illustrates bone cement used to fill the void between the covering and the shell implant, in accordance with another embodiment.

In some embodiments, an acetabular cup may be placed over a bridge/restrictor covering as previously discussed with respect to FIGS. 27a and 27b. Such embodiment may be useful for acetabular medial wall reconstruction. FIG. 27i illustrates a thru-hole defect 1200 in an acetabular medial wall 1202. FIG. 27j illustrates a bridge/restrictor covering 1204 placed in the thru hole. Graft material 1206 is placed over the covering 1204 to substantially fill the void between the covering and the acetabular cup 1208. In an alternative embodiment, shown in FIG. 27k, bone cement 1210 is used to fill the void between the covering 1204 and the shell implant 1208 and is provided in sufficient amount to facilitate wall healing.

Guided Bone Regeneration

In yet another embodiment, a covering and associated delivery system may be used in guided bone regeneration. Guided bone regeneration (GBR) is a surgical procedure using barrier membranes to direct growth of new bone at sites having insufficient volumes or dimensions for function or prosthesis placement. GBR is directed to the development of hard tissue. GBR may be applied, for example, in the oral cavity to support new hard tissue growth on the alveolar ridge to allow stable placement of dental implants. GBR may also be used for augmentation around implants placed in immediate or delayed extraction sockets, or for localized ridge augmentation for later implantation, filling bone defects after root resection, cystectomy, removal of retained teeth, or guided bone regeneration in dehiscense defects.

Generally, GBR is performed by first closing the wound to promote undisturbed and uninterrupted healing, whereupon angiogenesis occurs. A space is created to facilitate bone in-growth. A covering, forming a barrier membrane, may be implanted into the space. The covering may be configured to be resorbable or non-resorbable and, in some embodiments, may comprise a collagen material. The wound is stabilized to induce blood clot formation and to allow for uneventful healing.

ACL Reconstruction Surgery

Figure 28A:
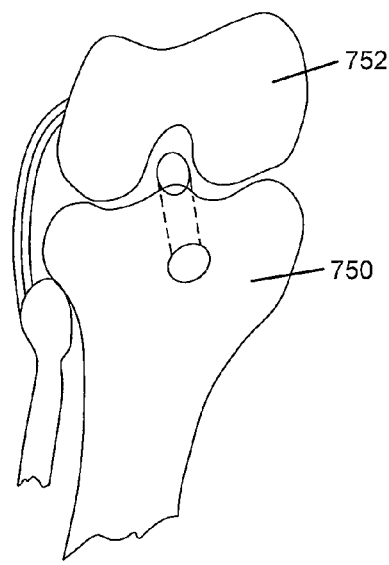
FIG. 28a illustrates an anterior view of a graft-containing covering placed into the tunnel entrance of a bone-tendon-bone graft of an ACL reconstruction surgery, in accordance with one embodiment.
Figure 28B:
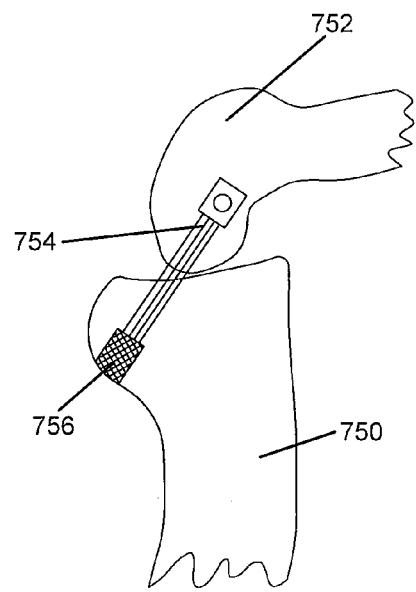
FIG. 28b illustrates a medial view of a graft-containing covering placed into the tunnel entrance of a bone-tendon-bone graft of an ACL reconstruction surgery, in accordance with one embodiment.

As shown in FIGS. 28a-39d, in a further embodiment, a covering may be used in a surgery for a torn Anterior Cruciate Ligament (ACL), which is one of the ligaments that connects the tibia 750 to the femur 752. A Bone-Tendon-Bone graft 754 may be used as a replacement of the ACL as shown in FIG. 28a in the anterior view, and FIG. 28b in the medial view. In this case, the knee is placed in flexion, and a drill is used to create a tunnel from the tubercle region of the tibia 750 into the femur 752. The implant is placed using standard techniques, and fixed into the tunnel. The graft-containing covering 756, in one embodiment, may be placed into the tunnel entrance, to close it off and to encourage bone growth up to the bone block anchored in the tibia, as shown in FIGS. 28a and 28b.

Figure 28C:
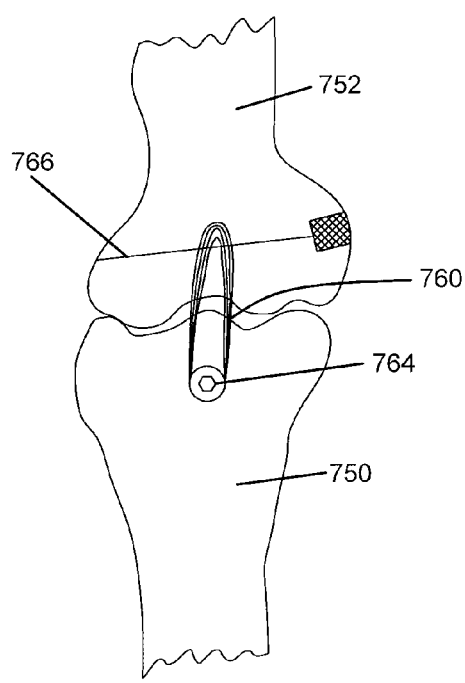
FIG. 28c illustrates an anterior view of a graft-containing covering used in a looped graft of an ACL reconstruction surgery, in accordance with another embodiment.
Figure 28D:
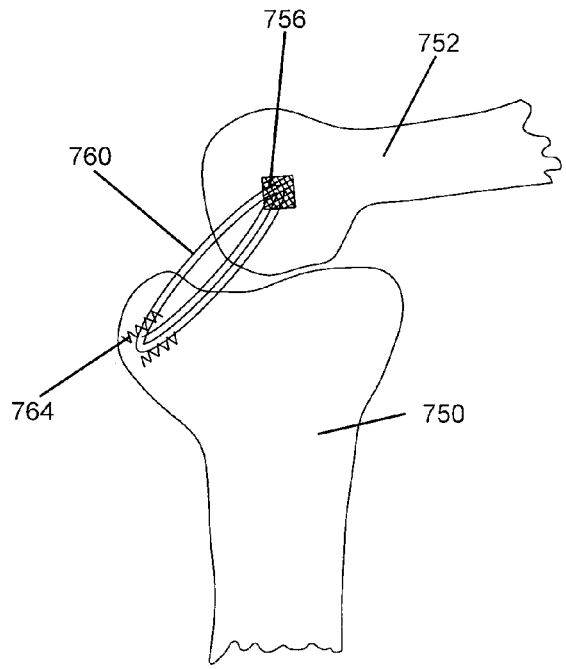
FIG. 28d illustrates a medial view of a graft-containing covering used in a looped graft of an ACL reconstruction surgery, in accordance with another embodiment.

In another embodiment, shown in FIGS. 28c and 28d, a looped graft 760, such as some synthetic grafts, hamstring grafts, and some tendon grafts, may be used. In this case, the loop is captured across a pin 766 in the femur 752, and the tibial 750 portion is tightened into place using an interference screw 764. The entry hole for the pin 766 can be plugged or capped using the covering 756, by pushing or packing it into position.

Revision Joint Surgery

Figure 29A:
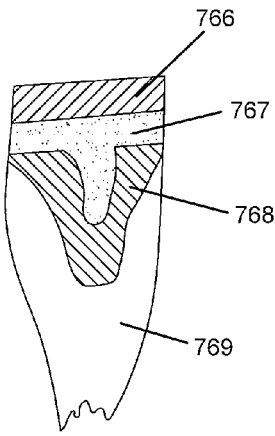
FIG. 29a illustrates a tibial implant that must be removed.
Figure 29B:
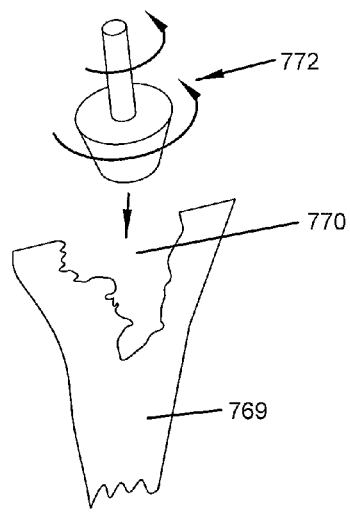
FIG. 29b illustrates the large defect left when cement is removed from a joint replacement implant and a rasping tool used to smooth the defect, in accordance with one embodiment.
Figure 29C:
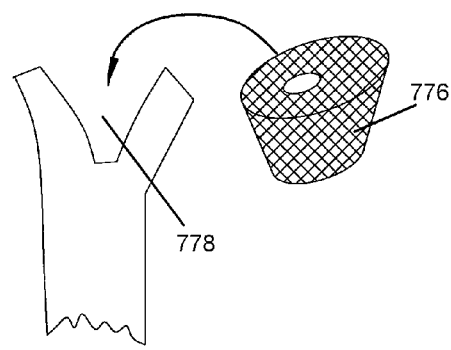
FIG. 29c illustrates where a doughnut shaped covering may be placed in the smoothed site, in accordance with one embodiment.
Figure 29D:
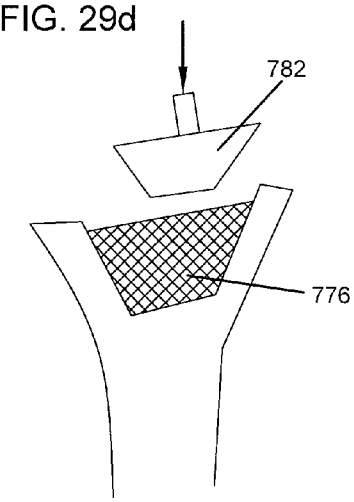
FIG. 29d illustrates a tapered impactor used to position the placed covering, in accordance with one embodiment.
Figure 29E:
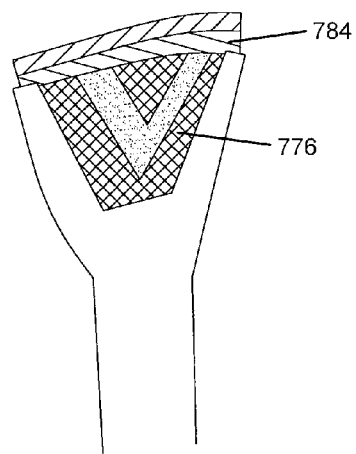
FIG. 29e illustrates a new impact placed over the covering, in accordance with one embodiment.

In one application, a covering and associated delivery system may be used in a simplified approach to repairing a defect created by the removal of a joint implant such as tibial implant. Generally, such covering may be used for proximal tibial, distal femoral, and proximal femoral revision joint surgery. The approach thus may be used for the femoral component of a hip implant, or in other revision joint arthroplasty applications. Typically joint replacement implants are cemented implants. FIG. 29a illustrates a tibial implant to be removed. The tibial bone 769 has a metallic prosthesis 767 with cement 768 holding the prosthesis 767 in the bone 769, with a polyethylene insert 766 placed on top. As illustrated in FIG. 29b during removal of the cement 768, a large volume of the cancellous bone may be removed as well, thereby creating a defect 770. This defect can be prepared to an even, smooth and, for example, conical geometry by reaming or rasping with an appropriate instrument 772. Tubular or cylindrical shaped preparation beds may also be accommodated. A tubular, tapered or doughnut shaped covering containing graft material 776 may be placed into the prepared site 778, as shown in FIG. 29c. Several sizes of coverings may be provided to accommodate any variety of defect. A tapered impactor 782 may be used to press against the inner surface of the covering 776, and force the covering into the reamed, tapered surface 778. This is similar to "impaction grafting". A new implant 784 is then placed, for example by cementing in place.

Figure 30:
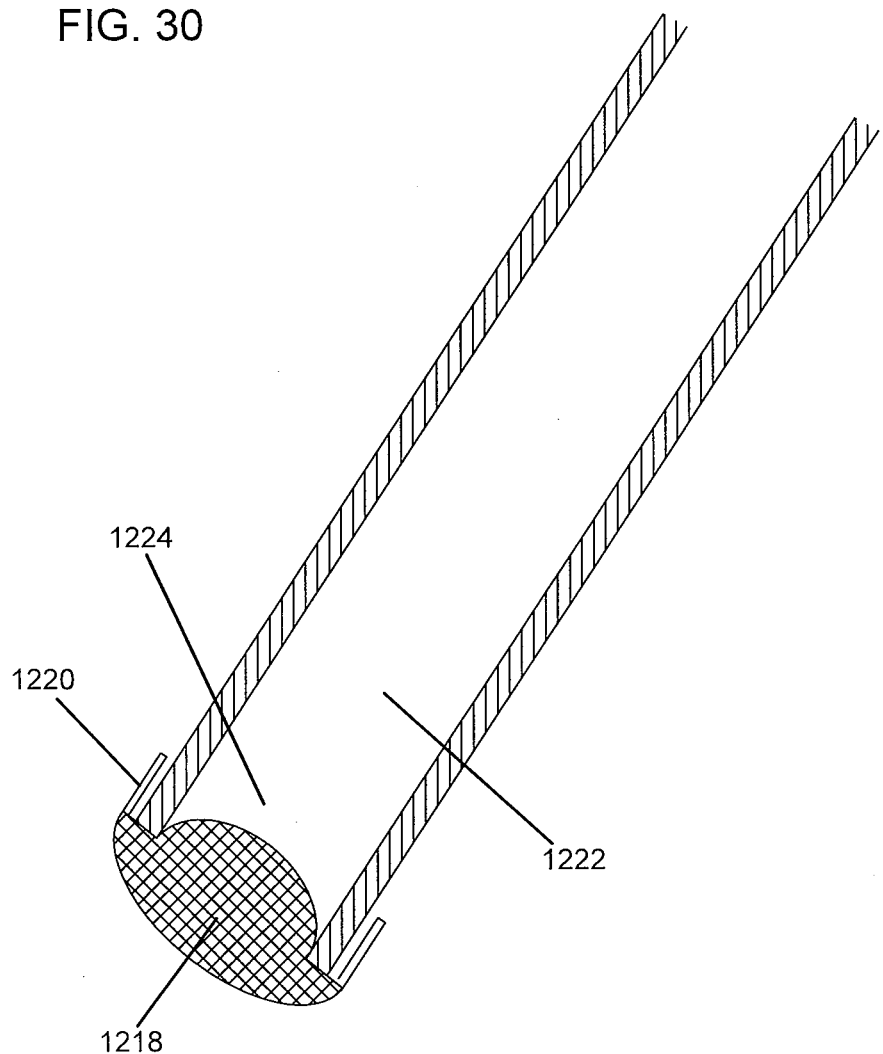
FIG. 30a illustrates an original metal implant cemented in the tibia prior to revision joint surgery, in accordance with one embodiment.
FIG. 30b illustrates the large defect created when the impact and cement of an original metal implant are removed, in accordance with one embodiment.
FIG. 30c illustrates a forming instrument used to compress a covering placed in the defect, in accordance with one embodiment.
FIG. 30d illustrates a revision implant seated and void filler placed between the revision impact and the covering, in accordance with one embodiment.
FIG. 30e illustrates a perspective view of a covering configured as an end-cap for treatment of an amputation, in accordance with one embodiment.
FIG. 30f illustrates a side view of a covering configured as an end-cap for treatment of an amputation, in accordance with one embodiment.
FIG. 30g illustrates a top view of a covering configured as an end-cap for treatment of an amputation, in accordance with one embodiment
FIG. 30h illustrates the covering placed at the end of a femur in the above-the-knee amputee, in accordance with one embodiment.
Figure 30A:
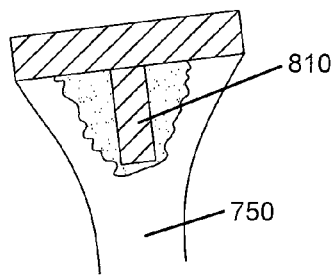
Figure 30B:
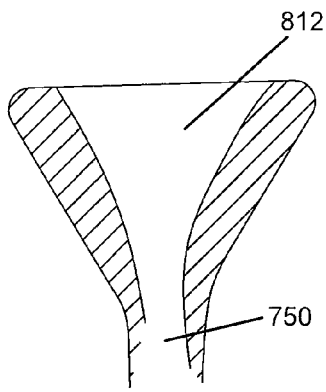
Figure 30C:
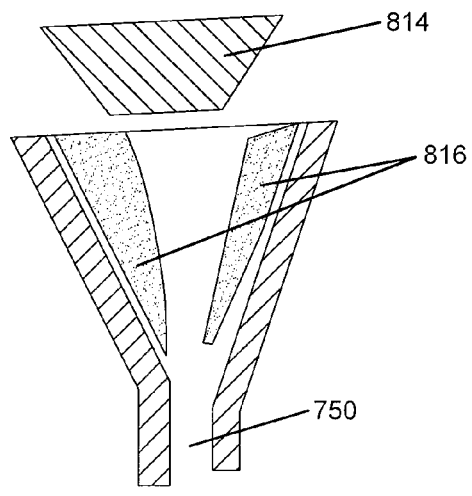
Figure 30D:
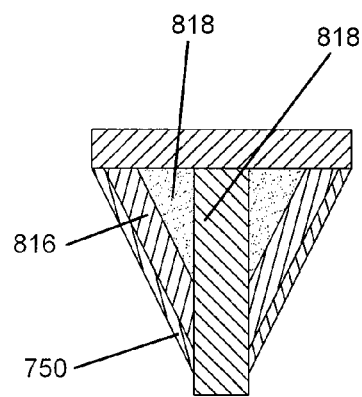

FIGS. 30a-30d illustrate placement of an impaction graft in the tibia 750. FIG. 30a illustrates an original metal implant 810 cemented in place in the tibia 750. The implant 810 and cement are removed, thus creating a large defect void 812, shown in FIG. 30b. A covering 816 is placed in the defect void 812 and a forming instrument 814 may be used to compress the covering 816 into a suitable shape, shown in FIG. 30c. A revision implant 818 then may be seated and void filler 818 placed between the revision implant and the covering 816, as shown in FIG. 30d.

Amputation

When performing an amputation, surgeons generally cut above the diseased or injured area so that a portion of healthy tissue remains to cushion bone. Sometimes the location of a cut may depend in part on its suitability to be fitted with an artificial limb, or prosthesis. The first step in performing an amputation involves ligating the supplying artery and vein, to prevent hemorrhage. The muscles are transected, and finally the bone is sawed through with an oscillating saw Skin and muscle flaps are then transposed over the stump, occasionally with the insertion of elements to attach a prosthesis.

Figure 30E:
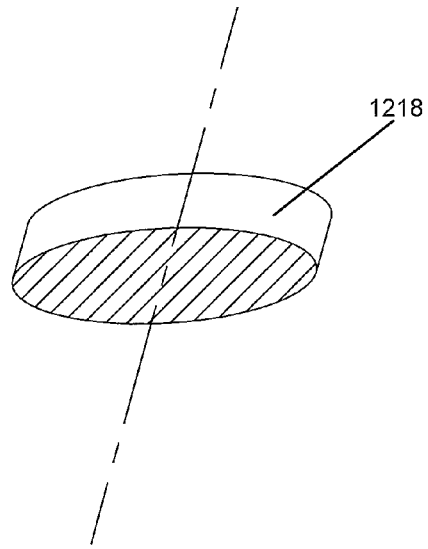
Figure 30F:
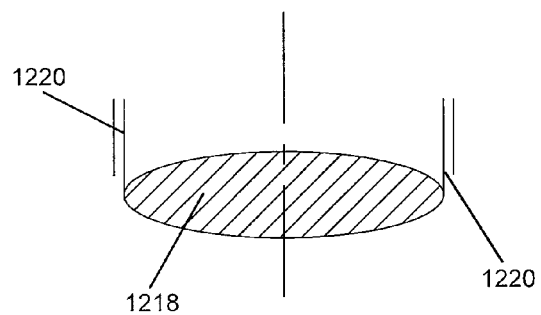
Figure 30G:
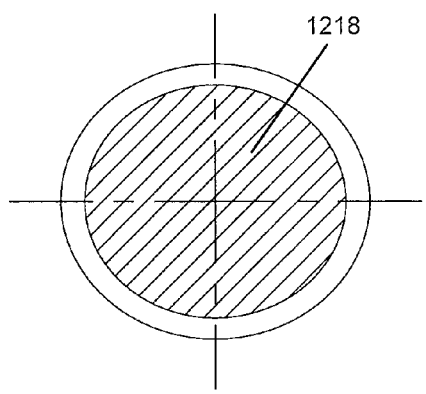

In some embodiments, a covering may be configured as an end-cap for treatment of an amputation, to provide a more stable site for a bony fixed prosthesis or to solidify the bony support for an externally attached prosthesis. FIG. 30e illustrates a perspective view, FIG. 30f illustrates a side view, and FIG. 30g illustrates a top view of such embodiment. As shown, the covering 1218 may be formed as a substantially flat and circular bag. Flanges may extend from the covering 1220. A single flange may be provided around substantially the entire perimeter of the covering or one or more flanges may be provided extending from the covering. In the embodiment shown, two flanges 1220 are provided on generally opposite ends of the covering 1218.

After preparing the bony surface, and optionally, elevating the periosteum, such covering may be placed, at the end of a femur in an above-the-knee amputee. FIG. 30h illustrates the covering as placed. The covering 1218 is placed on an end of the bone 1222, over the cortical bone, or may also be placed inside the intramedullary canal. The containment area of the covering may thus extend partially into the intramedullary canal 1224. The covering 1218 may be fixed via the flanges 1220. In some embodiments, sutures or other attachment mechanisms may be used to clamp the flange(s) to the bone. Muscle flap may be positioned over the covering once the covering is fixed in place.

Other

Generally, the delivery system may be applied to a pre-existing defect, to a created channel, or to a modified defect. Thus, for example, a channel may be formed in a bone, or a pre-existing defect may be cut to form a channel, for receipt of the delivery system. The covering may be configured to match the channel or defect. In some embodiments, the configuration of the covering may be chosen to match the channel or defect. In other embodiments, the channel may be created, or the defect expanded or altered, to reflect a configuration of the covering. The covering may be placed in the defect or channel and, optionally, coupled using attachment mechanisms. Similarly, a covering may be used to fill a gap created by fracture in vertebroplasty or kyphoplasty.

Figure 31A:
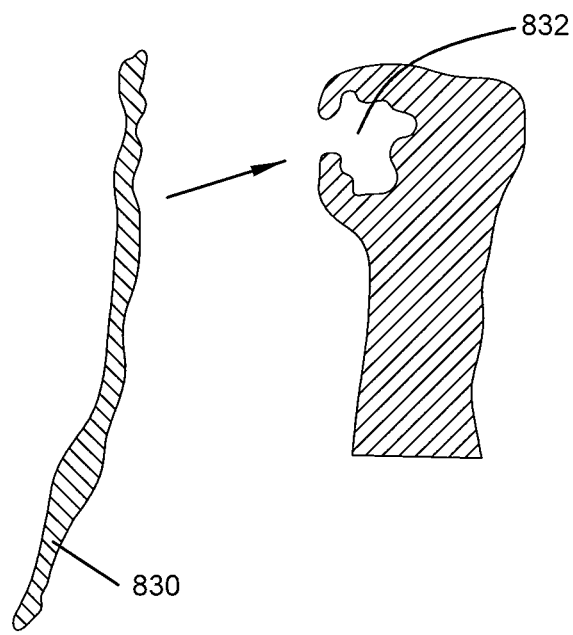
FIG. 31a illustrates a covering formed as a long tube or snake and where it can be placed in a site, in accordance with one embodiment.
Figure 31B:
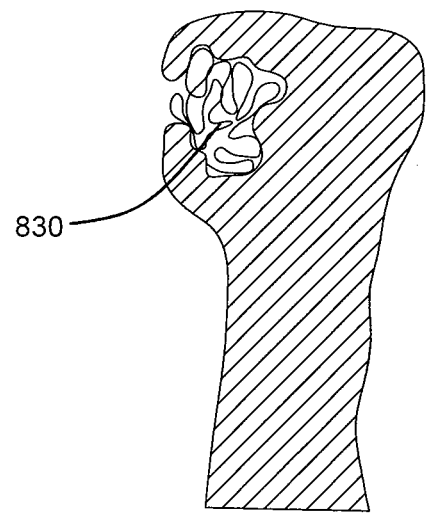
FIG. 31b illustrates a snake covering placed in a site, in accordance with one embodiment.

FIG. 31a illustrates a covering formed as a long tube 830, generally referred to as a snake structure. The covering 830 may be placed in a cyst or tumor site that has been evacuated 832. Placement may be done percutaneously or in an open procedure. In another embodiment, as shown in FIG. 31b, a defect may be filled with a long ribbon-like or "snake" covering containing graft 830. The covering may be inserted into the defect by folding the covering upon itself to completely fill and pack the defect.

Figure 32A:
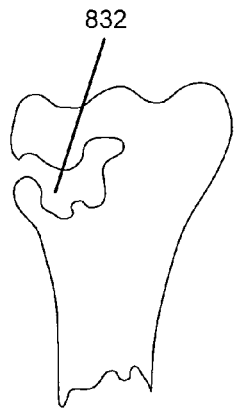
FIG. 32a illustrates a defect that can be filled by a covering, in accordance with one embodiment.
Figure 32B:
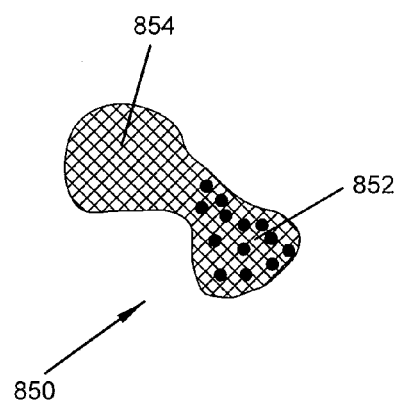
FIG. 32b illustrates a covering that is partially filled with graft and partially empty, in accordance with one embodiment.
Figure 32C:
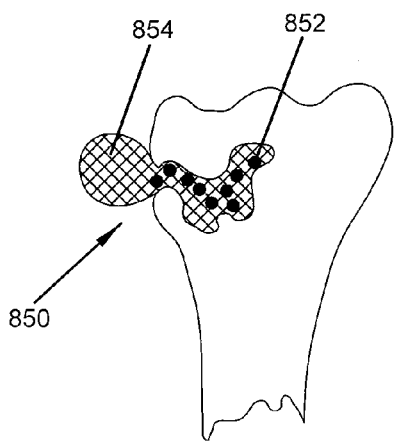
FIG. 32c illustrates placement of the partially filled and partially empty covering in the defect, in accordance with one embodiment.
Figure 32D:
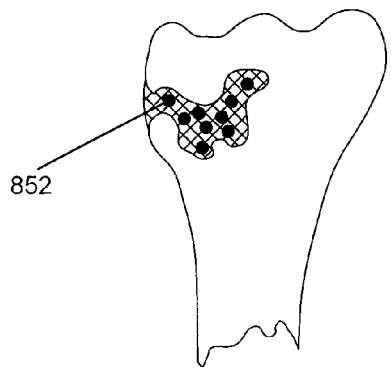
FIG. 32d illustrates removal of the empty portion of the covering from the site, in accordance with one embodiment.

In some embodiments, a covering may be used to fill a concave defect. The covering may be provided such that substantially complete filling of the defect does not substantially deform the covering material. Further, the covering may be provided in a pre-filled configuration. In a further embodiment, a covering and associated delivery system may be used to fill a concavity, which is a contained defect. A covering that is at least partly filled with graft materials may be used to fill a defect 832, which is shown in FIG. 32a. Several different sizes of coverings, representing different filling volumes may be provided. A "trial" implant may be used to identify the volume of the defect and to select an appropriately sized covering. FIG. 32b shows a covering 850 that is partially filled with graft material 852, and partially empty 854. FIG. 32c shows the graft material 852 is packed into the space, and carries the covering in as it is packed into the defect. Packing can be performed manually, or by using a tamp, for example. As the graft material is packed into position, graft inside the covering may be manipulated into the defect or out into the unfilled end. The end of the covering containing empty space 854 and any unused graft materials is collected, and the covering is re-sized by any suitable means, such as by crimping, clipping, tying, twisting and tying, heat sealing, suturing or sewing, etc. Optionally, the excess bag material might be cut and removed, as shown in FIG. 32d.

Figure 32E:
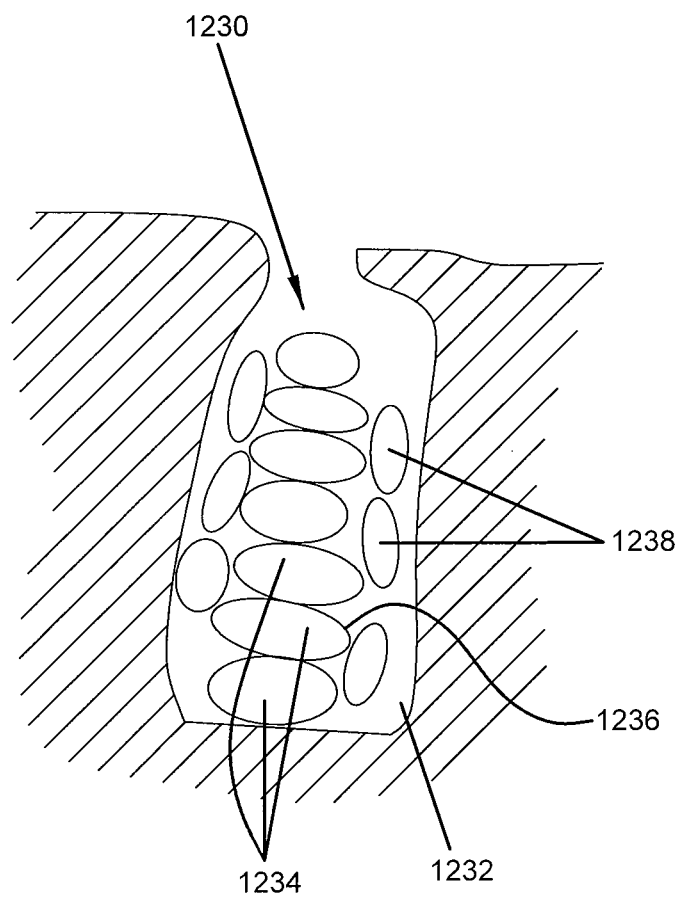
FIG. 32e illustrates a first embodiment of a foldable and stackable covering used to treat an irregular bone void, in accordance with one embodiment.

FIG. 32e illustrates a first embodiment of a foldable and stackable covering 1230 used to treat an irregular bone void 1232. As shown, the foldable and stackable covering 1230 includes segments of a first type 1234, segments of a second type 1236, and segments of a third type 1238. The segments of the first type 1234 are generally stacked on one another to fill a height of the void 1232. The segments of the third type 1238 extend along the sides of the segments of the first type 1234 and thus assist in filling the width of the void 1232. The segments of the second type 1236 span the segments of the first type 1234 and the segments of the third type 1238.

Figure 32F:
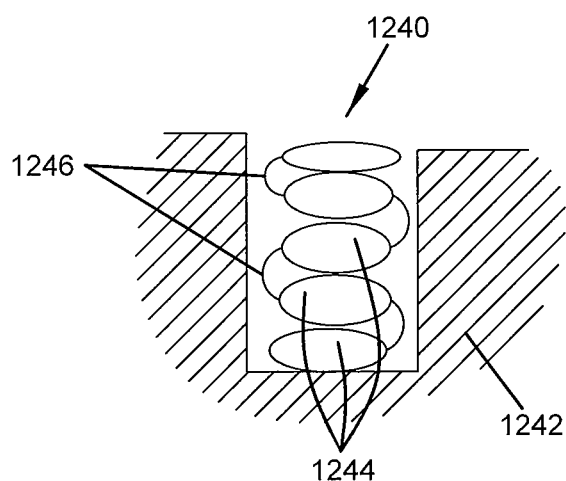
FIG. 32f illustrates a second embodiment of a foldable and stackable covering used to treat an irregular bone void, in accordance with one embodiment.

FIG. 32f illustrates a second embodiment of a foldable and stackable covering 1240 used to treat an irregular bone void 2142. As shown, the foldable and stackable covering 1240 includes segments of a first type 1244 and segments of a second type 1246. The segments of the first type 1244 are generally evenly sized and evenly filled. The segments of the second type 1246 are sized such that the segments of the first size 1244 may be folded over 180°. Thus, as stacked in a bone void 1242, the segments of the first type 1244 stack generally evenly on top of one another.

Figure 32G:
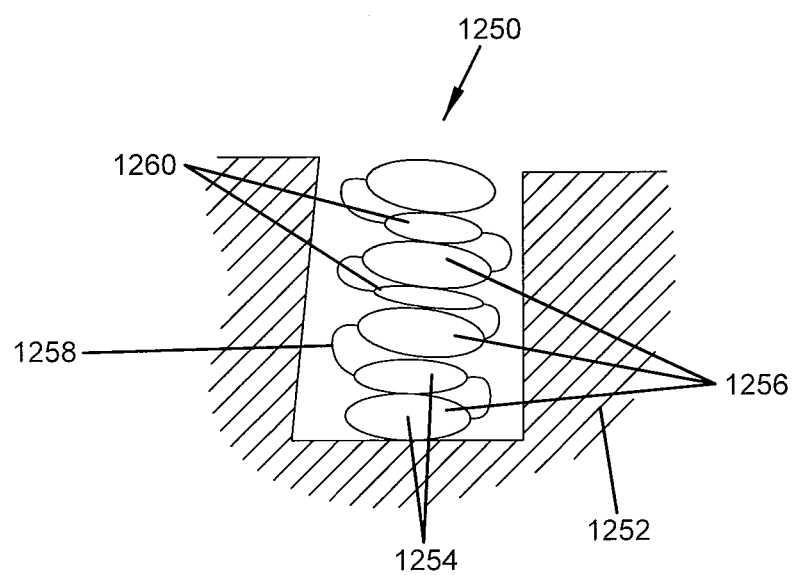
FIG. 32g illustrates a third embodiment of a foldable and stackable covering used to treat an irregular bone void, in accordance with one embodiment.

FIG. 32g illustrates a third embodiment of a foldable and stackable covering 1250 used to treat an irregular bone void 1252. As shown, the foldable and stackable covering 1250 includes segments of a first type 1254 and segments of a second type 1258. The segments of the first type 1254 are generally evenly sized but alternate between a first fill level 1256 and a second fill level 1260. The segments of the second type 1258 are sized such that the segments of the first size 1254 may be folded over 180°. Thus, as stacked in a bone void 1252, the segments of the first type 1254 stack generally evenly on top of one another but with differing heights contributed by the different fill levels in the segments of the first type 1254. Such configuration facilitates tighter packing of the bone void 1252 and deforms to larger covering profiles.

Figure 32H:
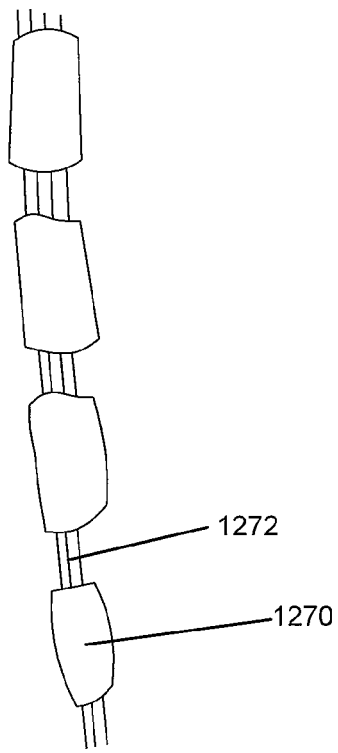
FIG. 32h illustrates a covering used as a sternum closure after open heart surgery, in accordance with one embodiment.
Figure 32I:
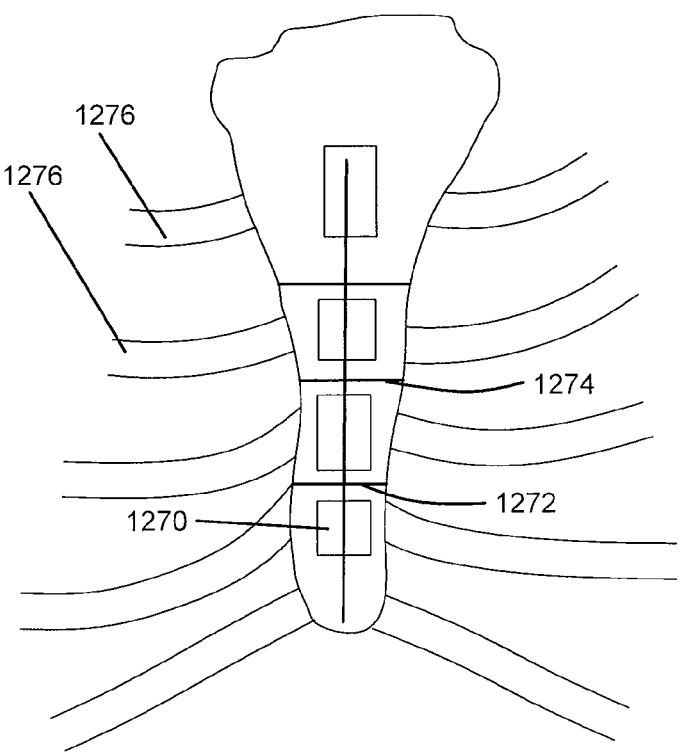
FIG. 32i illustrates a covering used as a sternum closure after open heart surgery placed in the site, in accordance with one embodiment.

FIGS. 32h and 32i illustrate a covering used as a sternum closure after open heart surgery. As shown, the covering includes segments of a first type 1270 and segments of a second type 1272. The segments of a first type 1270 may be filled with a substance such as a graft material. The segments of a first type 1270 may be generally sized and spaced to correspond with rib locations. The segments of a second type 1272 extend between the segments of the first type 1270 and may comprise unfilled covering or may comprise other material. FIG. 32i illustrates the covering as placed. Closure wires 1274 are placed through the segments of a second type 1272. The segments of a first type 1270 generally align with the ribs 1276.

In alternative embodiments, such covering configuration may be used to treat non-unions and in reoperations. A broken bone that does not grow back together is called nonunion. This can happen with certain types of fractures. Nonunion can be treated by replacing the affected joint with an artificial joint or by bone grafting. Bone grafting involves placing additional bone around the area of the nonunion. Additionally, some patients who have had, for example, spinal fusion, may require reoperation if symptoms return after several years. About 10% to 20% of people who have had surgery need to have surgery again. Reoperation may be necessary if, for instance: spinal stenosis develops in another area of the spine; an earlier surgical procedure was not effective in controlling symptoms; instability develops, or fusion does not occur: or regrowth of tissue (lamina) presses on the spinal cord or spinal nerve roots. A covering such as provided herein may be configured to span ends of a broken bone in a non-union, as an implant for an artificial joint, etc.

At the time just prior to when the delivery system is to be placed in a defect site, optional materials, e.g., autograft bone marrow aspirate, autograft bone, preparations of selected autograft cells, autograft cells containing genes encoding bone promoting action, etc., can be combined with the covering and/or with a substance provided within the covering. The delivery system can be implanted at the bone repair site, if desired, using any suitable affixation means, e.g., sutures, staples, bioadhesives, screws, pins, rivets, other fasteners and the like or it may be retained in place by the closing of the soft tissues around it.

Collagen Covering

Collagen materials may be used to form the covering. The collagen material may be processed to any suitable level. For example, the collagen material may be minimally processed. The collagen material may be treated with enzymes. For example, human-derived collagen may be enzymatically treated to yield a collagen material having a preserved amount of native constituents but with immunologically active glycoproteins and recombinant collagen removed. Collagen material may be constructed from collagen fibers, fibrils, microfibrils, particles, threads, strands, etc. The materials may be processed by chemical treatments (e.g., with enzymes, enzyme deactivation solutions, alcohols and/or cross-linking agents) and/or by physical treatments (e.g., blending, freezing, lyophilizing, casting, pressing, molding). The collagen material may be provided as a sheet, may be woven (using, for example, textile techniques), knitted, braided, non-woven (using, for example, felting processes), may be formed as a film, or may be provided in any suitable configuration. In embodiments wherein the collagen material is provided as a sheet, the sheet may have holes created therein and, further, may be stretched to increase the size of the holes. The collagen material may be treated to have different properties when wetted—such as increased flexibility or malleability. Such wetting may be, for example, by any fluid including blood, serum, saline, and water. In accordance with one embodiment, the collagen material is a collagen product disclosed in U.S. Patent Publication Nos. 2008/0195202 for Methods for Collagen Processing and Products Using Processed Collagen and 2008/0260794 for Collagen Products and Methods for Producing Collagen Products, herein incorporated by reference in their entireties for all purposes.

Figure 33:
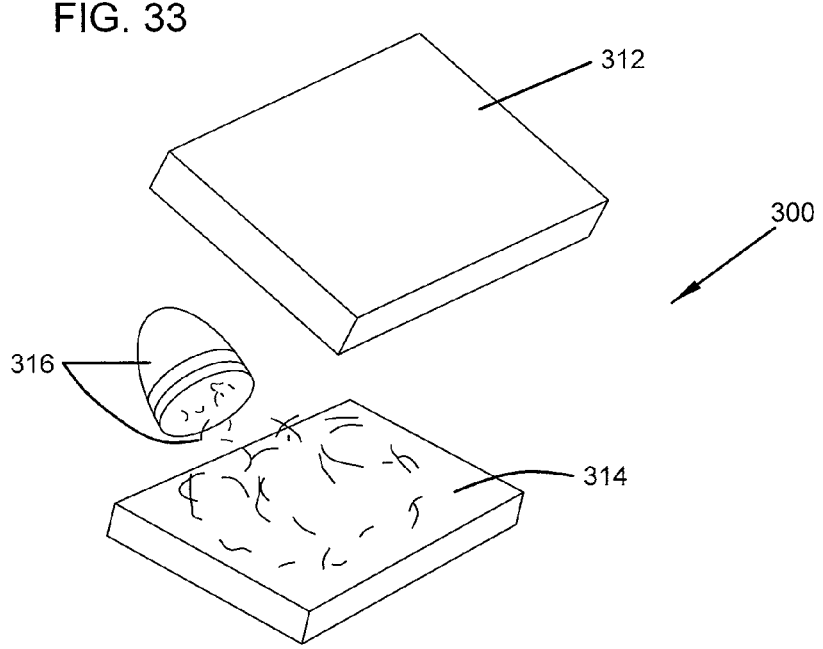
FIG. 33 illustrates a covering comprising a first sheet and a second sheet with a substance being provided therebetween, in accordance with one embodiment.
Figure 34:
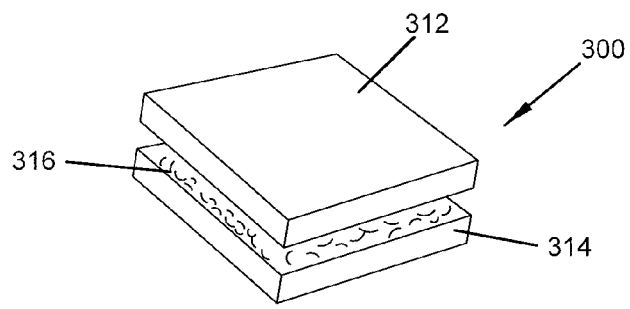
FIG. 34 illustrates a covering comprising a first sheet and a second sheet configured as a drug release system, in accordance with one embodiment.
Figure 35:
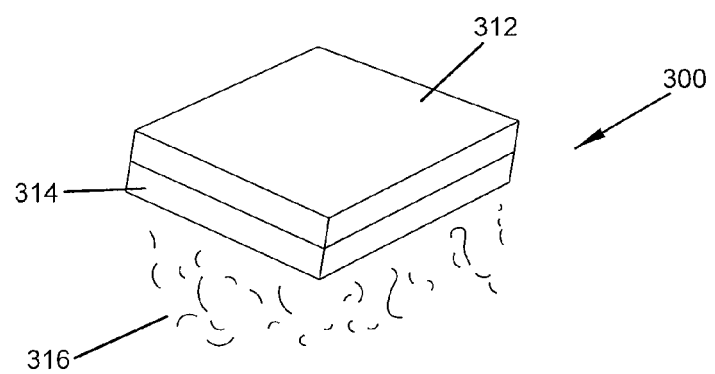
FIG. 35 illustrates a drug delivery from the drug release system of FIG. 2, in accordance with one embodiment.

In accordance some embodiments, a covering may be configured as a pad or sheet and formed for drug release. Accordingly, as shown by FIGS. 33-35, a delivery system 300 may include a covering comprising a first layer 314 and a second layer 312 and a substance placed and contained therebetween. In some embodiments, the first 314 and second layers 312 may comprise a material such as a collagen material. In various embodiments, the collagen material may be processed. FIGS. 33 and 34 illustrate formation of the covering 300. As shown, a first sheet 314 is provided. The sheet 314 may be wet, for example, to facilitate adherence of a substance 316 for delivery on the sheet. A substance 316 for delivery is then provided on the sheet 314. As shown in FIG. 33, the substance 314 may comprise a drug powder 316 that is sprinkled on or otherwise provided on or adhered in or to the first sheet 314. The second sheet 312 is then placed over the first sheet 314 and the material 316, as shown in FIG. 34. In some embodiments, the second sheet 316 may be wet. FIG. 35 illustrates drug delivery from the delivery system 300. Generally, with biological fluid and cells permeating the first and second sheets, the substance provided therebetween is released in a relatively controlled manner.

In further embodiments, more than two sheets or layers of material may be used. For example, a delivery system may be provided including a covering having first, second, third, and fourth layers of material. Substances may be provided between each of the layers. The substances may be the same or different between the layers. For example, a bone graft material may be provided between the second and third layers with a different substance, such as an active substance or an antibiotic, may be provided between the first and second layer and between the third and fourth layer.

Figure 36:
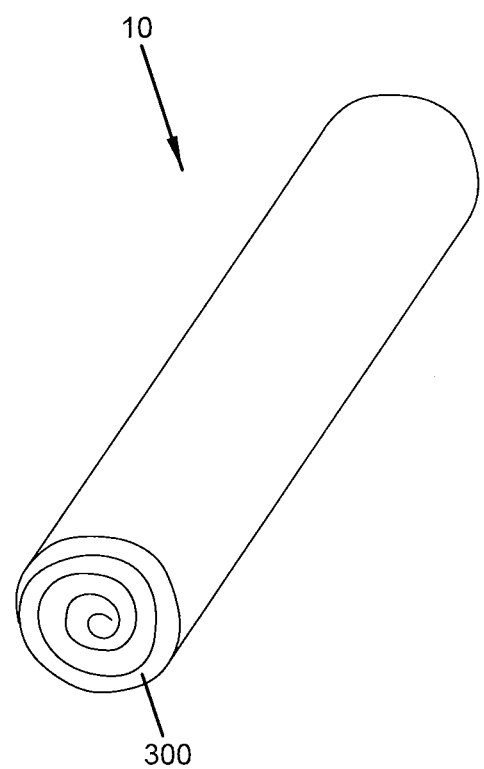
FIG. 36 illustrates a cylindrical covering, in accordance with one embodiment.

A delivery system such as shown in FIGS. 33-35 may be further configured. For example, as shown in FIG. 36, a generally cylindrical delivery system 10 may be formed from the delivery system 300 of FIGS. 33-35. This form may be achieved, for example, by rolling the delivery system 300 into a tubular or generally cylindrical form. An adhesive may be used on the delivery system 300 to facilitate formation into the generally cylindrical form. Attachment mechanisms may be provided on the delivery system, for example at ends of a tubular configuration.

Figure 37:
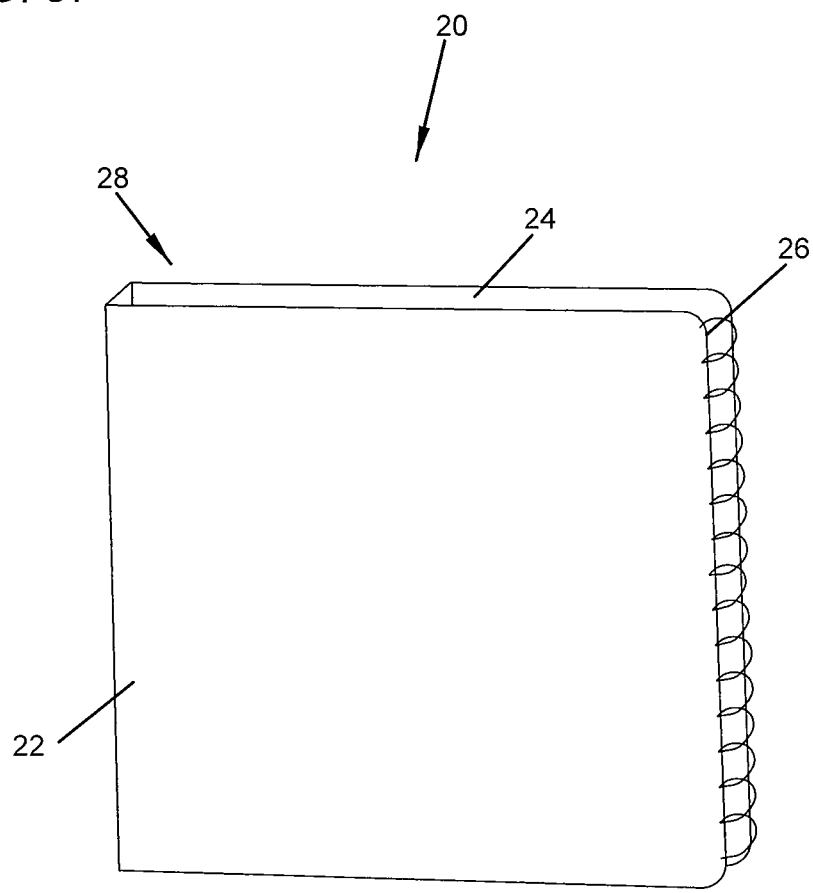
FIG. 37 illustrates a pouch covering, in accordance with one embodiment.

In yet a further embodiment, shown in FIG. 37, one or more sheets may be coupled to form a pouch or bag covering 20. Alternatively, the sheet (combined with other sheets as appropriate) may be formed into a tube, a pillow, or any other desired shape. The sheets may comprise a single layer of material or may comprise a multi-layer construct such as shown in FIGS. 33-35. As shown in FIG. 37, two layers 22 and 24 may be coupled along, for example, first, second, and third edges to form a covering. Coupling may be by, for example, sealing the first layer and the second layer together. Such sealing may be done by welding, suturing, adhesives, or other. In the embodiment shown, sutures 26 are used for coupling the first layer 22 to the second layer 24. In some embodiments, one edge of the covering may be left open. In the embodiment shown, the upper edge 28 is left unsealed. A substance for delivery thus may be inserted into the covering 20 through the open edge 28. That edge may be closed after filling the covering or may be left open. In one embodiment, a pillow may be formed where the outer layer of the pillow includes two layers, with an active substance between the two layers; the pillow further comprises an interior, into which another active substance (in addition to or instead of the active substance between the layers of the covering) may be provided, such as a bone growth material (demineralized bone, or bone morphogenetic protein).

Soft Tissue Augmentation

In some embodiments, a covering may be used for skin or other soft tissue augmentation. For example, a covering may be configured as a relatively thin tube and may be filled with a material such as collagen, artificial skin, cells, or other material useful in soft tissue augmentation. The covering may be delivered, for example, into wrinkles or other soft tissue. In some embodiments, the covering may be delivered via injection.

Testing Applications

In some embodiments, a delivery system such as provided herein may be used in testing bone, either in vitro or in animal in vivo assays. For example, in in vitro applications, a covering comprising a mat may contain a graft and may be placed in a petri dish. Alternatively, a covering comprising a cylinder may be placed in a bioreactor. In in vitro applications, a covering may be used to deliver DBM ectopically in an athymic rat assay. Similarly, a delivery system may be used in mosaic plasty-like applications such as where cartilage is grown on a surface of a cylinder of material using tissue engineering methods such as a bioreactor.

IX. CONCLUSION

In accordance with various embodiments, a delivery system for delivery a substance in vivo is provided. The delivery system comprises a covering and a substance. The covering may be a single or multi-compartment structure capable of at least partially retaining a substance provided therein until the covering is placed at a surgical site. Upon placement, the substance may be released (actively or passively) to the surgical site. The covering may participate in, control, or otherwise adjust, the release of the substance. The delivery system may be used to control availability of a substances provided within the delivery system to cells and tissues of a surgical site over time.

Various delivery techniques may be used for implanting or placing a delivery system such as provided herein. These include attaching the covering to bone, attaching the covering to soft tissue (such as muscle, ligament, or tendon), delivering the covering through a cannula, delivering the covering through a drill hole or tract, placing the covering in an open or mini-open procedure, wrapping the covering around threads of another device (such as a cage, screw, dental implant, or similar), placing the covering a two-part procedure (delivering the covering to the site and filling the covering at the site), as part of a minimally invasive procedure, and in a procedure generally comprising "dumping" the delivery system at the site.

U.S. Pat. No. 4,430,760 for Nonstress-bearing Implantable Bone Prosthesis, U.S. Pat. No. 6,740,093 for Method and Apparatus for Treating a Vertebral Body, U.S. Pat. No. 4,755,184 for Bone Augmentation Implant, U.S. Pat. No. 5,571,189 for Expandable Fabric Implant for Stabilizing the Spinal Motion Segment, U.S. Pat. No. 7,220,282 Annulus-Reinforcing Band, U.S. Pat. No. 7,208,015 for Bone Repair Device, and U.S. Patent Publication No. 2007/0073401 for Method for Repairing Bone disclose various fabrics and structures for containing materials for implanting in the body and are herein incorporated by reference in their entireties.

Although the invention has been described with reference to preferred embodiments, persons skilled in the art will recognize that changes may be made in form and detail without departing from the spirit and scope of the invention.

What is claimed is:

1. A delivery system comprising:
 a plurality of operably linked segments comprising: a first segment and a second segment of a first type each comprising a flexible mesh covering material defining at least one compartment, the at least one compartment of the first segment of the first type retaining fully demineralized bone fibers therein and the at least one compartment of the second segment of the first type retaining surface demineralized bone chips therein, wherein said flexible mesh covering material comprises a biodegradable polymer, and a first segment of a second type, wherein the first segment of the second type operably links the first and second segments of the first type, and the second type is comprised of a covering material comprising a biodegradable mesh polymer.

2. The delivery system of claim 1, wherein the first segment of the second type contains little or no fully demineralized bone fibers and surface demineralized bone chips.

3. The delivery system of claim 1, wherein the delivery system is designed for use in a sternum closure procedure.

4. The delivery system of claim 1, wherein the delivery system is used in filling an irregular shaped bone void.

5. The delivery system of claim 4, wherein at least two segments of the first segment type within the bone void are packed substantially parallel.

6. The delivery system of claim 1, wherein the delivery system is terminally sterilized.

7. The delivery system of claim 6, wherein the delivery system is sterilized by a method chosen from the group consisting of: gamma radiation, electron beam radiation, UV irradiation, cobalt source radiation; autoclaving, dry heating, and by supercritical fluid exposure.

8. The delivery system of claim 7, wherein the fully demineralized bone fibers and surface demineralized bone chips are sterilized by a method other than that used to sterilize the covering material.

9. The delivery system of claim 1, wherein the biodegradable polymer covering comprises at least one of poly(lactic acid) (PLA), poly(glycolic acid) (PGA), poly(lactic-co-glycolic acid) (PLGA) and polyhydroxyalkanoates.

* * * * *